(12) United States Patent
Ghergurovich et al.

(10) Patent No.: US 9,084,794 B2
(45) Date of Patent: Jul. 21, 2015

(54) FATTY ACID SYNTHASE INHIBITORS

(75) Inventors: Jonathan Michael Ghergurovich, Collegeville, PA (US); Michael Lee Moore, Collegeville, PA (US); Cynthia Ann Parrish, Collegeville, PA (US); Lance Howard Ridgers, Collegeville, PA (US); Hongyi Lu, Collegeville, PA (US)

(73) Assignee: GlaxoSmithKline Intellectual Property (No. 2) Limited, Brentord, Middlesex (GB)

( * ) Notice: Subject to any disclaimer, the term of this patent is extended or adjusted under 35 U.S.C. 154(b) by 0 days.

(21) Appl. No.: 14/238,418

(22) PCT Filed: Aug. 16, 2012

(86) PCT No.: PCT/US2012/051064
§ 371 (c)(1),
(2), (4) Date: Feb. 11, 2014

(87) PCT Pub. No.: WO2013/028447
PCT Pub. Date: Feb. 28, 2013

(65) Prior Publication Data
US 2014/0194415 A1 Jul. 10, 2014

Related U.S. Application Data

(60) Provisional application No. 61/525,402, filed on Aug. 19, 2011, provisional application No. 61/663,124, filed on Jun. 22, 2012.

(51) Int. Cl.
C07D 498/10 (2006.01)
A61K 31/5386 (2006.01)
A61K 45/06 (2006.01)

(52) U.S. Cl.
CPC ............ *A61K 31/5386* (2013.01); *A61K 45/06* (2013.01); *C07D 498/10* (2013.01)

(58) Field of Classification Search
CPC ............................ C07D 498/10; A61K 31/5386
USPC ......................................... 544/71; 514/230.8
See application file for complete search history.

(56) References Cited

U.S. PATENT DOCUMENTS 7,776,889 B2    8/2010   Chackalamannil et al.
2003/0055244 A1  3/2003   Scarborough et al.

FOREIGN PATENT DOCUMENTS

WO    WO2012/064642    5/2012

OTHER PUBLICATIONS

Chirgadze, et al. "The crystal structure of human a-thrombin complexed with active site-directed diamino benzo[b]thiophene derivatives: A binding mode for a structurally novel class of inhibitors" Protien Science, 9: pp. 29-36, 2000.

*Primary Examiner* — Kahsay Habte
(74) *Attorney, Agent, or Firm* — Wayne J. Dustman; Edward R. Gimmi

(57) ABSTRACT

This invention relates to spirocyclic piperidines according to Formula (I) and the use of spirocyclic piperidines for the modulation, notably the inhibition of the activity or function of fatty acid synthase (FAS). Suitably, the present invention relates to the use of spirocyclic piperidines in the treatment of cancer.

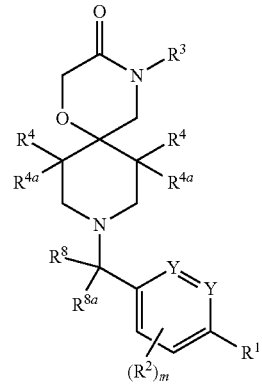

26 Claims, No Drawings

FATTY ACID SYNTHASE INHIBITORS

This application is a 371 of International Application No. PCT/US2012/051064, 16 Aug. 2012, which claims the benefit of U.S. provisional application 61/525,402 filed 19 Aug. 2011 and U.S. provisional application 61/663,124 filed 22 Jun. 2012.

FIELD OF INVENTION

This invention relates to novel spirocyclic piperidines which are inhibitors of fatty acid synthase (FAS), to pharmaceutical compositions containing them, to processes for their preparation, and to their use in therapy for the treatment of cancers.

BACKGROUND

Fatty acids have an essential role in a variety of cellular processes including building blocks for membranes, anchors for targeting membrane proteins, precursors in the synthesis of lipid second messengers and as a medium to store energy, (Menendez J S and Lupu R, *Fatty acid synthase and the lipogenic phenotype in cancer pathogenesis*, Nature Reviews Cancer, 7: 763-777 (2007)). Fatty acids can either be obtained from the diet or can be synthesized de novo from carbohydrate precursors. The biosynthesis of the latter is catalyzed by the multi-functional homodimeric FAS. FAS synthesizes long chain fatty acids by using acetyl-CoA as a primer and Malonyl Co-A as a 2 carbon donor, and NADPH as reducing equivalents (Wakil S J, Lipids, *Structure and function of animal fatty acid synthase*, 39: 1045-1053 (2004), Asturias F J et al., *Structure and molecular organization of mammalian fatty acid synthase*, Nature Struct. Mol. Biol. 12:225-232 (2005), Maier T, et al., *Architecture of Mammalian Fatty Acid Synthase at 4.5 ÅResolution*, Science 311:1258-1262 (2006)).

De novo fatty acid synthesis is active during embryogenesis and in fetal lungs where fatty acids are used for the production of lung surfactant. In adults, most normal human tissues preferentially acquire fatty acids from the diet. Therefore, the level of de novo lipogensis and expression of liopogenic enzymes is low (Weiss L, et al., *Fatty-acid biosynthesis in man, a pathway of minor importance. Purification, optimal assay conditions, and organ distribution of fatty-acid synthase. Biological Chemistry Hoppe-Seyler* 367(9):905-912 (1986)). In contrast, many tumors have high rates of de novo fatty acid synthesis (Medes G, et al., *Metabolism of Neoplastic Tissue. IV. A Study of Lipid Synthesis in Neoplastic Tissue Slices in Vitro*, Can Res, 13:27-29, (1953)). FAS has now been shown to be over expressed in numerous cancer types including prostate, ovary, colon, endometrium lung, bladder, stomach and kidney (Kuhajda F P, *Fatty-acid synthase and human cancer: new perspectives on its role in tumor biology*, Nutrition; 16:202-208 (2000)). This differential expression and function of FAS in tumors and normal cells provide an approach for cancer therapy with the potential of a substantial therapeutic window.

Pharmacological and small interference RNA mediated inhibition of FAS has demonstrated a preferential inhibition of cancer cell proliferation. Additionally, these inhibitors induce apoptosis in cancers cells in vitro and retard growth in human tumors in murine xenograft models in vivo (Menendez J S and Lupu R, Nature Reviews Cancer, 7: 763-777 (2007)). Based upon these findings, FAS is considered a major potential target of antineoplastic intervention. Thus, there is a need for inhibitors of FAS.

SUMMARY OF THE INVENTION

This invention relates to compounds of the Formula (I), as shown below:

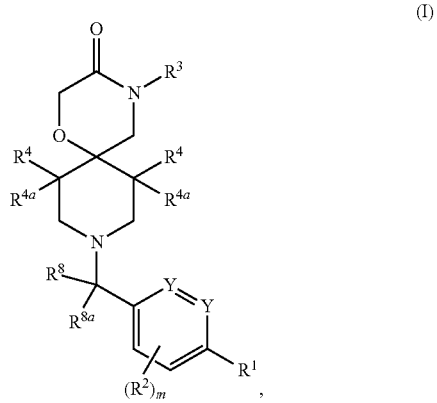

wherein $R^1$ is phenyl, 5- or 6-membered heteroaryl, naphthyl, 9- or 10-membered heterocyclyl; wherein said phenyl, 5- or 6-membered heteroaryl, naphthyl, 9- or 10-membered heterocyclyl, is optionally substituted with from 1 to 3 substituents independently selected from the group consisting of: optionally substituted $C_1$-$C_6$alkyl; —$CF_3$, $C_3$-$C_7$cycloalkyl, —C(=O)$C_1$-$C_4$alkyl, —$C_1$-$C_6$alkyl$C_3$-$C_7$cycloalkyl, —C(=O)$C_3$-$C_7$cycloalkyl, —C(=O)(phenyl), —C(=O)O$C_1$-$C_4$alkyl, —C(=O)OH, —C(=O)$NR^5R^6$, —O($C_2$-$C_4$alkyl)$NR^5R^6$, phenyl, —$SO_2C_1$-$C_4$alkyl, —$SO_2NR^5R^6$, cyano, oxo, hydroxyl, halogen, $C_1$-$C_4$alkoxy, hydroxy$C_1$-$C_4$alkyl-, $C_1$-$C_4$alkoxy$C_1$-$C_4$alkyl-, —$OCF_3$, —$NR^5R^6$, $R^5R^6NC_1$-$C_4$alkyl-, —$NR^7C$(=O)$C_1$-$C_4$alkyl, —$NR^7C$(=O)$NR^5R^6$, —$NR^7SO_2C_1$-$C_4$alkyl, —$NR^7SO_2NR^5R^6$ and $R^9$;

$R^5$ is selected from the group consisting of hydrogen, $C_1$-$C_4$alkyl, $C_3$-$C_7$cycloalkyl, —$C_1$-$C_3$alkyl$C_3$-$C_7$cycloalkyl, phenyl, and —$C_1$-$C_3$alkylphenyl;

$R^6$ is hydrogen, $C_1$-$C_4$alkyl, $C_3$-$C_7$cycloalkyl, or —$C_1$-$C_3$alkyl$C_3$-$C_7$cycloalkyl;

or $R^5$ and $R^6$ taken together with the nitrogen to which they are attached represent a 3- to 7-membered saturated ring optionally containing one other heteroatom which is oxygen, nitrogen, or sulfur, which is optionally substituted 1 or 2 times independently by oxo or $C_1$-$C_4$alkyl;

$R^7$ is hydrogen or methyl;

$R^9$ is a 5- or 6-membered heteroaryl ring containing 1 to 4 heteroatoms selected from oxygen, nitrogen, and sulfur, which is optionally substituted with 1 or 2 substituents selected from halogen, $C_1$-$C_4$alkyl, $CF_3$, $C_1$-$C_4$alkoxy, and —$NR^5R^6$;

each $R^2$ is selected from the group consisting of halogen, $C_1$-$C_6$alkyl, hydroxyl, and $C_1$-$C_4$alkoxy;

$R^3$ is selected from the group consisting of: $C_1$-$C_6$alkyl, $C_3$-$C_7$cycloalkyl, hydroxy$C_1$-$C_6$alky-, and $C_4$-$C_6$heterocycloalkyl, wherein said $C_1$-$C_6$alkyl, $C_3$-$C_7$cycloalkyl, hydroxy$C_1$-$C_6$alky-, and $C_4$-$C_6$heterocycloalkyl is optionally substituted with from 1 to 4 substituents independently selected from the group consisting of: halogen, $C_1$-$C_6$alkyl, —$CF_3$, $C_3$-$C_7$cycloalkyl, —C(=O)C₁-C₄alkyl, —C(=O)C₃-C₇cycloalkyl, —C(=O) (phenyl), —C(=O)OH, —C(=O)OC₁-C₄alkyl, —C(=O) NR⁵R⁶, phenyl, —SO₂C₁-C₄alkyl, —SO₂NR⁵R⁶, cyano, oxo, hydroxyl, C₁-C₄alkoxy, C₃-C₇cycloalkoxy, C₁-C₄alkoxyC₁-C₄alkyl-, —OCF₃, —NR⁵R⁶, R⁵R⁶NC₁-C₄alkyl-, —NHC(O)C₁-C₄alkyl, —NHCONR⁵R⁶, —NHSO₂C₁-C₄alkyl, and —NHSO₂NR⁵R⁶;

each R⁴ and R⁴ᵃ is independently selected from hydrogen, halogen, C₁-C₆alkyl, hydroxyl, or C₁-C₆alkoxy;

wherein R⁸ and R⁸ᵃ are independently selected from: hydrogen, deuterium, cyano, optionally substituted C₁-C₄alkyl, —C₁-C₄alkylhydroxy, C₁-C₆alkoxy, —C₁-C₄alkyl(=O)OH, —C₁-C₄alkyl(=O)OC₁-C₄alkyl, —C₁-C₄alkyl(=O)NR⁵R⁶, —C₁-C₄alkyl(=O)C₁-C₄alkyl, —C₁-C₄alkylSO₂C₁-C₄alkyl, —SO₂C₁-C₄alkyl, —C₁-C₄alkylSO₂N R⁵R⁶, —SO₂NR⁵R⁶, —C₁-C₄alkylNR⁵R⁶, —C₁-C₄alkylNR⁵SO₂C₁-C₄alkyl, —C₁-C₄alkylNR⁵SO₂NR⁵R⁶, —C₁-C₄alkylNR⁵C(=O)C₁-C₄alkyl, —C₁-C₄alkylNR⁵C(=O)NR⁵R⁶, C₁-C₄alkyl(=O) NR⁵OR⁶, triazolyl, and R⁹ wherein any C₁-C₄alkyl and C₁-C₆alkoxy moiety is optionally substituted with from 1 to 6 substituents independently selected from the group of: halogen, C₁-C₄alkyl, —CF₃, C₃-C₇cycloalkyl, —C(=O)C₁-C₄alkyl, —C(=O)C₃-C₇cycloalkyl, —C(=O)phenyl, —C₁-C₄alkyl(=O)OH, —C(=O)OC₁-C₄alkyl, —CONR⁵R⁶, phenyl, —SO₂C₁-C₄alkyl, —SO₂NR⁵R⁶, cyano, oxo, hydroxyl, C₁-C₄alkoxy, C₃-C₇cycloalkoxy, hydroxyC₁-C₄alkyl-, C₁-C₄alkoxyC₁-C₄alkyl-, —OCF₃, —NR⁵R⁶, R⁵R⁶NC₁-C₄alkyl-, —NR⁷C(O)C₁-C₄alkyl, —NR⁷CONR⁵R⁶, —NR⁷SO₂C₁-C₄alkyl, —NR⁷SO₂NR⁵R⁶, and R⁹, wherein when R⁸ is hydrogen R⁸ᵃ is not hydrogen or deuterium and wherein when R⁸ is deuterium R⁸ᵃ is not hydrogen or deuterium;

or R⁸ and R⁸ᵃ taken together with the carbon to which they are attached represent a 3- to 6-membered saturated ring optionally containing one or two heteroatoms selected from oxygen, nitrogen, and sulfur, which is optionally substituted 1 to 3 times by oxo, C₁-C₄alkyl, halogen, C₁-C₄alkylhydroxy, C₁-C₄alkoxy, or —NR⁵R⁶;

m is 0, 1, 2 or 3;

Y is C or N;

or a pharmaceutically acceptable salt thereof.

This invention also relates to pharmaceutical compositions, which comprise compounds of Formula (I) and pharmaceutically acceptable carriers.

This invention also relates to methods of treating cancer comprising administering an effective amount of a compound of Formula (I) to a human in need thereof.

This invention also relates to methods of treating cancer comprising co-administering an compound of Formula (I) and a second compound to a human in need thereof.

DETAILED DESCRIPTION OF THE INVENTION

This invention relates to compounds of Formula (I), and pharmaceutically acceptable salts thereof.

This invention also relates to compounds of Formula (I) (A):

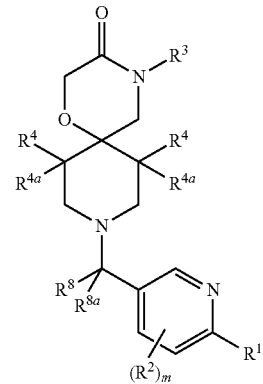

(I)(A)

or pharmaceutically acceptable salts thereof, wherein R¹, R², R³, R⁴, R⁴ᵃ, R⁵, R⁶, R⁷, R⁸, R⁸ᵃ and m are defined according to Formula (I).

This invention also relates to compounds of Formula (I) (B):

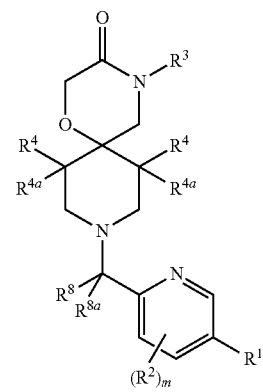

(I)(B)

or pharmaceutically acceptable salts thereof, wherein R¹, R², R³, R⁴, R⁴ᵃ, R⁵, R⁶, R⁷, R⁸, R⁸ᵃ and m are defined according to Formula (I).

This invention also relates to compounds of Formula (I) (C):

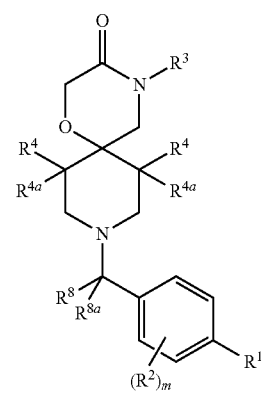

(I)(C)

or pharmaceutically acceptable salts thereof, wherein $R^1$, $R^2$, $R^3$, $R^4$, $R^{4a}$, $R^5$, $R^6$, $R^7$, $R^8$, $R^{8a}$ and m are defined according to Formula (I).

This invention also relates to compounds of Formula (I)(D):

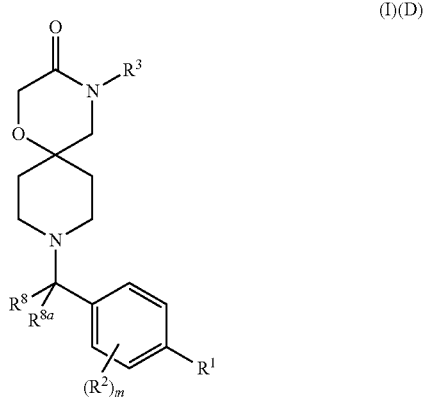

(I)(D)

wherein $R^1$ is phenyl, naphthyl, quinolyl, isoquinolyl wherein said phenyl, naphthyl, quinolyl, isoquinolyl is optionally substituted with from 1 to 3 substituents independently selected from:

optionally substituted $C_1$-$C_6$alkyl; —$CF_3$, $C_3$-$C_7$cycloalkyl, -cyano, oxo, hydroxyl, halogen, $C_1$-$C_4$alkoxy, hydroxy$C_1$-$C_4$alkyl-, $C_1$-$C_4$alkoxy$C_1$-$C_4$alkyl-, and —$OCF_3$;

each $R^2$ is selected from the group consisting of halogen, $C_1$-$C_6$alkyl, hydroxyl, cyano, and $C_1$-$C_4$alkoxy;

$R^3$ is selected from the group consisting of: $C_1$-$C_6$alkyl and $C_3$-$C_7$cycloalkyl, wherein $R^8$ and $R^{8a}$ are independently selected from hydrogen, deuterium, cyano, $C_1$-$C_4$alkyl, —$C_1$-$C_4$alkylhydroxy, $C_1$-$C_6$alkoxy, —$C_1$-$C_4$alkyl(=O)OH, —$C_1$-$C_4$alkyl(=O)O$C_1$-$C_4$alkyl, —$C_1$-$C_4$alkyl(=O)NR$^5$R$^6$, —$C_1$-$C_4$alkylNR$^5$R$^6$, —$C_1$-$C_4$alkylNR$^5$C(=O)$C_1$-$C_4$alkyl, —$C_1$-$C_4$alkylNR$^5$C(=O)NR$^5$R$^6$, $C_1$-$C_4$alkyl(=O)NR$^5$OR$^6$, and triazolyl, wherein when $R^8$ is hydrogen $R^{8a}$ is not hydrogen or deuterium and wherein when $R^8$ is deuterium $R^{8a}$ is not hydrogen or deuterium;

$R^5$ is selected from the group consisting of hydrogen and $C_1$-$C_4$alkyl;

$R^6$ is hydrogen and $C_1$-$C_4$alkyl, m is 0, 1, 2 or 3;

or a pharmaceutically acceptable salt thereof.

In one embodiment, this invention relates to compounds of Formula (I), (I)(A), (I)(B), (I)(C) wherein $R^1$ is phenyl optionally substituted with from 1 to 3 substituents independently selected from: optionally substituted $C_1$-$C_6$alkyl; —$CF_3$, $C_3$-$C_7$cycloalkyl, —C(=O)$C_1$-$C_4$alkyl, —$C_1$-$C_6$alkyl$C_3$-$C_7$cycloalkyl, —C(=O)$C_3$-$C_7$cycloalkyl, —C(=O)(phenyl), —C(=O)O$C_1$-$C_4$alkyl, —C(=O)OH, —C(=O)NR$^5$R$^6$, —O($C_1$-$C_4$alkyl)NR$^5$R$^6$, phenyl, —SO$_2$$C_1$-$C_4$alkyl, —SO$_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —OCF$_3$, —NR$^5$R$^6$, R$^5$R$^6$N$C_1$-$C_4$alkyl-, —NR$^7$C(=O)$C_1$-$C_4$alkyl, —NR$^7$C(=O)NR$^5$R$^6$, —NR$^7$SO$_2$$C_1$-$C_4$alkyl, —NR$^7$SO$_2$NR$^5$R$^6$ and R$^9$, or pharmaceutically acceptable salts thereof.

In another embodiment, this invention also relates to compounds of Formula (I), (I)(A), (I)(B), or (I)(C) wherein $R^1$ is selected from furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, and triazinyl all of which are optionally substituted with from 1 to 3 substituents independently selected from: optionally substituted $C_1$-$C_6$alkyl; —CF$_3$, $C_3$-$C_7$cycloalkyl, —C(=O)$C_1$-$C_4$alkyl, —$C_1$-$C_6$alkyl$C_3$-$C_7$cycloalkyl, —C(=O)$C_3$-$C_7$cycloalkyl, —C(=O)(phenyl), —C(=O)O$C_1$-$C_4$alkyl, —C(=O)OH, —C(=O)NR$^5$R$^6$, —O($C_1$-$C_4$alkyl)NR$^5$R$^6$, phenyl, —SO$_2$$C_1$-$C_4$alkyl, —SO$_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —OCF$_3$, —NR$^5$R$^6$, R$^5$R$^6$NC$_1$-$C_4$alkyl-, —NR$^7$C(=O)$C_1$-$C_4$alkyl, —NR$^7$C(=O)NR$^5$R$^6$, —NR$^7$SO$_2$$C_1$-$C_4$alkyl, —NR$^7$SO$_2$NR$^5$R$^6$ and R$^9$, or pharmaceutically acceptable salts thereof.

In another embodiment, this invention also relates to compounds of Formula (I), (I)(A), (I)(B), or (I)(C) wherein $R^1$ is naphthyl optionally substituted with from 1 to 3 substituents independently selected from: optionally substituted $C_1$-$C_6$alkyl; —CF$_3$, $C_3$-$C_7$cycloalkyl, —C(=O)$C_1$-$C_4$alkyl, —$C_1$-$C_6$alkyl$C_3$-$C_7$cycloalkyl, —C(=O)$C_3$-$C_7$cycloalkyl, —C(=O)(phenyl), —C(=O)O$C_1$-$C_4$alkyl, —C(=O)OH, —C(=O)NR$^5$R$^6$, —O($C_1$-$C_4$alkyl)NR$^5$R$^6$, phenyl, —SO$_2$$C_1$-$C_4$alkyl, —SO$_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —OCF$_3$, —NR$^5$R$^6$, R$^5$R$^6$NC$_1$-$C_4$alkyl-, —NR$^7$C(=O)$C_1$-$C_4$alkyl, —NR$^7$C(=O)NR$^5$R$^6$, —NR$^7$SO$_2$$C_1$-$C_4$alkyl, —NR$^7$SO$_2$NR$^5$R$^6$ and R$^9$ or pharmaceutically acceptable salts thereof.

In another embodiment, this invention also relates to compounds of Formula (I), (I)(A), (I)(B), or (I)(C) wherein $R^1$ is selected from benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, 1-H-indazolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, or pteridinyl, wherein said benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, 1-H-indazolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl all of which are optionally substituted with from 1 to 3 substituents independently selected from: optionally substituted $C_1$-$C_6$alkyl; —CF$_3$, C$_3$-C$_7$cycloalkyl, —C(=O)C$_1$-C$_4$alkyl, —C$_1$-C$_6$alkylC$_3$-C$_7$cycloalkyl, —C(=O)C$_3$-C$_7$cycloalkyl, —C(=O)(phenyl), —C(=O)OC$_1$-C$_4$alkyl, —C(=O)OH, —C(=O)NR$^5$R$^6$, —O(C$_1$-C$_4$alkyl)NR$^5$R$^6$, phenyl, —SO$_2$C$_1$-C$_4$alkyl, —SO$_2$NR$^5$R$^6$, cyano, oxo, hydroxyl, halogen, C$_1$-C$_4$alkoxy, C$_3$-C$_7$cycloalkylC$_1$-C$_4$alkoxy, hydroxyC$_1$-C$_4$alkyl-, C$_1$-C$_4$alkoxyC$_1$-C$_4$alkyl-, —OCF$_3$, —NR$^5$R$^6$, R$^5$R$^6$NC$_1$-C$_4$alkyl-, —NR$^7$C(=O)C$_1$-C$_4$alkyl, —NR$^7$C(=O)NR$^5$R$^6$, —NR$^7$SO$_2$C$_1$-C$_4$alkyl, —NR$^7$SO$_2$NR$^5$R$^6$ and R$^9$ or pharmaceutically acceptable salts thereof.

In another embodiment, this invention also relates to compounds of Formula (I), (I)(A), (I)(B), or (I)(C) wherein R$^1$ is selected from phenyl and optionally substituted quinolinyl or pharmaceutically acceptable salts thereof.

In another embodiment, this invention also relates to compounds of any of the above embodiments, wherein each R$^2$ is absent or is fluoro, hydroxyl, methyl, or methoxy or pharmaceutically acceptable salts thereof.

In another embodiment, this invention also relates to compounds of any of the above embodiments, wherein R$^3$ is selected from ethyl, isopropyl, 1-methylcyclopropyl, 1-hydroxymethylcyclopropyl, and cyclopropyl or pharmaceutically acceptable salts thereof.

In another embodiment, this invention also relates to compounds of any of the above embodiments, wherein each R$^4$ and R$^{4a}$ independently selected from hydrogen, oxo, halogen or C$_1$-C$_6$alkyl, or pharmaceutically acceptable salts thereof.

The invention also provides compounds of Formula (I) wherein:

R$^1$ is selected from the group of: phenyl, indolyl, benzofuranyl, indazolyl, benzoimidazolinyl, naphthalyl, quinolyl, and wherein said phenyl, indolyl, benzofuranyl, indazolyl, benzoimidazolinyl, naphthalyl, quinolyl is optionally substituted with from 1 to 3 substituents independently selected from: C$_1$-C$_4$, methyloxy, cyano, NR$^5$R$^6$ and halogen, each R$^2$ is selected from the group consisting of halogen, C$_1$-C$_6$alkyl, hydroxyl, and C$_1$-C$_4$alkoxy;

R$^3$ is selected from the group consisting of C$_1$-C$_6$alkyl and cyclopropyl; and each R$^4$ and R$^{4a}$ is independently selected from hydrogen, oxo, halogen or C$_1$-C$_6$alkyl;

each R$^8$ and R$^{8a}$ is independently selected from hydrogen, deuterium, cyano, optionally substituted C$_1$-C$_4$alkyl, —C$_1$-C$_4$hydroxy, C$_1$-C$_6$alkoxy-C$_1$-C$_4$(=O)OH, —C$_1$-C$_4$(=O)OC$_1$-C$_4$, —C$_1$-C$_4$(=O)NR$^5$R$^6$, —C$_1$-C$_4$NR$^5$R$^6$, triazolyl, and R$^9$ wherein any optionally substituted C$_1$-C$_4$alkyl and C$_1$-C$_6$alkoxy moiety is optionally substituted with from 1 to 6 substituents independently selected from the group of: halogen, C$_1$-C$_4$alkyl, —CF$_3$, C$_3$-C$_7$cycloalkyl, —C(O)C$_1$-C$_4$alkyl, —C(O)C$_3$-C$_7$cycloalkyl, —CO(phenyl), carboxyl, —CO$_2$C$_1$-C$_4$alkyl, —CONR$^5$R$^6$, phenyl, 5- or 6-membered heteroaryl, —SO$_2$C$_1$-C$_4$alkyl, —SO$_2$NR$^5$R$^6$, cyano, oxo, hydroxyl, C$_1$-C$_4$alkoxy, C$_3$-C$_7$cycloalkoxy, hydroxyC$_1$-C$_4$alkyl-, C$_1$-C$_4$alkoxyC$_1$-C$_4$alkyl-, —OCF$_3$, —NR$^5$R$^6$, R$^5$R$^6$NC$_1$-C$_4$alkyl-, —NHC(O)C$_1$-C$_4$alkyl, —NR$^6$CONR$^5$R$^6$, —NR$^6$SO$_2$C$_1$-C$_4$alkyl, —NR$^6$SO$_2$NR$^5$R$^6$, and R$^9$, wherein when R$^8$ is hydrogen R$^{8a}$ is not hydrogen or deuterium and wherein when R$^8$ is deuterium R$^{8a}$ is not hydrogen or deuterium;

m is 0, 1, 2 or 3;

Y is C or N;

or a pharmaceutically acceptable salt thereof;

This invention also relates to the following compounds of Formula (I):

2-(4-cyclopropyl-3-oxo-1-oxa-4,9-diazaspiro[5.5]undecan-9-yl)-2-(4-(quinolin-7-yl)phenyl)acetic acid;

2-(4-cyclopropyl-3-oxo-1-oxa-4,9-diazaspiro[5.5]undecan-9-yl)-2-(4-(quinolin-7-yl)phenyl)acetamide;

2-(4-cyclopropyl-3-oxo-1-oxa-4,9-diazaspiro[5.5]undecan-9-yl)-N,N-dimethyl-2-(4-(quinolin-7-yl)phenyl)acetamide;

2-(4-cyclopropyl-3-oxo-1-oxa-4,9-diazaspiro[5.5]undecan-9-yl)-N-methyl-2-(4-(quinolin-7-yl)phenyl)acetamide;

methyl 3-(4-cyclopropyl-3-oxo-1-oxa-4,9-diazaspiro[5.5]undecan-9-yl)-3-(4-(quinolin-7-yl)phenyl)propanoate;

3-(4-cyclopropyl-3-oxo-1-oxa-4,9-diazaspiro[5.5]undecan-9-yl)-3-(4-(quinolin-7-yl)phenyl)propanoic acid;

(−)-3-(4-cyclopropyl-3-oxo-1-oxa-4,9-diazaspiro[5.5]undecan-9-yl)-3-(4-(quinolin-7-yl)phenyl)propanamide;

(+)-3-(4-cyclopropyl-3-oxo-1-oxa-4,9-diazaspiro[5.5]undecan-9-yl)-3-(4-(quinolin-7-yl)phenyl)propanamide;

(+)-2-(4-cyclopropyl-3-oxo-1-oxa-4,9-diazaspiro[5.5]undec-9-yl)-2-[2-fluoro-4-(7-quinolinyl)phenyl]acetamide;

(−)-2-(4-cyclopropyl-3-oxo-1-oxa-4,9-diazaspiro[5.5]undec-9-yl)-2-[2-fluoro-4-(7-quinolinyl)phenyl]acetamide;

(+)-2-(4-cyclopropyl-3-oxo-1-oxa-4,9-diazaspiro[5.5]undecan-9-yl)-2-(2-fluoro-4-(3-methylquinolin-7-yl)phenyl)acetamide;

(−)-2-(4-cyclopropyl-3-oxo-1-oxa-4,9-diazaspiro[5.5]undecan-9-yl)-2-(2-fluoro-4-(3-methylquinolin-7-yl)phenyl)acetamide;

4-cyclopropyl-9-(1-(4-(quinolin-7-yl)phenyl)ethyl)-1-oxa-4,9-diazaspiro[5.5]undecan-3-one;

4-cyclopropyl-9-(1-(3-fluoro-4'-methoxy-[1,1'-biphenyl]-4-yl)ethyl)-1-oxa-4,9-diazaspiro[5.5]undecan-3-one;

(+)-4-cyclopropyl-9-(1-(2-fluoro-4-(quinolin-7-yl)phenyl)ethyl)-1-oxa-4,9-diazaspiro[5.5]undecan-3-one;

(−)-4-cyclopropyl-9-(1-(2-fluoro-4-(quinolin-7-yl)phenyl)ethyl)-1-oxa-4,9-diazaspiro[5.5]undecan-3-one;

2-(4-cyclopropyl-3-oxo-1-oxa-4,9-diazaspiro[5.5]undecan-9-yl)-2-(4-(quinolin-7-yl)phenyl)acetonitrile;

2-(4-cyclopropyl-3-oxo-1-oxa-4,9-diazaspiro[5.5]undecan-9-yl)-2-(2-fluoro-4-(quinolin-7-yl)phenyl)acetic acid;

(−)-2-(4-cyclopropyl-3-oxo-1-oxa-4,9-diazaspiro[5.5]undecan-9-yl)-2-(4-(quinolin-7-yl)phenyl)acetamide;

(+)-2-(4-cyclopropyl-3-oxo-1-oxa-4,9-diazaspiro[5.5]undecan-9-yl)-2-(4-(quinolin-7-yl)phenyl)acetamide;

2-(4-cyclopropyl-3-oxo-1-oxa-4,9-diazaspiro[5.5]undecan-9-yl)-2-(2-fluoro-4-(quinolin-7-yl)phenyl)acetamide;

4-cyclopropyl-9-(2-hydroxy-1-(4-(quinolin-7-yl)phenyl)ethyl)-1-oxa-4,9-diazaspiro[5.5]undecan-3-one;

methyl 3-(4-cyclopropyl-3-oxo-1-oxa-4,9-diazaspiro[5.5]undecan-9-yl)-3-(2-fluoro-4-(quinolin-7-yl)phenyl)propanoate;

4-cyclopropyl-9-(2-oxo-1-(4-(quinolin-7-yl)phenyl)propyl)-1-oxa-4,9-diazaspiro[5.5]undecan-3-one;

(+)-4-cyclopropyl-9-(1-(2-fluoro-4-(quinolin-7-yl)phenyl)-2-hydroxyethyl)-1-oxa-4,9-diazaspiro[5.5]undecan-3-one;

(−)-4-cyclopropyl-9-(1-(2-fluoro-4-(quinolin-7-yl)phenyl)-2-hydroxyethyl)-1-oxa-4,9-diazaspiro[5.5]undecan-3-one;

(+)-2-(4-cyclopropyl-3-oxo-1-oxa-4,9-diazaspiro[5.5]undecan-9-yl)-2-(2-fluoro-4-(quinolin-7-yl)phenyl)-N-methylacetamide;

(−)-2-(4-cyclopropyl-3-oxo-1-oxa-4,9-diazaspiro[5.5]undecan-9-yl)-2-(2-fluoro-4-(quinolin-7-yl)phenyl)-N-methylacetamide;

(+)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide;

(−)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide;

(+)-2-(4-cyclopropyl-3-oxo-1-oxa-4,9-diazaspiro[5.5]undecan-9-yl)-2-(2-fluoro-4-(2-methylquinolin-7-yl)phenyl)acetamide;

(−)-2-(4-cyclopropyl-3-oxo-1-oxa-4,9-diazaspiro[5.5]undecan-9-yl)-2-(2-fluoro-4-(2-methylquinolin-7-yl)phenyl)acetamide;

2-(4-cyclopropyl-3-oxo-1-oxa-4,9-diazaspiro[5.5]undecan-9-yl)-2-(3-fluoro-4'-methoxy-[1,1'-biphenyl]-4-yl)acetamide;

2-(4-cyclopropyl-3-oxo-1-oxa-4,9-diazaspiro[5.5]undecan-9-yl)-2-(2-fluoro-4-(2-hydroxyquinolin-7-yl)phenyl)acetamide;

2-(4-cyclopropyl-3-oxo-1-oxa-4,9-diazaspiro[5.5]undecan-9-yl)-2-(3,4'-difluoro-[1,1'-biphenyl]-4-yl)acetamide;

(+)-2-(4-cyclopropyl-3-oxo-1-oxa-4,9-diazaspiro[5.5]undecan-9-yl)-2-(2-fluoro-4-(quinolin-7-yl)phenyl)-N-hydroxyacetamide;

(−)-2-(4-cyclopropyl-3-oxo-1-oxa-4,9-diazaspiro[5.5]undecan-9-yl)-2-(2-fluoro-4-(quinolin-7-yl)phenyl)-N-hydroxyacetamide;

(+)-4-cyclopropyl-9-(1-(2,6-difluoro-4-(quinolin-7-yl)phenyl)-2-hydroxyethyl)-1-oxa-4,9-diazaspiro[5.5]undecan-3-one;

(−)-4-cyclopropyl-9-(1-(2,6-difluoro-4-(quinolin-7-yl)phenyl)-2-hydroxyethyl)-1-oxa-4,9-diazaspiro[5.5]undecan-3-one;

(+)-2-(4-cyclopropyl-3-oxo-1-oxa-4,9-diazaspiro[5.5]undecan-9-yl)-2-(2-fluoro-4-(quinolin-5-yl)phenyl)acetamide;

(−)-2-(4-cyclopropyl-3-oxo-1-oxa-4,9-diazaspiro[5.5]undecan-9-yl)-2-(2-fluoro-4-(quinolin-5-yl)phenyl)acetamide;

(−)-2-(4-cyclopropyl-3-oxo-1-oxa-4,9-diazaspiro[5.5]undecan-9-yl)-2-(2-fluoro-4-(quinolin-7-yl)phenyl)-N,N-dimethylacetamide;

(+)-2-(4-cyclopropyl-3-oxo-1-oxa-4,9-diazaspiro[5.5]undecan-9-yl)-2-(2-fluoro-4-(quinolin-7-yl)phenyl)-N,N-dimethylacetamide;

(+)-2-(4-cyclopropyl-3-oxo-1-oxa-4,9-diazaspiro[5.5]undecan-9-yl)-2-(2-fluoro-4-(2-methylquinolin-5-yl)phenyl)acetamide;

(−)-2-(4-cyclopropyl-3-oxo-1-oxa-4,9-diazaspiro[5.5]undecan-9-yl)-2-(2-fluoro-4-(2-methylquinolin-5-yl)phenyl)acetamide;

(+)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate;

(−)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate;

(+)-2-(4-cyclopropyl-3-oxo-1-oxa-4,9-diazaspiro[5.5]undecan-9-yl)-2-(2-fluoro-4-(2-hydroxyquinolin-7-yl)phenyl)acetamide;

(−)-2-(4-cyclopropyl-3-oxo-1-oxa-4,9-diazaspiro[5.5]undecan-9-yl)-2-(2-fluoro-4-(2-hydroxyquinolin-7-yl)phenyl)acetamide;

(+)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide;

(−)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide;

(+)-2-(4-ethyl-3-oxo-1-oxa-4,9-diazaspiro[5.5]undecan-9-yl)-2-(2-fluoro-4-(8-fluoroquinolin-7-yl)phenyl)acetamide;

(−)-2-(4-ethyl-3-oxo-1-oxa-4,9-diazaspiro[5.5]undecan-9-yl)-2-(2-fluoro-4-(8-fluoroquinolin-7-yl)phenyl)acetamide;

(+)-2-(4-ethyl-3-oxo-1-oxa-4,9-diazaspiro[5.5]undecan-9-yl)-2-(2-fluoro-4-(8-methoxyquinolin-7-yl)phenyl)acetamide;

(−)-2-(4-ethyl-3-oxo-1-oxa-4,9-diazaspiro[5.5]undecan-9-yl)-2-(2-fluoro-4-(8-methoxyquinolin-7-yl)phenyl)acetamide;

2-(4-cyclopropyl-3-oxo-1-oxa-4,9-diazaspiro[5.5]undecan-9-yl)-2-(2,6-difluoro-4-(quinolin-7-yl)phenyl)acetamide;

ethyl 2-(4-ethyl-3-oxo-1-oxa-4,9-diazaspiro[5.5]undecan-9-yl)-2-(2-fluoro-4-(quinolin-7-yl)phenyl)acetate;

(+)-2-(4-ethyl-3-oxo-1-oxa-4,9-diazaspiro[5.5]undecan-9-yl)-2-(2-fluoro-4-(quinolin-7-yl)phenyl)acetamide;

(−)-2-(4-ethyl-3-oxo-1-oxa-4,9-diazaspiro[5.5]undecan-9-yl)-2-(2-fluoro-4-(quinolin-7-yl)phenyl)acetamide;

(+)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide;

(−)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide;

2-(4-(3-cyanoquinolin-7-yl)-2-fluorophenyl)-2-(4-cyclopropyl-3-oxo-1-oxa-4,9-diazaspiro[5.5]undecan-9-yl)acetamide;

(+)-2-(4-(3-cyanoquinolin-7-yl)-2-fluorophenyl)-2-(4-cyclopropyl-3-oxo-1-oxa-4,9-diazaspiro[5.5]undecan-9-yl)acetamide;

(−)-2-(4-(3-cyanoquinolin-7-yl)-2-fluorophenyl)-2-(4-cyclopropyl-3-oxo-1-oxa-4,9-diazaspiro[5.5]undecan-9-yl)acetamide;

(+)-2-(4-(3-chloroquinolin-7-yl)-2-fluorophenyl)-2-(4-cyclopropyl-3-oxo-1-oxa-4,9-diazaspiro[5.5]undecan-9-yl)acetamide;

(−)-2-(4-(3-chloroquinolin-7-yl)-2-fluorophenyl)-2-(4-cyclopropyl-3-oxo-1-oxa-4,9-diazaspiro[5.5]undecan-9-yl)acetamide;

2-(4-cyclopropyl-3-oxo-1-oxa-4,9-diazaspiro[5.5]undecan-9-yl)-2-(2-fluoro-4-(8-fluoroquinolin-7-yl)phenyl)acetamide;

(+)-2-(4-cyclopropyl-3-oxo-1-oxa-4,9-diazaspiro[5.5]undecan-9-yl)-2-(2-fluoro-4-(8-fluoroquinolin-7-yl)phenyl)acetamide;

(−)-2-(4-cyclopropyl-3-oxo-1-oxa-4,9-diazaspiro[5.5]undecan-9-yl)-2-(2-fluoro-4-(8-fluoroquinolin-7-yl)phenyl)acetamide;

2-(2,6-difluoro-4-(quinolin-7-yl)phenyl)-2-(4-ethyl-3-oxo-1-oxa-4,9-diazaspiro[5.5]undecan-9-yl)acetamide;

(+)-2-(2,6-difluoro-4-(quinolin-7-yl)phenyl)-2-(4-ethyl-3-oxo-1-oxa-4,9-diazaspiro[5.5]undecan-9-yl)acetamide;

(−)-2-(2,6-difluoro-4-(quinolin-7-yl)phenyl)-2-(4-ethyl-3-oxo-1-oxa-4,9-diazaspiro[5.5]undecan-9-yl)acetamide;

(+)-2-(4-cyclopropyl-3-oxo-1-oxa-4,9-diazaspiro[5.5]undecan-9-yl)-2-(2,6-difluoro-4-(quinolin-7-yl)phenyl)acetamide;

(−)-2-(4-cyclopropyl-3-oxo-1-oxa-4,9-diazaspiro[5.5]undecan-9-yl)-2-(2,6-difluoro-4-(quinolin-7-yl)phenyl)acetamide;

(+)-2-(4-cyclopropyl-3-oxo-1-oxa-4,9-diazaspiro[5.5]undecan-9-yl)-2-(2-fluoro-4-(3-methoxyquinolin-7-yl)phenyl)acetamide;

(−)-2-(4-cyclopropyl-3-oxo-1-oxa-4,9-diazaspiro[5.5]undecan-9-yl)-2-(2-fluoro-4-(3-methoxyquinolin-7-yl)phenyl)acetamide;

(+)-2-(4-cyclopropyl-3-oxo-1-oxa-4,9-diazaspiro[5.5]undecan-9-yl)-2-(2-fluoro-4-(8-methoxyquinolin-7-yl)phenyl)acetamide;
(−)-2-(4-cyclopropyl-3-oxo-1-oxa-4,9-diazaspiro[5.5]undecan-9-yl)-2-(2-fluoro-4-(8-methoxyquinolin-7-yl)phenyl)acetamide;
4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one;
(+)-4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one;
(−)-4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one;
2-(4-(3-cyanoquinolin-7-yl)-2-fluorophenyl)-2-(4-ethyl-3-oxo-1-oxa-4,9-diazaspiro[5.5]undecan-9-yl)acetamide;
(+)-2-(4-(3-cyanoquinolin-7-yl)-2-fluorophenyl)-2-(4-ethyl-3-oxo-1-oxa-4,9-diazaspiro[5.5]undecan-9-yl)acetamide;
(−)-2-(4-(3-cyanoquinolin-7-yl)-2-fluorophenyl)-2-(4-ethyl-3-oxo-1-oxa-4,9-diazaspiro[5.5]undecan-9-yl)acetamide;
2-(4-ethyl-3-oxo-1-oxa-4,9-diazaspiro[5.5]undecan-9-yl)-2-(2-fluoro-4-(3-methylquinolin-7-yl)phenyl)acetamide;
(+)-2-(4-ethyl-3-oxo-1-oxa-4,9-diazaspiro[5.5]undecan-9-yl)-2-(2-fluoro-4-(3-methylquinolin-7-yl)phenyl)acetamide;
(−)-2-(4-ethyl-3-oxo-1-oxa-4,9-diazaspiro[5.5]undecan-9-yl)-2-(2-fluoro-4-(3-methylquinolin-7-yl)phenyl)acetamide;
(+)-2-(4-(3-chloroquinolin-7-yl)-2-fluorophenyl)-2-(4-ethyl-3-oxo-1-oxa-4,9-diazaspiro[5.5]undecan-9-yl)acetamide;
(−)-2-(4-(3-chloroquinolin-7-yl)-2-fluorophenyl)-2-(4-ethyl-3-oxo-1-oxa-4,9-diazaspiro[5.5]undecan-9-yl)acetamide;
(+)-2-(4-ethyl-3-oxo-1-oxa-4,9-diazaspiro[5.5]undecan-9-yl)-2-(2-fluoro-4-(3-fluoroquinolin-7-yl)phenyl)acetamide;
(−)-2-(4-ethyl-3-oxo-1-oxa-4,9-diazaspiro[5.5]undecan-9-yl)-2-(2-fluoro-4-(3-fluoroquinolin-7-yl)phenyl)acetamide;
(+)-2-(4-ethyl-3-oxo-1-oxa-4,9-diazaspiro[5.5]undecan-9-yl)-2-(2-fluoro-4-(3-methoxyquinolin-7-yl)phenyl)acetamide; and
(−)-2-(4-ethyl-3-oxo-1-oxa-4,9-diazaspiro[5.5]undecan-9-yl)-2-(2-fluoro-4-(3-methoxyquinolin-7-yl)phenyl)acetamide
and pharmaceutically acceptable salts thereof.

In one embodiment, a compound of the invention has an enantiomeric excess of one enantiomer over the other. In one embodiment, a compound of the invention is an enantiomerically pure R isomer. In one embodiment, a compound of the invention is an enantiomerically pure S isomer.

In one embodiment, pharmaceutical compositions are provided comprising a compound of Formula (I) or a pharmaceutically acceptable salt thereof and a pharmaceutically acceptable carrier. In one embodiment, the invention provides the use of an effective amount of a compound of Formula (I) or a pharmaceutically acceptable salt thereof for the treatment of cancer. In one embodiment, the invention provides the use of Formula (I) of a pharmaceutically acceptable salt thereof for the manufacture of a medicament for treating cancer.

In another embodiment, methods are provided for treating cancer comprising administering to a human in need thereof an effective amount of a compound of Formula (I) or a pharmaceutically acceptable salt thereof. In one embodiment, the cancer is selected from the group consisting of: gastric, brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid.

In another embodiment, methods are provided of treating cancer in a mammal in need thereof comprising: administering to such mammal a therapeutically effective amount of
a) a compound of Formula (I) or a pharmaceutically acceptable salt thereof; and
b) at least one anti-neoplastic agent.

This invention also relates to compounds exemplified in the Experimental section. Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids. More specific examples of suitable acid salts include maleic, hydrochloric, hydrobromic, sulphuric, phosphoric, nitric, perchloric, fumic, fumaric, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, triethiodide, and valerate salts.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compound or salt represented by Formula (I) as mixtures with isomers thereof in which one or more chiral centers are inverted. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compound represented by Formula (I), as well as any wholly or partially equilibrated mixtures thereof. The present invention also includes the individual isomers of the compound or salt represented by the Formula (I) as well as mixtures with isomers thereof in which one or more chiral centers are inverted. It is to be understood that the present invention includes all combinations and subsets of the particular groups defined hereinabove.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). Commercially available deuterated starting materials may be employed in the preparation of deuterated forms of the compounds of Formula (I), or they may be synthesized using conventional techniques employing deuterated reagents (e.g. lithium aluminum deuteride).

DEFINITIONS

Terms are used within their accepted meanings. The following definitions are meant to clarify, but not limit, the terms defined.

As used herein, the term "alkyl" refers to a straight or branched chain hydrocarbon radical, preferably having from one to twelve carbon atoms, which may be unsubstituted or substituted, saturated or unsaturated with multiple degrees of substitution included within the present invention. When optionally substituted, the alkyl group is unsubstituted or substituted with suitable substituents selected from the group consisting of halogen, amino, substituted amino, cyano, hydroxyl, alkoxy, alkylthio, alkylsulfonyl, aminosulfonyl, carboxylic acid, carboxylic ester, carboxamide, aminocarbonyl, and heterocyclyl. Examples of "alkyl" as used herein include, but are not limited to, methyl, ethyl, propyl, isopropyl, isobutyl, n-butyl, t-butyl, isopentyl, n-pentyl, and the like, as well as substituted versions thereof.

As used herein, the term "cycloalkyl" refers to an unsubstituted or substituted mono- or polycyclic non-aromatic saturated ring. Exemplary "cycloalkyl" groups include, but are not limited to, cyclopropyl, cyclobutyl, cyclopentyl, cyclohexyl, cycloheptyl, and the like, as well as unsubstituted and substituted versions thereof.

As used herein, the term "alkoxy" refers to the group —$OR^a$, where $R^a$ is $C_1$-$C_4$alkyl or $C_3$-$C_7$cycloalkyl as defined above. The term "$C_1$-$C_4$alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, and t-butoxy.

"Heterocycloalkyl" represents a group or moiety comprising a non-aromatic, monovalent monocyclic or bicyclic radical, which is saturated or partially unsaturated, containing 3 to 10 ring atoms, which includes 1 to 3 heteroatoms independently selected from nitrogen, oxygen and sulfur. Illustrative examples of heterocycloalkyls useful in the present invention include, but are not limited to, azetidinyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl and 1,5,9-triazacyclododecyl.

As used herein, the term "heterocyclyl" refers to an unsubstituted or substituted mono- or polycyclic ring system containing one or more heteroatoms. Preferred heteroatoms include nitrogen, oxygen, and sulfur, including N-oxides, sulfur oxides, and dioxides. A heterocyclic ring may be, but is not limited to, three to eight-membered and is either fully saturated or has one or more degrees of unsaturation. Multiple degrees of substitution are included within the present definition. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers, as well as unsubstituted and substituted versions thereof. The term "9- or 10-membered heterocyclyl" represents a fully unsaturated or partially unsaturated, bicyclic group, containing 9 or 10 ring atoms, including 1 to 5 heteroatoms independently selected from nitrogen, oxygen and sulfur, which group may be unsubstituted or substituted by one or more of the substituents defined herein. Selected 9- or 10-membered heterocycyl groups contain one nitrogen, oxygen or sulfur ring heteroatom, and optionally contain 1, 2, 3, or 4 additional nitrogen ring atoms and/or 1 additional oxygen or sulfur atom. Examples of 9- or 10-membered heterocyclyl groups include, but are not limited to, benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

The term "aryl" refers to a carbocyclic aromatic moiety (such as phenyl or naphthyl) containing the specified number of carbon atoms, particularly from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl.

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 8 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary 5- to 6-membered heteroaryls include, but are not limited to, furanyl, thiophenyl, thienyl, pyrrolyl, imidazolyl, pyrazolyl, triazolyl, tetrazolyl, thiazolyl, isothiazolyl, 1,2,3-triazolyl, 1,2,4-traizolyl, oxazolyl, isoxazolyl, 1,2,3-oxadiazolyl, 1,2,5-oxadiazolyl, thiadiazolyl, isothiazolyl, tetrazolyl, pyridinyl, pyridazinyl, pyrazinyl, pyrimidinyl, and triazinyl. Other exemplary heteroaryl groups include, but are not limited to benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Suitable substituents for heteroaryl are described in the definition of "optionally substituted."

As used herein "heterocyclic," "heterocycle," "heterocycl" groups or grammatical variations thereof include "heteroaryl" and "heterocycloalkyl" groups.

As used herein, the term "cyano" refers to the group —CN.

As used herein, the term "optionally" means that the subsequently described event(s) may or may not occur, and includes both event(s) that occur and event(s) that do not occur.

As used herein, unless otherwise defined, the phrase "optionally substituted" or grammatical variations thereof denote an optional substitution, including multiple degrees of substitution, with one or more substitutent group. The phrase should not be interpreted as duplicative of the substitutions herein described and depicted. Exemplary optional substituent groups include acyl, alkyl, alkylsulfonyl, alkoxy, alkoxycarbonyl, cyano, halogen, haloalkyl, hydroxyl, oxo, amide, sulfamide, urea, amino, substituted amino, acylamino, phenylcarbonyl, dialkylaminosulfonamide, morpholino, sulfonamide, thiourea, nitro, pyrrolidinyl, pyrazolyl, pyrrolyl, phenyl, and tetrazolyl, wherein pyrrolidinyl, pyrazolyl and tetrazolyl can be further substituted with one to three $C_1$-$C_3$alkyl.

"Enantiomerically enriched" refers to products whose enantiomeric excess is greater than zero. For example, enantiomerically enriched refers to products whose enantiomeric excess is greater than about 50% ee, greater than about 75% ee, and greater than about 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 100% ee.

"Diastereomer" refers to a compound having at least two chiral centers.

"Diastereomer excess" or "de" is the excess of one diasteriomer over the others expressed as a percentage.

"Diasteriomerically pure" refers to products whose diasteriomeric excess is 100% de.

"Half-life" (or "half-lives") refers to the time required for half of a quantity of a substance to be converted to another chemically distinct specie in vitro or in vivo.

"Halo" or "halogen" refers to fluoro, chloro, bromo, or iodo.

"Heteroatom" refers to a nitrogen, sulphur, or oxygen atom.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Oxo" refers to the substituent group=O.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Compounds within the invention may occur in two or more tautometric forms; all such tautomeric forms are included within the scope of the invention.

The invention further provides a pharmaceutical composition (also referred to as pharmaceutical formulation) comprising a compound of Formula (I) or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula (I) or salt thereof with at least one excipient.

Pharmaceutical Compositions

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a method of treatment in a mammal, especially a human, with at least one disease condition targeted by the present compounds. Such treatment comprises the step of administering a therapeutically effective amount of a compound of Formula (I) or salt thereof to said mammal, particularly a human. Treatment can also comprise the step of administering a therapeutically effective amount of a pharmaceutical composition containing a compound of Formula (I) or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

While it is possible that, for use in therapy, a therapeutically effective amount of a compound of Formula (I) or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I) or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I) per se. Similar dosages should be appropriate for treatment (including prophylaxis) of the other conditions referred herein for treatment. In general, determination of appropriate dosing can be readily arrived at by one skilled in medicine or the pharmacy art.

Combinations

When a compound of Formula (I) is administered for the treatment of cancer, the term "co-administering" and derivatives thereof as used herein is meant either simultaneous administration or any manner of separate sequential administration of a FAS inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors. A non-limiting list of anti-neoplastic agents are provided herein.

Examples of a further active ingredient or ingredients for use in combination or co-administered with the present FAS inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate (2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

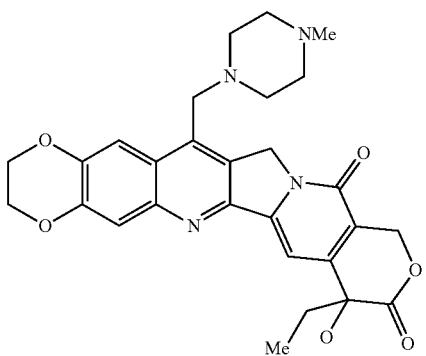

A known by the chemical name 7-(4-methylpiperazino-methylene)-10,11-ethylenedioxy-20(R,S)-camptothecin (racemic mixture) or 7-(4-methylpiperazino-methylene)-10,11-ethylenedioxy-20(R)-camptothecin (R enantiomer) or 7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrozole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast cancer and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Letrozole (trade name Femara) is an oral non-steroidal aromatase inhibitor for the treatment of hormonally-responsive breast cancer after surgery. Estrogens are produced by the conversion of androgens through the activity of the aromatase enzyme. Estrogens then bind to an estrogen receptor, which causes cells to divide. Letrozole prevents the aromatase from producing estrogens by competitive, reversible binding to the heme of its cytochrome P450 unit. The action is specific, and letrozole does not reduce production of mineralo- or corticosteroids.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta) IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and Bennett, C. F. and Cowsert, L. M. BioChim. Biophys. Acta, (1999) 1489(1):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Pazopanib which commercially available as VOTRIENT® is a tyrosine kinase inhibitor (TKI). Pazopanib is presented as the hydrochloride salt, with the chemical name 5-[[4-[(2,3-dimethyl-2H-indazol-6-yl)methylamino]-2-pyrimidinyl] amino]-2-methylbenzenesulfonamide monohydrochloride. Pazoponib is approved for treatment of patients with advanced renal cell carcinoma.

Bevacisumab which is commercially available as AVASTIN® is a humanized monoclonal antibody that blocks VEGF-A. AVASTIN® is approved form the treatment of various cancers including colorectal, lung, breast, kidney, and glioblastomas.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia CLL; a type of cancer of the white blood cells) in adults who are refractory to treatment with fludarabine (Fludara) and alemtuzumab Campath).

Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

mTOR inhibitors include but are not limited to rapamycin (FK506) and rapalogs, RAD001 or everolimus (Afinitor), CCI-779 or temsirolimus, AP23573, AZD8055, WYE-354, WYE-600, WYE-687 and Pp121.

Everolimus is sold as Afinitor® by Novartis and is the 40-O-(2-hydroxyethyl) derivative of sirolimus and works similarly to sirolimus as an mTOR (mammalian target of rapamycin) inhibitor. It is currently used as an immunosuppressant to prevent rejection of organ transplants and treatment of renal cell cancer. Much research has also been conducted on everolimus and other mTOR inhibitors for use in a number of cancers. It has the following chemical structure (formula II) and chemical name:

(II)

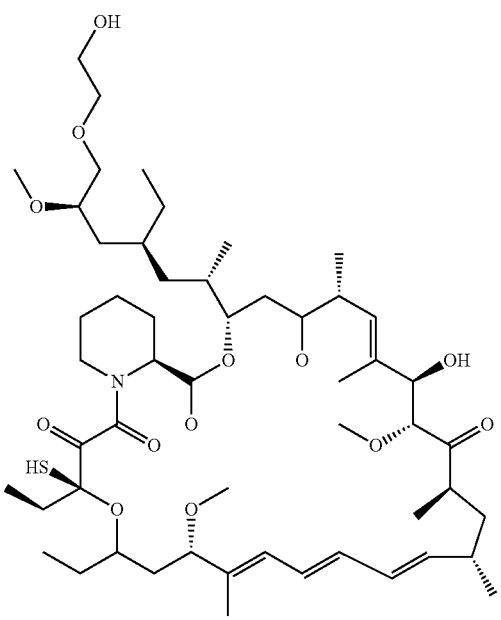

dihydroxy-12-[(2R)-1-[(1S,3R,4R)-4-(2-hydroxy-ethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone.

Bexarotene is sold as Targretin® and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl)ethenyl]benzoic acid.

Bexarotene is used to treat cutaneous T-cell lymphoma (CTCL, a type of skin cancer) in people whose disease could not be treated successfully with at least one other medication.

Sorafenib marketed as Nexavar® is in a class of medications called multikinase inhibitors. Its chemical name is 4-[4-[[4-chloro-3-(trifluoromethyl)phenyl]carbamoylamino]phenoxy]-N-methyl-pyridine-2-carboxamide. Sorafenib is used to treat advanced renal cell carcinoma (a type of cancer that begins in the kidneys). Sorafenib is also used to treat unresectable hepatocellular carcinoma (a type of liver cancer that cannot be treated with surgery).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Examples of erbB inhibitors include lapatinib, erlotinib, and gefitinib. Lapatinib, N-(3-chloro-4-{[(3-fluorophenyl)methyl]oxy}phenyl)-6-[5-({[2-(methylsulfonyl)ethyl]amino}methyl)-2-furanyl]-4-quinazolinamine (represented by Formula III, as illustrated), is a potent, oral, small-molecule, dual inhibitor of erbB-1 and erbB-2 (EGFR and HER2) tyrosine kinases that is approved in combination with capecitabine for the treatment of HER2-positive metastatic breast cancer.

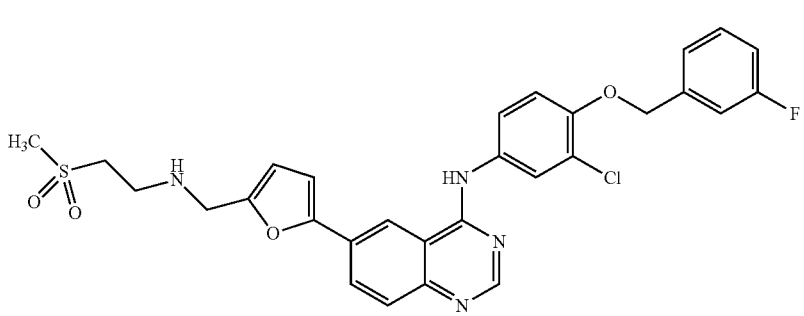

III

The free base, HCl salts, and ditosylate salts of the compound of formula (III) may be prepared according to the procedures disclosed in WO 99/35146, published Jul. 15, 1999; and WO 02/02552 published Jan. 10, 2002.

Erlotinib, N-(3-ethynylphenyl)-6,7-bis{[2-(methyloxy)ethyl]oxy}-4-quinazolinamine Commercially available under the tradename Tarceva) is represented by formula IV, as illustrated:

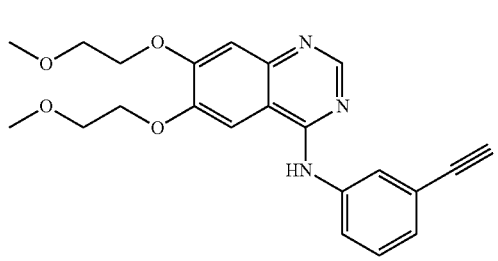

IV

The free base and HCl salt of erlotinib may be prepared, for example, according to U.S. Pat. No. 5,747,498, Example 20.

Gefitinib, 4-quinazolinamine, N-(3-chloro-4-fluorophenyl)-7-methoxy-6-[3-4-morpholin)propoxy] is represented by formula V, as illustrated:

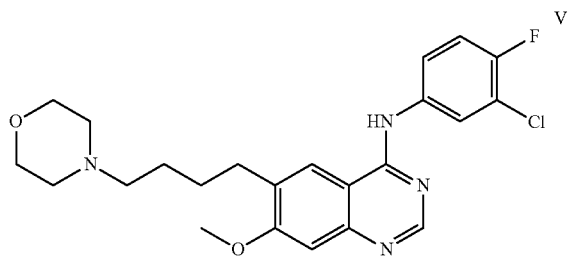 [SMILES: COc1cc2ncnc(Nc3ccc(F)c(Cl)c3)c2cc1CCCCN1CCOCC1]

Gefitinib, which is commercially available under the trade name IRESSA® (Astra-Zenenca) is an erbB-1 inhibitor that is indicated as monotherapy for the treatment of patients with locally advanced or metastatic non-small-cell lung cancer after failure of both platinum-based and docetaxel chemotherapies. The free base, HCl salts, and diHCl salts of gefitinib may be prepared according to the procedures of International Patent Application No. PCT/GB96/00961, filed Apr. 23, 1996, and published as WO 96/33980 on Oct. 31, 1996.

Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

Pertuzumab (also called 2C4, trade name Omnitarg) is a monoclonal antibody. The first of its class in a line of agents called "HER dimerization inhibitors". By binding to HER2, it inhibits the dimerization of HER2 with other HER receptors, which is hypothesized to result in slowed tumor growth. Pertuzumab is described in WO01/00245 published Jan. 4, 2001.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia (CLL; a type of cancer of the white blood cells) in adults who are refractory to treatment with fludarabine (Fludara) and alemtuzumab (Campath).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of Formula (I) and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Experimentals

Abbreviations: aq., aqueous; Boc$_2$O, di-tert-butyl dicarbonate; CDI, 1,1'-carbonyldiimidazole; CH$_2$Cl$_2$, dichloromethane; CHCl$_3$, chloroform; CH$_3$CN, acetonitrile; Cs$_2$CO$_3$, cesium carbonate; CsF, cesium fluoride; d, day(s); DBU, 1,8-diazabicyclo[5.4.0]undec-7-ene; DIAD, diisopropyl azodicarboxylate; DIPEA, diisopropylethylamine; DMF, N,N-dimethylformamide; DMSO, dimethylsulfoxide; EDC, N-(3-dimethylaminopropyl)-N'-ethylcarbodiimide hydrochloride; Et$_2$O, diethyl ether; EtOAc, ethyl acetate; EtOH, ethanol; h, hour(s); HCl, hydrochloric acid; HOAc, acetic acid; HOAt, 1-hydroxy-7-azabenzotriazole; HOBt, 1-hydroxybenzotriazole; K$_2$CO$_3$, potassium carbonate; KOAc, potassium acetate; KOCN, potassium cyanate; K$_3$PO$_4$, potassium phosphate; MeOH, methanol; MgSO$_4$, magnesium sulfate; min., minute(s); N$_2$, nitrogen gas; NaHCO$_3$, sodium bicarbonate; NaOAc, sodium acetate; Na$_2$SO$_4$, sodium sulfate; NH$_4$OH, ammonium hydroxide; NMP, N-methylpyrrolidone; PdCl$_2$(dppf), 1,1'-bis(diphenylphosphino)ferrocene-palladium(II)dichloride.dichloromethane complex; Pd(P-t-Bu$_3$)$_2$, bis(tri-tert-butylphosphine)palladium(0); Pd(PPh$_3$)$_4$, tetrakis(triphenylphosphine)palladium(0); PPh$_3$, triphenylphosphine; i-PrOH, isopropyl alcohol; THF, tetrahydrofuran; TFA, trifluoroacetic acid.

Preparation

The derivatives described herein were prepared by the general methods described below.

Schemes/Experimentals

A spirocyclic piperidine can be prepared from the protected piperidinone by the sequence outlined in Scheme I. After conversion of the piperidinone to the epoxide, the addition of various amines can open the epoxide to form amino alcohol intermediates. Acylation and cyclization using a reagent such as chloroacetyl chloride followed by removal of the BOC group then provides the spirocyclic piperidine intermediate.

Scheme I:

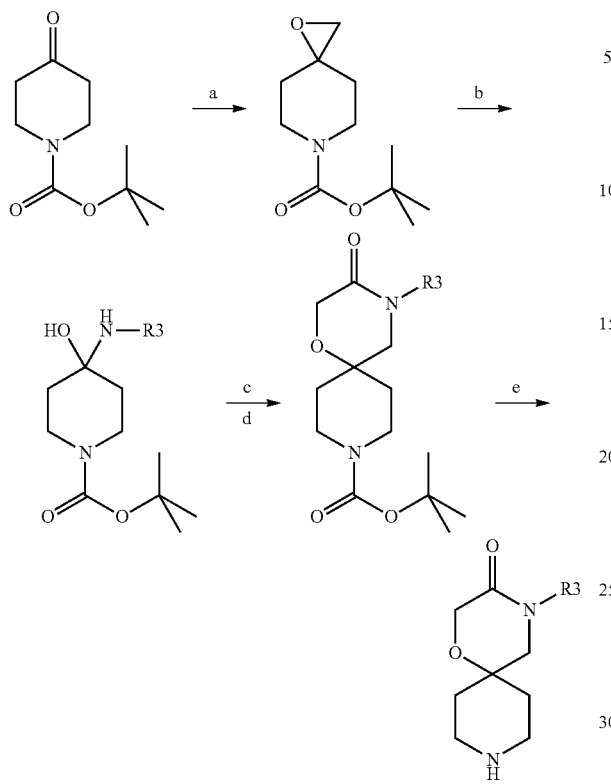

Conditions: a) trimethylsulfoxonium iodide, NaH, DMSO; b) R3—NH2, MeOH or EtOH, reflux; c) chloroacetyl chloride, NaHCO3, THF; d) K2CO3, (n-Bu)4N(HSO4), aq NaOH, THF; e) HCl, EtOH, dioxane.

When not commercially available, an alkyl bromide intermediate suitable for coupling with the spirocyclic piperidine can be prepared by brominating a functionalized precursor (Scheme II). Alternatively, a functionalized alcohol can be accessed which then can be activated as either a tosylate or mesylate. Several examples are provided in the experimental section that demonstrate how to prepare suitable intermediates.

Scheme II:

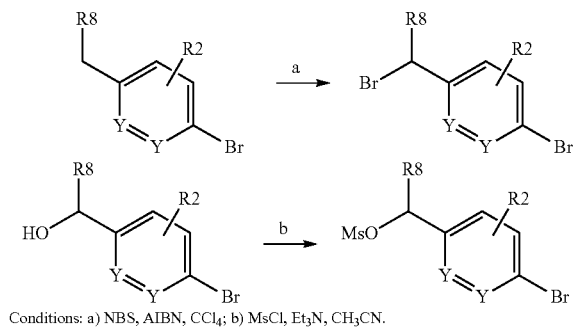

Conditions: a) NBS, AIBN, CCl4; b) MsCl, Et3N, CH3CN.

The spirocyclic piperidine can then be elaborated through alkylation with a suitable reagent with a leaving group (LG) such as a bromide, tosylate, or mesylate (Scheme III). Suzuki cross-coupling with various aryl or heteroaryl boronates or boronic acids then affords the final products, which can be resolved by chiral chromatography.

Scheme III:

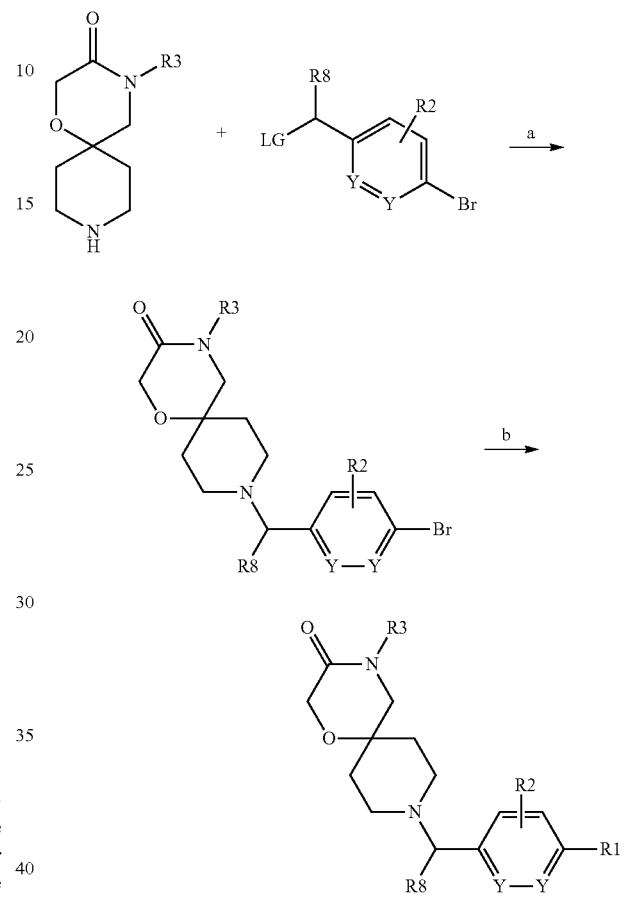

Conditions: a) DIPEA, Et3N or pyridine, CH3CN, 23-90° C.; b) R1—B(OR)2, PdCl2(dppf)—CH2Cl2 (cat.), aq K2CO3, dioxane, 100-120° C.

To allow for greater flexibility in the Suzuki cross-coupling reaction, the elaborated aryl bromide can also be converted to the intermediate boronate and then coupled with various aryl or heteroaryl halides to prepare the target compounds (Scheme IV).

Scheme IV:

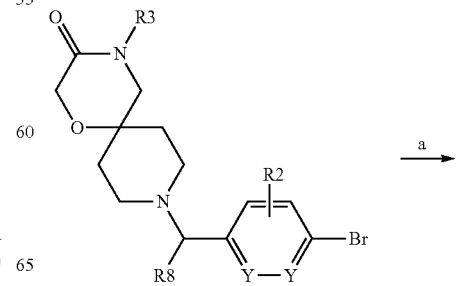

35
-continued

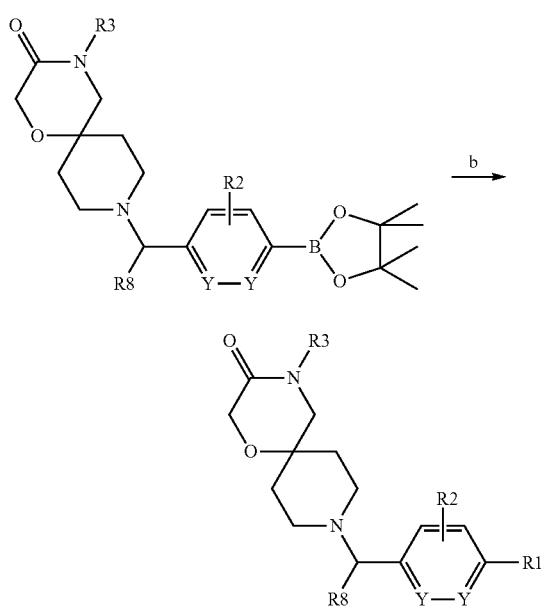

Conditions: a) 4,4,4′,4′,5,5,5′,5′-octamethyl-2,2′-bi-1,3,2-dioxaborolane, PdCl₂(dppf)——CH₂Cl₂ (cat.), KOAc, dioxane, 100° C.;
b) R1——Br, PdCl₂(dppf)——CH₂Cl₂ (cat.), aq K₂CO₃, dioxane, 100-120° C.

Alternative methods for preparing the elaborated aryl bromide are available, some of which are outlined below. A Petasis reaction can be utilized to couple the spirocyclic piperidine with a suitable aldehyde and boronic acid or ester (Scheme V; see Southwood, T J; Curry, M C; Hutton, C A, *Tetrahedron* 2006, 62, 236-242 and references therein). To prepare β-amino ester derivatives, Mannich-type reactions of aryl aldehydes and silyl ketene acetal with the spirocyclic piperidine can also be performed.

Scheme V:

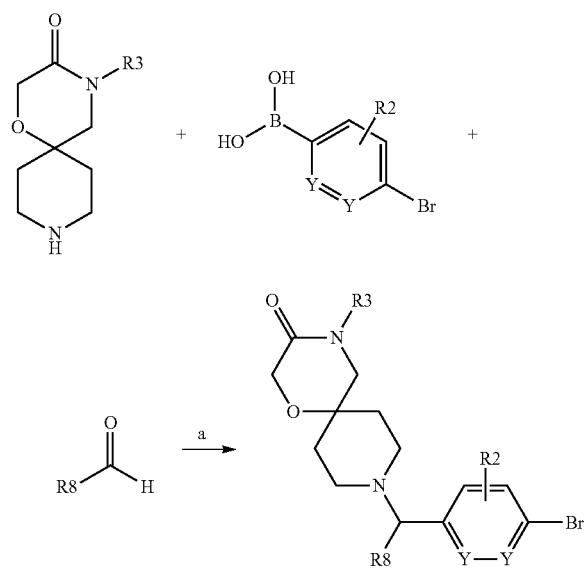

36
-continued

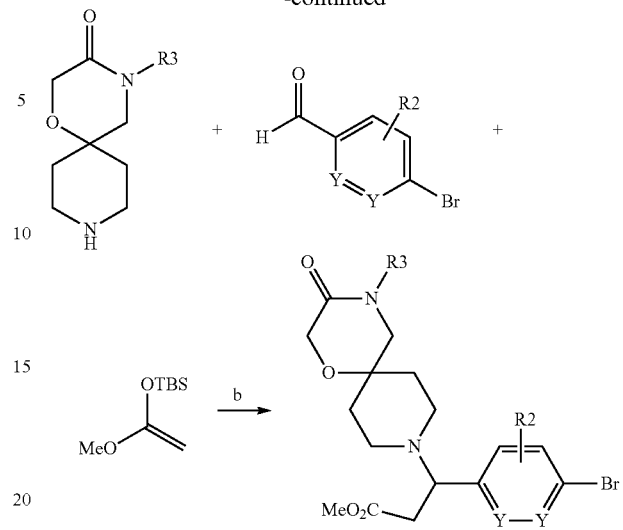

Conditions: a) CH₂Cl₂, 23° C.; b) B(OMe)₃, DMSO, 23° C.

Experimental Section:

Example 1

2-(4-cyclopropyl-3-oxo-1-oxa-4,9-diazaspiro[5.5]undecan-9-yl)-2-(4-(quinolin-7-yl)phenyl)acetic acid

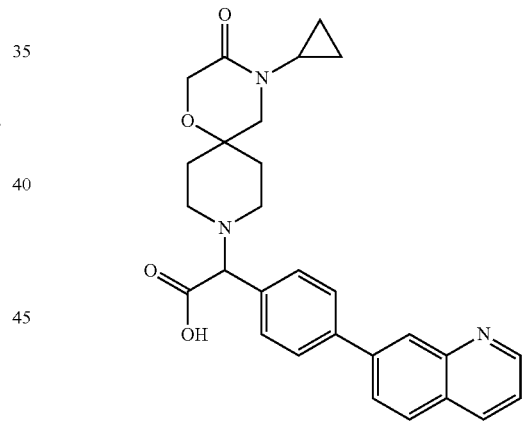

a) 1,1-Dimethylethyl 1-oxa-6-azaspiro[2.5]octane-6-carboxylate

A mixture of trimethylsulfoxonium iodide (50.2 mmol) and anhydrous dimethyl sulfoxide (DMSO) (50 mL) was stirred at room temperature for 1 h. The reaction was then cooled to 0° C. and 60% sodium hydride in mineral oil (60.2 mmol) was added in small portions over several minutes. The reaction was allowed to warm to room temperature and stirred for 2 h. The resulting white slurry was cooled to 0° C. then treated with solid 1,1-dimethylethyl 4-oxo-1-piperidinecarboxylate (50.2 mmol) in one portion. The ice bath was removed and stirring continued at room temperature for 18 h. Ice cold water (150 mL) was added and the mixture was extracted into diethyl ether (3×). The extracts were washed with brine, dried (sodium sulfate) then evaporated under reduced pressure to a yellow oil. The oil was dissolved in ethyl acetate, treated with silica powder (~20 g), and evaporated to dryness. This was placed on a short pad of silica in a sintered glass funnel and washed with hexanes (500 mL; the filtrate was discarded). The silica pad was then washed with 2:1 hexanes/ethyl acetate. The filtrate was evaporated in vacuo to give the title product (6.40 g, 57% yield) as a pale yellow oil that solidified upon standing. MS(ES)+ m/e 214.1 [M+H]+. $^1$H NMR (400 MHz, CDCl$_3$) δ ppm 1.47 (s, 11 H) 1.72-1.87 (m, 2 H) 2.69 (s, 2H) 3.36-3.50 (m, 2 H) 3.63-3.83 (m, 2 H).

b) 1,1-dimethylethyl 4-[(cyclopropylamino)methyl]-4-hydroxy-1-piperidinecarboxylate A sealable reaction vessel was charged with 1,1-dimethylethyl 1-oxa-6-azaspiro[2.5]octane-6-carboxylate (14.07 mmol), ethanol (70 mL) and cyclopropylamine (42.2 mmol). The vessel was purged with nitrogen, sealed and placed in a 75° C. oil bath for 20 h. The reaction mixture was cooled to room temperature and concentrated under reduced pressure. The resulting oil was purified by silica gel chromatography (5% methanol in ethyl acetate). The appropriate fractions were concentrated under reduced pressure and dried to afford the title product (3.56 g, 94% yield) as a viscous colorless oil. MS(ES)+ m/e 271.4 [M+H]$^+$. $^1$H NMR (400 MHz, DMSO-d$_6$) δ 4.20 (s, 1 H), 3.59 (d, J=12.6 Hz, 2 H), 3.05 (br. s., 2 H), 2.16-2.00 (m, 2 H), 1.49-1.31 (m, 14 H), 0.42-0.29 (m, 2 H), 0.24-0.13 (m, 2 H).

c) 1,1-dimethylethyl 4-{[chloroacetyl)(cyclopropyl)amino]methyl}-4-hydroxy-1-piperidinecarboxylate A solution of 1,1-dimethylethyl 4-[(cyclopropylamino)methyl]-4-hydroxy-1-piperidinecarboxylate (329 mmol) in tetrahydrofuran (500 mL) was added to a vigorously stirred suspension of sodium hydrogen carbonate (3193 mmol) in tetrahydrofuran (500 mL) at 0° C. Chloroacetyl chloride (332 mmol) was added dropwise over 10 min, maintaining the temperature at 0° C. The ice bath was removed and the mixture was stirred for 2 h, at which point a further aliquot of chloroacetyl chloride (41.1 mmol) was added. The mixture was stirred for 72 h then was filtered to remove the sodium hydrogen carbonate and the filter bed washed with tetrahydrofuran (300 mL) to afford the crude title product. MS(ES)+ m/e 347.1 [M+H+].

d) 1,1-dimethylethyl 4-cyclopropyl-3-oxo-1-oxa-4,9-diazaspiro[5.5]undecane-9-carboxylate A solution of 1,1-dimethylethyl 4-{[chloroacetyl)(cyclopropyl)amino]methyl}-4-hydroxy-1-piperidinecarboxylate in tetrahydrofuran (1300 mL) was treated with potassium carbonate (28.8 mmol) and tetrabutylammonium hydrogensulfate (11.72 mmol), and a 15% w/w solution of sodium hydroxide (1195 mmol) was added over 4 h. The mixture was stirred overnight and transferred to a separating flask. The aqueous layer was drained and the organic layer diluted with t-butyl methyl ether (1.5 L) and washed with a mixture of brine and saturated aq ammonium chloride (250 mL). The organic layer was dried (Na$_2$SO$_4$) and evaporated to afford the crude title product as a gel. MS(ES)+ m/e 311.3 [M+H+]; $^1$H NMR (400 MHz, CDCl$_3$) δ 4.14 (s, 2 H), 3.86 (br s, 2 H), 3.26-3.01 (m, 4 H), 2.84-2.70 (m, 2 H), 1.83 (d, J=12.1 Hz, 2H), 1.58-1.42 (m, 11 H), 0.92-0.80 (m, 2 H), 0.74-0.58 (m, 2 H).

e) 4-cyclopropyl-1-oxa-4,9-diazaspiro[5.5]undecan-3-one hydrochloride 1,1-Dimethylethyl 4-cyclopropyl-3-oxo-1-oxa-4,9-diazaspiro[5.5]undecane-9-carboxylate was dissolved in ethanol (300 mL) and cooled over an ice bath. A 4M solution of hydrogen chloride in dioxane (300 mL) was added, such that the temperature remained low. The ice bath was removed and the mixture was stirred at ambient temperature overnight. The solid was collected, washed with a little ethanol and diethyl ether to give the title product (47.1 g, 58%). The mother liquors were treated with diethyl ether (1.2 L), stirred for 30 min, and the solid was collected and dried to give a total combined yield of 78% of the title product (63.69 g) over the three steps. MS(ES)+ m/e 211.0[M+H+]; $^1$H NMR (400 MHz, DMSO-d$_6$) δ 9.17-8.64 (m, 2 H), 4.04 (s, 2 H), 3.14 (d, J=13.1 Hz, 2 H), 3.01-2.85 (m, 2 H), 2.83-2.71 (m, 1 H), 1.96-1.83 (m, 2 H), 1.83-1.68 (m, 2 H), 0.76-0.67 (m, 2 H), 0.64-0.55 (m, 2 H).

f) 2-(4-bromophenyl)-2-(4-cyclopropyl-3-oxo-1-oxa-4,9-diazaspiro[5.5]undecan-9-yl)acetic acid A suspension of 4-cyclopropyl-1-oxa-4,9-diazaspiro[5.5]undecan-3-one hydrochloride (8.11 mmol) in dichloromethane (20 mL) was treated with 1N aq sodium hydroxide (10 mL) at room temperature. After stirring for one hour, the dichloromethane layer had turned clear. The mixture was transferred to a separatory funnel and the organic phase was removed. The aqueous layer was extracted twice with dichloromethane. The combined organic layers were dried over sodium sulfate, filtered and concentrated in vacuo. The resulting yellow oil was dissolved in dichloromethane (20 mL) and treated with 2-oxoacetic acid monohydrate (8.11 mmol) and (4-bromophenyl)boronic acid (8.11 mmol) at room temperature. The reaction was allowed to stir at room temperature for 4 days, at which point an additional equivalent of 2-oxoacetic acid monohydrate (8.11 mmol) was added. The reaction was allowed to stir overnight, at which point the suspension was concentrated in vacuo. Purification of the residue by reverse phase HPLC (5-30% acetonitrile/water with 0.1% NH$_4$OH) afforded the title compound as a white solid (18%). MS(ES)+ m/e 422.9/424.8 [M+H]$^+$ (bromide isotope pattern).

g) 7-quinolinyl trifluoromethanesulfonate

To an ice-bath cooled suspension of 7-quinolinol (9.44 mmol) and pyridine (12.27 mmol) in anhydrous dichloromethane (DCM) (25.0 mL) was slowly added triflic anhydride (10.38 mmol) and the resulting dark solution was stirred at room temperature overnight. The mixture was washed with water, brine, and saturated aqueous sodium bicarbonate, and then dried over sodium sulfate, filtered, and evaporated to give a tan solid. Purification by flash chromatography (50% hexanes in ethyl acetate) gave the title product (2.43 g, 92% yield) as a white solid. MS(ES)+ m/e 277.9 [M+H]$^+$. $^1$H NMR (400 MHz, DMSO-d6) δ ppm 7.68 (dd, J=8.34, 4.29 Hz, 1 H) 7.76 (dd, J=8.97, 2.65 Hz, 1 H) 8.14 (d, J=2.78 Hz, 1H) 8.24 (d, J=9.09 Hz, 1 H) 8.49-8.55 (m, 1 H) 9.04 (dd, J=4.30, 1.77 Hz, 1 H).

h) 7-(4,4,5,5-tetramethyl-1,3,2-dioxaborolan-2-yl) quinoline

A flask was charged with a suspension of 7-quinolinyl trifluoromethanesulfonate (8.66 mmol), bis(pinacolato)diboron (10.39 mmol), PdCl2(dppf)-CH2Cl2 adduct (0.432 mmol), 1,1'-bis(diphenylphosphino)ferrocene (0.433 mmol) and potassium acetate (26.0 mmol) in 1,4-dioxane (40 mL) and heated at 100° C. for 2 h. The resulting dark suspension was cooled to room temperature, taken up into ethyl acetate, washed with water (2×) and brine, dried (sodium sulfate), and evaporated to an oil (2.25 g). The oil was purified by flash chromatography (10-60% ethyl acetate in hexanes). The desired fractions were combined and evaporated to an oil that was taken up in dichloromethane and evaporated again in vacuo to afford the title product (1.72 g, 74% yield) as a pale yellow oil that solidified upon standing. MS(ES)+ m/e 256.2 [M+H]+. $^1$H NMR (400 MHz, DMSO-d6) δ ppm 1.34 (s, 12 H) 7.58 (dd, J=8.34, 4.04 Hz, 1 H) 7.80 (dd, J=8.08, 1.01 Hz, 1 H) 7.93-8.00 (m, 1 H) 8.34 (s, 1 H) 8.36-8.41 (m, 1 H) 8.95 (dd, J=4.29, 1.77 Hz, 1 H).

i) 2-(4-cyclopropyl-3-oxo-1-oxa-4,9-diazaspiro[5.5] undecan-9-yl)-2-(4-(quinolin-7-yl)phenyl)acetic acid A solution of 2-(4-bromophenyl)-2-(4-cyclopropyl-3-oxo-1-oxa-4,9-diazaspiro[5.5]undecan-9-yl)acetic acid (0.402 mmol) in 1,4-dioxane (2 mL) and ethanol (0.2 mL) was treated with 7-(4,4,5,5-tetramethyl-1,3,2-dioxaborolan-2-yl) quinoline (0.442 mmol), PdCl$_2$(dppf)-CH$_2$Cl$_2$ adduct (0.020 mmol) and 2M aq potassium carbonate (0.602 mL). The vessel was purged with nitrogen, sealed and the reaction irradiated in a Biotage Initiator microwave at 120° C. for 10 min. The resulting black solution was then diluted with water (50 mL) and brine (10 mL), and the aqueous solution was sequentially extracted with dichloromethane and tetrahydrofuran. Only the tetrahydrofuran layer contained the product. The aqueous layer was concentrated in vacuo and the resulting solid was triturated with ethanol. The ethanol solution was filtered and added to the tetrahydrofuran layer. This organic phase was dried over sodium sulfate, filtered and concentrated in vacuo. Purification of the crude material by reverse phase HPLC (10-35% acetonitrile/water with 0.1% NH$_4$OH) afforded the title compound as a white solid (32%). MS(ES)+ m/e 472.4 [M+H]+.

Example 2

2-(4-cyclopropyl-3-oxo-1-oxa-4,9-diazaspiro[5.5] undecan-9-yl)-2-(4-(quinolin-7-yl)phenyl)acetamide

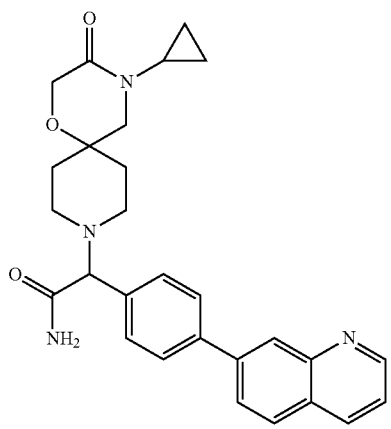 [SMILES: O=C(O)C(c1ccc(-c2ccc3cccnc3c2)cc1)N1CCC2(CC1)CN(C1CC1)C(=O)CO2]

a) A solution of 2-(4-cyclopropyl-3-oxo-1-oxa-4,9-diazaspiro[5.5]undecan-9-yl)-2-(4-(quinolin-7-yl)phenyl)acetic acid (0.110 mmol) in dichloromethane (0.75 mL) was treated with N-(3-dimethylaminopropyl)-N'-ethylcarbodiimide hydrochloride (31.7 mg, 0.165 mmol) and 4-(dimethylamino)pyridine (0.441 mmol) at room temperature. This mixture was stirred for 10 minutes at which point ammonium bromide (0.132 mmol) was added in one portion. The reaction was allowed to stir at room temperature overnight, at which point the solution was diluted with water (50 mL) and the pH was adjusted to ~10 using 30% w/v ammonium hydroxide solution. The aqueous layer was extracted with dichloromethane three times. The combined organic layers were washed with brine, dried over sodium sulfate, filtered and concentrated in vacuo. The crude material was purified by reverse phase HPLC (25-55% acetonitrile/water with 0.1% NH$_4$OH) and then again by reverse phase HPLC (5-25% acetonitrile with 0.1% TFA/water with 0.1% TFA). The product fractions were combined, the pH was adjusted to ~10 with 30% w/v ammonium hydroxide solution, and the mixture was extracted with dichloromethane. The organic layer was dried over sodium sulfate, filtered, and concentrated in vacuo. The resulting product was suspended in water (0.5 mL) and lyophilized to afford the title compound as a white solid (28%). MS(ES)+ m/e 471.3 [M+H]+.

Example 3

2-(4-cyclopropyl-3-oxo-1-oxa-4,9-diazaspiro[5.5] undecan-9-yl)-N,N-dimethyl-2-(4-(quinolin-7-yl) phenyl)acetamide

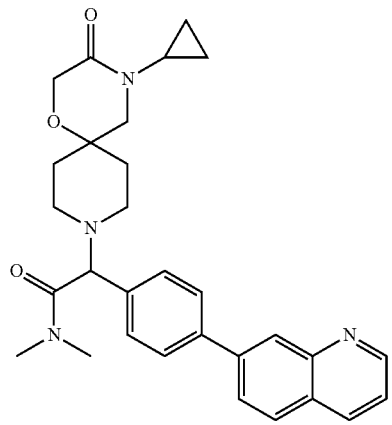 [SMILES: CN(C)C(=O)C(c1ccc(-c2ccc3cccnc3c2)cc1)N1CCC2(CC1)CN(C1CC1)C(=O)CO2]

a) A solution of 2-(4-cyclopropyl-3-oxo-1-oxa-4,9-diazaspiro[5.5]undecan-9-yl)-2-(4-(quinolin-7-yl)phenyl)acetic acid (0.191 mmol) in N,N-dimethylformamide (1 mL) was treated with diisopropylethylamine (0.573 mmol) and 2-chloro-1,3-dimethyl-4,5-dihydro-1H-imidazol-3-ium chloride (25% in dichloromethane, 0.108 mL) at room temperature. The reaction was stirred for 10 min at which point dimethylamine (2M in THF, 0.286 mmol) was added in one portion. The reaction was allowed to stir overnight, at which point additional dimethylamine (50 µL of a 2M solution in THF) and 2-chloro-1,3-dimethyl-4,5-dihydro-1H-imidazol-3-ium chloride (25% in dichloromethane, 0.030 mL) was added. The reaction mixture was stirred for an additional 30 minutes and then concentrated in vacuo. The crude material was purified by reverse phase HPLC (5-35% acetonitrile with 0.1% TFA/water with 0.1% TFA). The product fractions were combined, the pH was adjusted to ~10 with 30% w/v ammonium hydroxide solution, and the mixture was extracted with dichloromethane three times. The combined organic layer was dried over sodium sulfate, filtered, and concentrated in vacuo to afford the title compound as a white solid (26%). MS(ES)+ m/e 499.4 [M+H]+.

Example 4

2-(4-cyclopropyl-3-oxo-1-oxa-4,9-diazaspiro[5.5]undecan-9-yl)-N-methyl-2-(4-(quinolin-7-yl)phenyl)acetamide

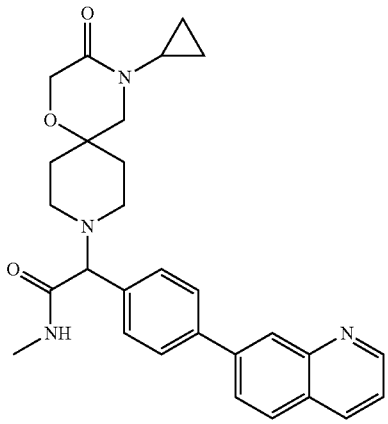 [SMILES: CNC(=O)C(c1ccc(-c2ccc3cccnc3c2)cc1)N1CCC2(CC1)CN(C1CC1)C(=O)CO2]

a) A solution of 2-(4-cyclopropyl-3-oxo-1-oxa-4,9-diazaspiro[5.5]undecan-9-yl)-2-(4-(quinolin-7-yl)phenyl)acetic acid (0.191 mmol) in dichloromethane (2 mL) was treated with N-(3-dimethylaminopropyl)-N'-ethylcarbodiimide hydrochloride (0.286 mmol) and 4-(dimethylamino)pyridine (0.763 mmol) at room temperature. After stirring for 10 minutes, this mixture was treated with methanamine (2M in THF) (0.400 mmol). The reaction vessel was sealed and the reaction was allowed to stir at room temperature for 16 hours. At this point an additional portion of N-(3-dimethylaminopropyl)-N'-ethylcarbodiimide hydrochloride (0.15 mmol) and methanamine (2M in THF) (0.400 mmol) was added and the solution was allowed to stir at room temperature for 3 hours. The reaction was concentrated under a nitrogen stream. Purification of the residue by reverse phase HPLC (5-35% acetonitrile with 0.1% TFA/water with 0.1% TFA) and then by silica gel chromatography (0-9% methanol/dichloromethane) followed by lyophilization from water with 10% acetonitrile (1 mL) afforded the title compound (26%) as a white solid. MS(ES)+ m/e 485.4 [M+H]+.

Example 5 methyl 3-(4-cyclopropyl-3-oxo-1-oxa-4,9-diazaspiro[5.5]undecan-9-yl)-3-(4-(quinolin-7-yl)phenyl)propanoate

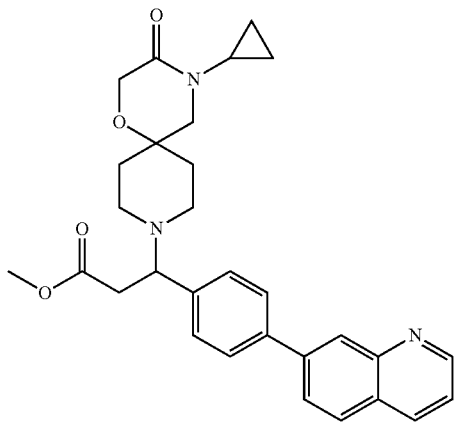 [SMILES: COC(=O)CC(c1ccc(-c2ccc3cccnc3c2)cc1)N1CCC2(CC1)CN(C1CC1)C(=O)CO2]

a) 4-cyclopropyl-1-oxa-4,9-diazaspiro[5.5]undecan-3-one

A suspension of 4-cyclopropyl-1-oxa-4,9-diazaspiro[5.5]undecan-3-one hydrochloride (8.11 mmol) in dichloromethane (10 mL) was treated with 1N aq NaOH (10.00 mmol). The biphasic mixture was stirred for 1 hour, at which point the cloudy organic layer had turned clear. The contents of the flask were further diluted with water (50 mL) and dichloromethane (50 mL) and the layers were separated. The aqueous layer was extracted with dichloromethane. The organic layers were combined, dried over sodium sulfate, filtered and concentrated in vacuo to afford the title compound as a yellow oil (80%). MS(ES)+ m/e 211.2 [M+H]+.

b) methyl 3-(4-bromophenyl)-3-(4-cyclopropyl-3-oxo-1-oxa-4,9-diazaspiro[5.5]undecan-9-yl)propanoate Following the procedure of Tanaka, et. al (*Eur. J. Org. Chem.* 2009, 1148-1151), a solution of 4-cyclopropyl-1-oxa-4,9-diazaspiro[5.5]undecan-3-one (1.427 mmol) in dimethyl sulfoxide (7 mL) was treated with 4-bromobenzaldehyde (2.140 mmol), tert-butyl((1-methoxyvinyl)oxy)dimethylsilane (2.140 mmol) and trimethyl borate (2.85 mmol).

The reaction was allowed to stir at room temperature for 16 hours, at which point the reaction was slowly diluted with water (10 mL) and then stirred for an additional 30 minutes. The aqueous mixture was extracted with ethyl acetate three times. The combined organic layer was washed with water and brine, dried over sodium sulfate, filtered and concentrated to dryness in vacuo. Purification of the residue by silica gel chromatography (0-100% ethyl acetate/hexanes) afforded the title compound (28%). MS(ES)+ m/e 450.9/453.1 [M+H]+ (bromide isotope pattern).

c) methyl 3-(4-cyclopropyl-3-oxo-1-oxa-4,9-diazaspiro[5.5]undecan-9-yl)-3-(4-(quinolin-7-yl)phenyl)propanoate A solution of methyl 3-(4-bromophenyl)-3-(4-cyclopropyl-3-oxo-1-oxa-4,9-diazaspiro[5.5]undecan-9-yl)propanoate (0.399 mmol) in 1,4-dioxane (2 mL) was treated with 7-(4,4,5,5-tetramethyl-1,3,2-dioxaborolan-2-yl)quinoline (0.439 mmol), PdCl$_2$(dppf)-CH$_2$Cl$_2$ adduct (0.020 mmol) and 2M aq potassium carbonate (1.196 mmol). The reaction vessel was purged with nitrogen and the reaction irradiated in a Biotage Initiator microwave at 120° C. for 15 minutes. The black reaction mixture was then diluted with water (50 mL) and extracted with dichloromethane three times. The combined organic layer was treated with Silicycle Si-thiol (30 mg), dried over sodium sulfate, filtered and concentrated in vacuo. Purification of the residue by reverse phase HPLC (15-60% acetonitrile/water with 0.1% NH$_4$OH) afforded the title compound as a yellow oil, which was subsequently lyophilized from 1 mL of water and then triturated with hexanes and dried under a nitrogen stream to afford the title compound as a white solid (61%). MS(ES)+ m/e 500.3 [M+H]+.

Example 6

3-(4-cyclopropyl-3-oxo-1-oxa-4,9-diazaspiro[5.5]undecan-9-yl)-3-(4-(quinolin-7-yl)phenyl)propanoic acid

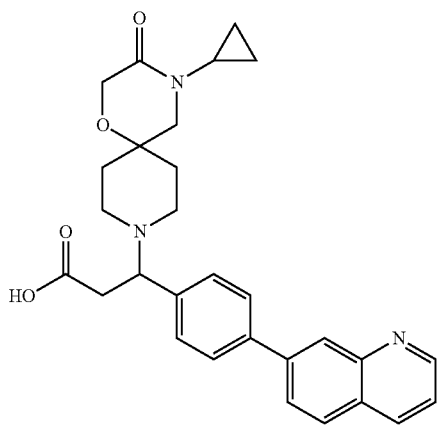 [SMILES: O=C(O)CC(c1ccc(-c2ccc3cccnc3c2)cc1)N1CCC2(CC1)CN(C1CC1)C(=O)CO2]

a) A solution of methyl 3-(4-cyclopropyl-3-oxo-1-oxa-4,9-diazaspiro[5.5]undecan-9-yl)-3-(4-(quinolin-7-yl)phenyl)propanoate (0.238 mmol) in ethanol (1 mL) was treated with LiOH (0.476 mmol) and stirred at room temperature for four days. The reaction mixture was concentrated in vacuo and the residue purified by reverse phase HPLC (15-50% acetonitrile/water with 0.1% NH$_4$OH) to afford the title compound as a white solid (72%). MS(ES)+ m/e 486.3 [M+H]$^+$.

Example 7

(−)-3-(4-cyclopropyl-3-oxo-1-oxa-4,9-diazaspiro[5.5]undecan-9-yl)-3-(4-(quinolin-7-yl)phenyl)propanamide

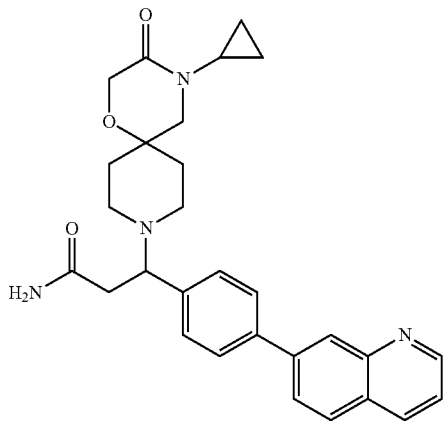 [SMILES: NC(=O)CC(c1ccc(-c2ccc3cccnc3c2)cc1)N1CCC2(CC1)CN(C1CC1)C(=O)CO2]

a) A solution of 3-(4-cyclopropyl-3-oxo-1-oxa-4,9-diazaspiro[5.5]undecan-9-yl)-3-(4-(quinolin-7-yl)phenyl)propanoic acid (0.152 mmol) in dichloromethane (1 mL) was treated with 4-(dimethylamino)pyridine (8.19 μmol), N,N'-diisopropylcarbodiimide (0.183 mmol), and ammonium bromide (0.229 mmol). The reaction mixture was sealed and was allowed to stir at room temperature overnight. Minimal conversion of starting material occurred, so additional 4-(dimethylamino)pyridine (8.19 μmol) was added and the reaction was stirred 3 hours at room temperature, at which point the mixture was diluted with acetonitrile (1 mL), and the reaction vessel was sealed and was stirred at 40° C. overnight. Minor conversion had occurred, so N-(3-dimethylaminopropyl)-N'-ethylcarbodiimide hydrochloride (0.183 mmol), 4-(dimethylamino)pyridine (0.457 mmol) and an additional portion of ammonium bromide (0.229 mmol) were added. The reaction mixture was sealed and allowed to stir at room temperature overnight. At this point the reaction was concentrated to dryness under a nitrogen stream. The crude material was purified by reverse phase HPLC (10-50% acetonitrile with 0.1% TFA/water with 0.1% TFA). The fractions containing the desired product were combined and the pH of the resulting mixture was adjusted to ~10 with 30% w/v ammonium hydroxide solution. This was concentrated to a minimal volume in vacuo and was then extracted with dichloromethane three times. The combined organic layer was dried over sodium sulfate, filtered and concentration in vacuo to afford the racemate of the title compound. Resolution of the racemate using chiral HPLC (Chiralpak AS-H, 9:1 acetonitrile:methanol) followed by concentration in vacuo and lyophilization from water with 5% acetonitrile yielded the title compound as a white solid in >99% ee (23% yield). MS(ES)+ m/e 485.4 [M+H]$^+$. α$_D$=−20 deg (c=0.01, 9:1 acetonitrile:methanol).

Example 8

(+)-3-(4-cyclopropyl-3-oxo-1-oxa-4,9-diazaspiro[5.5]undecan-9-yl)-3-(4-(quinolin-7-yl)phenyl)propanamide a) From Example 7a, the title product was also isolated using chiral HPLC (Chiralpak AS-H, 9:1 acetonitrile:methanol) followed by concentration in vacuo and lyophilization from water with 5% acetonitrile in >99% ee (23% yield). MS(ES)+ m/e 485.4 [M+H]$^+$. α$_D$=+21 deg (c=0.01, 9:1 acetonitrile:methanol).

Example 9

(+)-2-(4-cyclopropyl-3-oxo-1-oxa-4,9-diazaspiro[5.5]undec-9-yl)-2-[2-fluoro-4-(7-quinolinyl)phenyl]acetamide

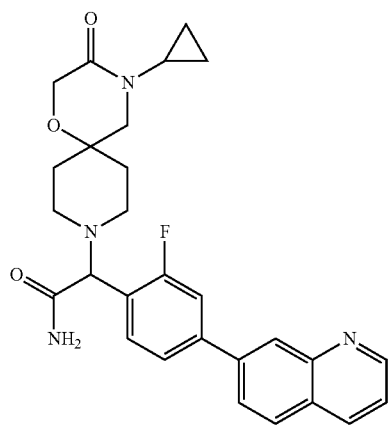 [SMILES: NC(=O)C(c1ccc(-c2ccc3cccnc3c2)cc1F)N1CCC2(CC1)CN(C1CC1)C(=O)CO2]

a) 2-(4-bromo-2-fluorophenyl)-2-hydroxyacetamide

To a solution of potassium cyanide (49.4 mmol) and ammonium chloride (99 mmol) in water (15 mL) was added solid 4-bromo-2-fluorobenzaldehyde (24.68 mmol) followed by diethyl ether (30.0 mL). The reaction mixture was stirred vigorously at room temperature for 15 minutes then the aqueous phase was adjusted to pH=5 by slow addition of glacial acetic acid (49.4 mmol). The reaction was diluted with water then the layers were separated and the aqueous layer was extracted with ether (3×). The combined ether layers were dried (sodium sulfate) and concentrated in vacuo to afford the intermediate cyanohydrin as a light yellow oil. To a solution of the crude cyanohydrin in 1,4-dioxane (20 mL) was added concentrated hydrochloric acid (10 mL, 329 mmol). The reaction solution was stirred at room temperature for 18 hours and then was diluted with ice cold water (100 mL) and extracted with ethyl acetate (3×). The extracts were washed with saturated aqueous sodium bicarbonate (2×) and brine and then dried over sodium sulfate, filtered, and evaporated under reduced pressure to afford the title compound (4.57 g, 73% yield) as a light yellow solid. MS(ES)+ m/e 248.1, 250.1 [M+H]$^+$. $^1$H NMR (400 MHz, DMSO-d6) δ ppm 5.06 (d, J=5.05 Hz, 1 H) 6.28 (d, J=5.05 Hz, 1 H) 7.30-7.45 (m, 3 H) 7.45-7.55 (m, 2 H).

b) 2-(4-bromo-2-fluorophenyl)-2-(4-cyclopropyl-3-oxo-1-oxa-4,9-diazaspiro[5.5]undec-9-yl)acetamide To a solution of 2-(4-bromo-2-fluorophenyl)-2-hydroxyacetamide (14.35 mmol) and triethylamine (43.1 mmol) in anhydrous acetonitrile (50.0 ml) was added neat methanesulfonyl chloride (20.81 mmol). The reaction stirred at room temperature for 18 hours then additional triethylamine (43.1 mmol) was added followed by solid 4-cyclopropyl-1-oxa-4,9-diazaspiro[5.5]undecan-3-one hydrochloride (15.79 mmol) in one portion. The reaction was heated at 90° C. for 3 hours then cooled to room temperature, diluted with water (150 mL) and stirred for 1 hour. The solids were collected by filtration, rinsed with water, and then dried by air suction and then vacuum to afford the title compound (3.53 g, 55% yield) as a white solid. MS(ES)+ m/e 440.1, 442.3 [M+H]$^+$.

c) (+)-2-(4-cyclopropyl-3-oxo-1-oxa-4,9-diazaspiro[5.5]undec-9-yl)-2-[2-fluoro-4-(7-quinolinyl)phenyl]acetamide Argon was bubbled through a suspension of 2-(4-bromo-2-fluorophenyl)-2-(4-cyclopropyl-3-oxo-1-oxa-4,9-diazaspiro[5.5]undec-9-yl)acetamide (4.61 mmol), 7-(4,4,5,5-tetramethyl-1,3,2-dioxaborolan-2-yl)quinoline (5.76 mmol), PdCl$_2$(dppf)-CH$_2$Cl$_2$ adduct (0.138 mmol), and 2.0 M aqueous potassium carbonate (18.44 mmol) in 1,4-dioxane (36.9 mL) for 10 minutes then the reaction was heated at 100° C. for 2 hours. The reaction was cooled, treated with silica powder (~10 g) then evaporated under reduced pressure to dryness. Purification of the residue on silica gel by flash chromatography (ethyl acetate, then 10% methanol/ethyl acetate) followed by combination of the product fractions and concentration to a residue that was taken into dichloromethane, filtered through celite, and concentrated in vacuo afforded the title product racemate (2.27 g, 91% yield) as a light tan solid. MS(ES)+ m/e 489.5 [M+H]$^+$. Chiral resolution of the racemate by chiral HPLC (Chromegachiral CC4, methanol) gave the title product as a light yellow foam (1.0 g, 45%). This solid was triturated with hot 3,3-dimethyl-2-butanone (10 mL) with ultrasonification for 5 minutes. The suspension was cooled to room temperature and the solids were filtered then vacuum dried to afford the title compound as an off white solid in 100% ee (770 mg, 34%). MS(ES)+ m/e 489.4 [M+H]$^+$. $α_D$=+43 deg (c=0.2, methanol).

Example 10

(−)-2-(4-cyclopropyl-3-oxo-1-oxa-4,9-diazaspiro[5.5]undec-9-yl)-2-[2-fluoro-4-(7-quinolinyl)phenyl]acetamide a) From Example 9c, the title product was also isolated using chiral HPLC (Chromegachiral CC4, methanol) in 99.4% ee (45% yield). MS(ES)+ m/e 489.5 [M+H]$^+$. $α_D$=−44 deg (c=0.2, methanol).

Example 11

(+)-2-(4-cyclopropyl-3-oxo-1-oxa-4,9-diazaspiro[5.5]undecan-9-yl)-2-(2-fluoro-4-(3-methylquinolin-7-yl)phenyl)acetamide

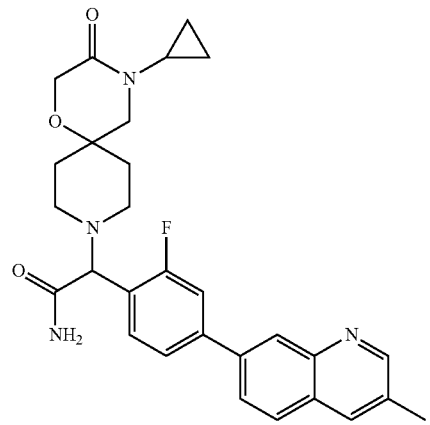 [SMILES: Cc1cnc2cc(-c3ccc(C(C(N)=O)N4CCC5(CC4)CN(C4CC4)C(=O)CO5)c(F)c3)ccc2c1]

a) 7-bromo-3-methylquinoline

A 1 L round bottom flask fitted with a stirbar, a Dean-Stark trap for solvents heavier than water, and a condenser was charged with 2-amino-4-bromobenzaldehyde (20 g, 100 mmol), sodium sulfate (71.0 g, 500 mmol), and p-toluenesulfonic acid monohydrate (4.75 g, 25.00 mmol). The solids were taken up in anhydrous chloroform (498 mL) and the suspension treated with 1-ethoxyprop-1-ene (14.39 mL, 130 mmol). The mixture was then heated to reflux with stirring overnight. The reaction mixture was cooled to room temperature and transferred to a 2 L separatory funnel. The solution was extracted twice with 200 mL saturated aq sodium bicarbonate and once with 200 mL water. The organic layer was isolated and the aqueous layers were combined and re-extracted twice with an additional 100 mL dichloromethane. The organics were then pooled, dried over sodium sulfate, filtered, and concentrated to a residue. The residue was purified by flash chromatography (0.2-1.9% methanol:dichloromethane). Fractions containing the desired material were pooled and concentrated to afford the title compound as a bright orange solid (5.603 g, 25.2 mmol, 25% yield). MS(ES)$^+$ m/e 221.8 [M+H]$^+$.

b) (+)-2-(4-cyclopropyl-3-oxo-1-oxa-4,9-diazaspiro[5.5]undecan-9-yl)-2-(2-fluoro-4-(3-methylquinolin-7-yl)phenyl)acetamide A solution of 2-(4-bromo-2-fluorophenyl)-2-(4-cyclopropyl-3-oxo-1-oxa-4,9-diazaspiro[5.5]undecan-9-yl)acetamide (0.223 mmol) in dry 1,4-dioxane (1.5 mL) was treated with bis(pinacolato)diboron (0.268 mmol), potassium acetate (0.499 mmol) and PdCl$_2$(dppf)-CH$_2$Cl$_2$ adduct (0.011 mmol). The solution was degassed with nitrogen, sealed, and stirred at 100° C. for 3 hours. The reaction mixture was cooled to room temperature and was treated with 7-bromo-3-methylquinoline (0.223 mmol), PdCl$_2$(dppf)-CH$_2$Cl$_2$ adduct (0.011 mmol) and 2M aq potassium carbonate (0.669 mmol). The reaction vessel was purged with nitrogen gas, sealed, and irradiated in a Biotage Initiator Microwave at 120° C. for 15 minutes. The resulting black mixture was diluted with water (50 mL) and extracted with dichloromethane three times. The combined organic layer was treated with Silicycle Si-thiol (30 mg), dried over sodium sulfate, filtered and concentrated in vacuo. Purification of the residue by silica gel chromatography (0-10% methanol/dichloromethane followed by 30% methanol/dichloromethane) and resolution by chiral HPLC (Chromegachiral CC4, methanol) afforded the title compound in >99% ee (31% yield). MS(ES)+ m/e 503.2 [M+H]$^+$. $\alpha_D$=+ 38 deg (c=0.03, methanol).

Example 12

(−)-2-(4-cyclopropyl-3-oxo-1-oxa-4,9-diazaspiro[5.5]undecan-9-yl)-2-(2-fluoro-4-(3-methylquinolin-7-yl)phenyl)acetamide a) From Example 11b, the title product was also isolated using chiral HPLC (Chromegachiral CC4, methanol) in >99% ee (31% yield). MS(ES)+ m/e 503.2 [M+H]$^+$. $\alpha_D$=−36 deg (c=0.03, methanol).

Example 13

4-cyclopropyl-9-(1-(4-(quinolin-7-yl)phenyl)ethyl)-1-oxa-4,9-diazaspiro[5.5]undecan-3-one

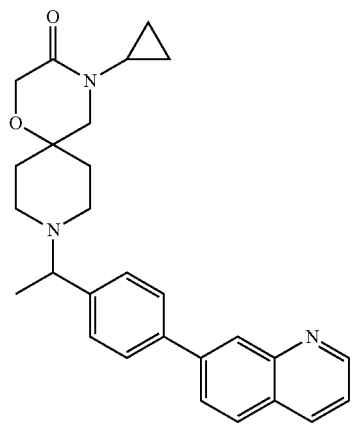 [SMILES: CC(c1ccc(-c2ccc3cccnc3c2)cc1)N1CCC2(CC1)CN(C1CC1)C(=O)CO2]

a) 1-bromo-4-(1-bromoethyl)benzene

A solution of 1-(4-bromophenyl)ethanol (1.492 mmol) in dichloromethane (8 mL) at 0° C. was treated dropwise with a solution of phosphorous tribromide (0.597 mmol) in dichloromethane (2 mL). The reaction was allowed to warm to room temperature and was stirred overnight. The reaction was then quenched with saturated aq sodium bicarbonate (10 mL) and was stirred for 2 h. The biphasic mixture was further diluted with dichloromethane (50 mL) and the organic layer was separated from the aqueous layer. The organic layer was dried over sodium sulfate, filtered and concentrated to dryness in vacuo. Purification of the residue by flash chromatography (0-25% ethyl acetate/hexanes) gave the title product (91 mg, 23% yield) as a clear oil. $^1$H NMR (400 MHz, DMSO-d$_6$) δ ppm 1.97 (d, J=6.82 Hz, 3 H) 5.50 (q, J=6.82 Hz, 1 H) 7.48 (d, J=8.59 Hz, 2 H) 7.57 (m, J=8.59 Hz, 2 H).

b) 9-(1-(4-bromophenyl)ethyl)-4-cyclopropyl-1-oxa-4,9-diazaspiro[5.5]undecan-3-one A solution of 4-cyclopropyl-1-oxa-4,9-diazaspiro[5.5]undecan-3-one hydrochloride (0.341 mmol) in N,N-dimethylformamide (1.5 mL) was treated with potassium carbonate (0.682 mmol) and 1-bromo-4-(1-bromoethyl)benzene (0.341 mmol). The reaction mixture was stirred at room temperature overnight. The solution was diluted with water (50 mL) and was extracted three times with dichloromethane. The organic layers were combined, washed with brine, dried over sodium sulfate, filtered, and concentrated in vacuo to afford the title compound as a brown residue (117 mg, 87%). MS(ES)$^+$ m/e 392.9/394.7 [M+H]$^+$ (bromide isotope pattern).

c) 4-cyclopropyl-9-(1-(4-(quinolin-7-yl)phenyl)ethyl)-1-oxa-4,9-diazaspiro[5.5]undecan-3-one A solution of 9-[1-(4-bromophenyl)ethyl]-4-cyclopropyl-1-oxa-4,9-diazaspiro[5.5]undecan-3-one (0.297 mmol) in 1,4-dioxane (1.5 mL) was treated with 7-(4,4,5,5-tetramethyl-1,3,2-dioxaborolan-2-yl)quinoline (0.329 mmol), PdCl$_2$(dppf)-CH$_2$Cl$_2$ adduct (0.015 mmol) and 2M aq potassium carbonate (0.892 mmol). The reaction vessel was purged with nitrogen and sealed, and the mixture was irradiated in a Biotage Initiator Microwave at 150° C. for 20 min. The resulting black mixture was diluted with water (50 mL) and extracted three times with dichloromethane. The combined organic layers were treated with Silicycle Si-thiol (20 mg), dried over sodium sulfate, filtered and concentrated in vacuo. The resulting crude product was purified by silica gel chromatography (4-10% methanol/dichloromethane) and then by reverse phase HPLC (5-35% acetonitrile with 0.1% TFA/water with 0.1% TFA). Fractions containing the desired product were combined and the pH of the resulting mixture was adjusted to ~11 with 30% w/v ammonium hydroxide solution. This mixture was concentrated to a minimal volume in vacuo and was then extracted three times with dichloromethane. The combined organic layers were dried over sodium sulfate, filtered and concentrated in vacuo. Lyophilization of the resulting semi-solid from water yielded the title compound as a white solid (26 mg, 18%). MS(ES)$^+$ m/e 442.1 [M+H]$^+$.

Example 14

4-cyclopropyl-9-(1-(3-fluoro-4'-methoxy-[1,1'-biphenyl]-4-yl)ethyl)-1-oxa-4,9-diazaspiro[5.5]undecan-3-one

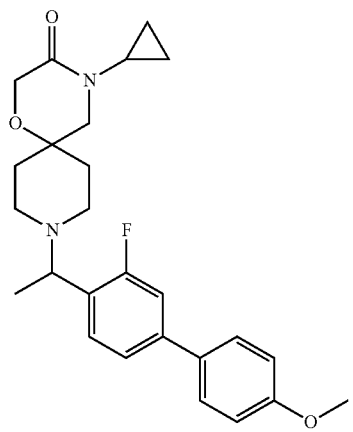 [SMILES: COc1ccc(-c2ccc(C(C)N3CCC4(CC3)CN(C3CC3)C(=O)CO4)c(F)c2)cc1]

a) 4-bromo-1-(1-bromoethyl)-2-fluorobenzene

A solution of 1-(4-bromo-2-fluorophenyl)ethanol (8.95 mmol) in dichloromethane (40 mL) at 0° C. was treated dropwise with a solution of phosphorus tribromide (3.58 mmol) in dichloromethane (10 mL). The reaction mixture was allowed to warm to room temperature and was stirred overnight. The solution was concentrated to a residue in vacuo. Purification of the residue by silica gel chromatography (hexanes) yielded the title compound as a clear oil (1.47 g, 58.3% yield). $^1$H NMR (400 MHz, DMSO-$d_6$) δ ppm 2.00 (d, J=6.82 Hz, 3 H) 5.58 (q, J=7.07 Hz, 1 H) 7.47 (dd, J=8.34, 1.77 Hz, 1 H) 7.57-7.65 (m, 2 H).

b) 9-(1-(4-bromo-2-fluorophenyl)ethyl)-4-cyclopropyl-1-oxa-4,9-diazaspiro[5.5]undecan-3-one A solution of 4-cyclopropyl-1-oxa-4,9-diazaspiro[5.5]undecan-3-one hydrochloride (2.483 mmol) in N,N-dimethylformamide (10 mL) was treated with potassium carbonate (7.45 mmol) and 4-bromo-1-(1-bromoethyl)-2-fluorobenzene (2.483 mmol). The reaction was stirred at room temperature for three days. The solution was diluted with water (200 mL) and was extracted three times with ethyl acetate. The organic layers were combined, washed with brine (five times), dried over sodium sulfate, filtered and concentrated in vacuo to afford the title compound as a yellow oil (1.01 g, 89%). MS(ES)+ m/e 411.0/412.9 [M+H]+ (bromide isotope pattern).

c) 4-cyclopropyl-9-(1-(3-fluoro-4'-methoxy-[1,1'-biphenyl]-4-yl)ethyl)-1-oxa-4,9-diazaspiro[5.5]undecan-3-one A solution of 9-[1-(4-bromo-2-fluorophenyl)ethyl]-4-cyclopropyl-1-oxa-4,9-diazaspiro[5.5]undecan-3-one (0.219 mmol) in 1,4-dioxane (2 mL) was treated with (4-methoxyphenyl)boronic acid (0.241 mmol), PdCl$_2$(dppf)-CH$_2$Cl$_2$ adduct (10.94 μmol), and 2M aq potassium carbonate (0.656 mmol). The reaction vessel was purged with nitrogen and sealed, and the mixture was irradiated in a Biotage Initiator Microwave at 130° C. for 20 min. The resulting black mixture was diluted with water (50 mL) and extracted three times with dichloromethane. The combined organic layers were treated with Silicycle Si-thiol (20 mg), dried over sodium sulfate, filtered and concentrated in vacuo. The resulting crude material was purified by reverse phase HPLC (15-45% acetonitrile with 0.1% TFA/water with 0.1% TFA). Fractions containing the desired product were combined and the pH of the resulting mixture was adjusted to ~10 with 30% w/v ammonium hydroxide solution. This mixture was concentrated to a minimal volume in vacuo and was then extracted three times with dichloromethane. The combined organic layers were dried over sodium sulfate, filtered and concentrated in vacuo. Purification of the resulting solid by silica gel chromatography (3-10% methanol/dichloromethane) afforded the title compound as a white solid (46 mg, 45%). MS(ES)+ m/e 439.1 [M+H]+.

Example 15

(+)-4-cyclopropyl-9-(1-(2-fluoro-4-(quinolin-7-yl) phenyl)ethyl)-1-oxa-4,9-diazaspiro[5.5]undecan-3-one

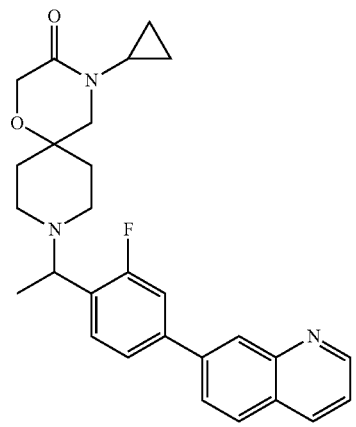 [SMILES: CC(c1ccc(-c2ccc3cccnc3c2)cc1F)N1CCC2(CC1)CN(C1CC1)C(=O)CO2]

a) A solution of 9-(1-(4-bromo-2-fluorophenyl)ethyl)-4-cyclopropyl-1-oxa-4,9-diazaspiro[5.5]undecan-3-one (0.438 mmol) in 1,4-dioxane (2 mL) was treated with quinolin-7-ylboronic acid (0.481 mmol), PdCl$_2$(dppf)-CH$_2$Cl$_2$ adduct (0.022 mmol), and 2M aq potassium carbonate (1.313 mmol). The reaction vessel was purged with nitrogen and sealed, and the mixture was irradiated in a Biotage Initiator Microwave at 130° C. for 20 min. The resulting black mixture was diluted with water (50 mL) and extracted three times with dichloromethane. The aqueous layer was further diluted with brine (50 mL) and was then extracted with tetrahydrofuran. The organic layers were combined and were treated with Silicycle Si-thiol (50 mg), dried over sodium sulfate, filtered and concentrated in vacuo. Purification of the residue by silica gel chromatography (4-10% methanol/dichloromethane) followed by resolution of the product by chiral HPLC (Lux Cellulose-2 column, acetonitrile:methanol 85:15) afforded the title compound as a white solid (50 mg, 23%). MS(ES)+ m/e 460.2 [M+H]+, >99% ee, α$_D$=+38 deg (c=0.02, acetonitrile:methanol 85:15).

Example 16

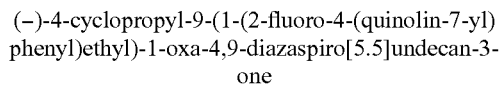
(−)-4-cyclopropyl-9-(1-(2-fluoro-4-(quinolin-7-yl)phenyl)ethyl)-1-oxa-4,9-diazaspiro[5.5]undecan-3-one a) From Example 15a, the title product was isolated using chiral HPLC (Lux Cellulose-2 column, acetonitrile:methanol 85:15) followed by concentration in vacuo (51 mg, 24% yield). MS(ES)+ m/e 460.3 [M+H]$^+$, >97% ee, $\alpha_D$=−36 deg (c=0.02, acetonitrile:methanol 85:15).

Example 17

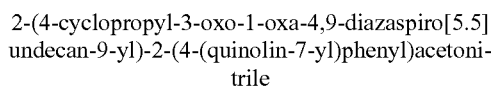
2-(4-cyclopropyl-3-oxo-1-oxa-4,9-diazaspiro[5.5]undecan-9-yl)-2-(4-(quinolin-7-yl)phenyl)acetonitrile

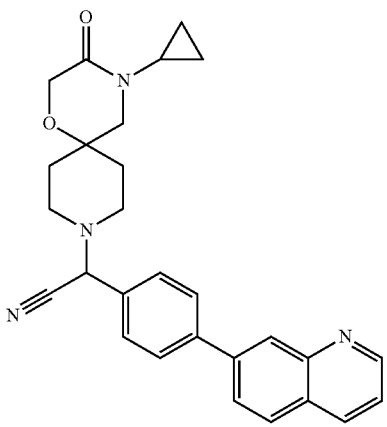 [SMILES: N#CC(c1ccc(-c2ccc3cccnc3c2)cc1)N1CCC2(CC1)CN(C1CC1)C(=O)CO2]

a) 2-(4-(quinolin-7-yl)phenyl)acetonitrile

A solution of 2-(4-bromophenyl)acetonitrile (2.55 mmol) in 1,4-dioxane (5 mL) was treated with 7-(4,4,5,5-tetramethyl-1,3,2-dioxaborolan-2-yl)quinoline (2.64 mmol), PdCl$_2$(dppf)-CH$_2$Cl$_2$ adduct (0.083 mmol), and 2M aq potassium carbonate (5.10 mmol). The reaction vessel was purged with nitrogen and sealed, and the mixture irradiated in a Biotage Initiator Microwave at 120° C. for 20 min. The resulting black mixture was diluted with water (100 mL) and extracted three times with dichloromethane. The combined organic layers were dried over sodium sulfate, filtered and concentrated in vacuo. Purification of the residue by silica gel chromatography (0-100% ethyl acetate/hexanes) afforded the title compound as a yellow solid (424 mg, 64%). MS(ES)+ m/e 245.3 [M+H]$^+$.

b) 2-bromo-2-(4-(quinolin-7-yl)phenyl)acetonitrile

A solution of 2-(4-(quinolin-7-yl)phenyl)acetonitrile (0.409 mmol) in carbon tetrachloride (2 mL) was degassed for three minutes with a stream of nitrogen. The solution was then treated with N-bromosuccinimide (0.450 mmol) and azobisisobutyronitrile (0.020 mmol). The reaction vessel was purged with nitrogen and sealed and the mixture was allowed to stir overnight in a 75° C. oil bath. The reaction mixture was then directly loading onto silica gel and concentrated in vacuo. Purification of the residue by silica gel chromatography (0-80% ethyl acetate/hexanes) afforded the title compound (30 mg, 17%). MS(ES)+ m/e 322.9/325.0 [M+H]$^+$ (bromide isotope pattern).

c) 2-(4-cyclopropyl-3-oxo-1-oxa-4,9-diazaspiro[5.5]undecan-9-yl)-2-(4-(quinolin-7-yl)phenyl)acetonitrile A solution of 4-cyclopropyl-1-oxa-4,9-diazaspiro[5.5]undecan-3-one hydrochloride (0.101 mmol) in N,N-dimethylformamide (0.5 mL) was treated with potassium carbonate (0.209 mmol) and 2-bromo-2-(4-(quinolin-7-yl)phenyl)acetonitrile (0.070 mmol). The reaction was stirred overnight at room temperature, at which point it was diluted with water (50 mL) and was extracted with three times with dichloromethane. The aqueous layer was further diluted with brine (25 mL) and was extracted twice with tetrahydrofuran. The organic layers were combined and dried over sodium sulfate, filtered and concentrated in vacuo. The resulting crude material was purified by silica gel chromatography (0-9% methanol/dichloromethane). The fractions containing the desired product were combined, concentrated in vacuo, and lyophilized from water to afford the title compound a pale yellow solid (15%). MS(ES)+ m/e 453.2 [M+H]$^+$.

Example 18

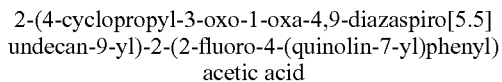
2-(4-cyclopropyl-3-oxo-1-oxa-4,9-diazaspiro[5.5]undecan-9-yl)-2-(2-fluoro-4-(quinolin-7-yl)phenyl)acetic acid

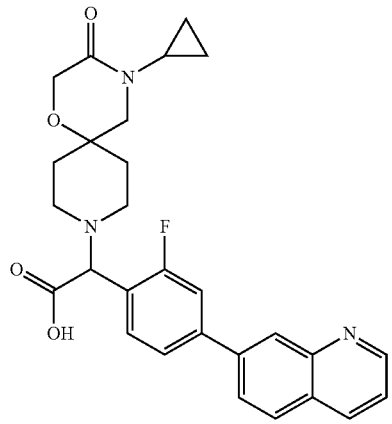

a) 2-(4-bromo-2-fluorophenyl)-2-(4-cyclopropyl-3-oxo-1-oxa-4,9-diazaspiro[5.5]undecan-9-yl)acetic acid A suspension of 4-cyclopropyl-1-oxa-4,9-diazaspiro[5.5]undecan-3-one hydrochloride (4.05 mmol) in dichloromethane (10 mL) was treated with 1N aq sodium hydroxide (5.00 mmol) at room temperature. After one hour the organic layer of the reaction had turned from cloudy to clear. The aqueous layer was removed via pipet. To the remaining organic solution was added 2-oxoacetic acid monohydrate (4.05 mmol) and (4-bromo-2-fluorophenyl)boronic acid (4.05 mmol) at room temperature. The reaction was allowed to stir at room temperature for three days, after which the solution was concentrated to dryness under a stream of nitrogen. The resulting crude material was diluted with acetonitrile (10 mL) and transferred to a microwave reactor vial. The reaction vessel was sealed and the mixture irradiated in a Biotage Initiator Microwave at 80° C. for 30 min and then at 100° C. for 30 min. The reaction was concentrated to dryness in vacuo. The resulting crude material was purified by reverse phase HPLC (10-40% acetonitrile/water w/0.1% $NH_4OH$) to afford the title compound as a white solid (853 mg, 45%). MS(ES)+ m/e 441.0/443.1 $[M+H]^+$ (bromide isotope pattern).

b) 2-(4-cyclopropyl-3-oxo-1-oxa-4,9-diazaspiro[5.5]undecan-9-yl)-2-(2-fluoro-4-(quinolin-7-yl)phenyl)acetic acid A solution of 2-(4-bromo-2-fluorophenyl)-2-(4-cyclopropyl-3-oxo-1-oxa-4,9-diazaspiro[5.5]undecan-9-yl)acetic acid (0.408 mmol) in 1,4-dioxane (2 mL) was treated with 7-(4,4,5,5-tetramethyl-1,3,2-dioxaborolan-2-yl)quinoline (0.449 mmol), $PdCl_2$(dppf)-$CH_2Cl_2$ adduct (0.020 mmol) and 2M aq potassium carbonate (1.224 mmol). The reaction vessel was purged with nitrogen and sealed, and the mixture irradiated in a Biotage Initiator Microwave at 120° C. for 15 min. The reaction mixture was diluted with methanol (10 mL), treated with Silicycle Si-thiol (20 mg), dried over sodium sulfate, filtered and concentrated in vacuo. Purification of the residue by reverse phase HPLC (10-40% acetonitrile/water with 0.1% $NH_4OH$) followed by lyophilization from water afforded the title compound as a white solid (134 mg, 63%). MS(ES)+ m/e 490.3 $[M+H]^+$.

Example 19

(−)-2-(4-cyclopropyl-3-oxo-1-oxa-4,9-diazaspiro[5.5]undecan-9-yl)-2-(4-(quinolin-7-yl)phenyl)acetamide

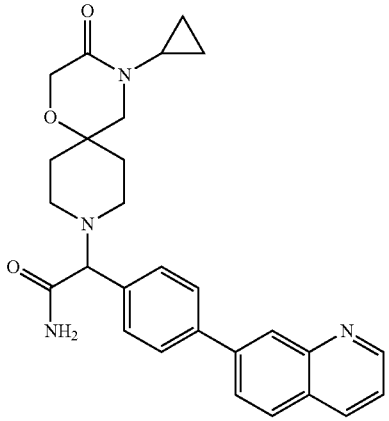 [SMILES: NC(=O)C(c1ccc(-c2ccc3cccnc3c2)cc1)N1CCC2(CC1)CN(C1CC1)C(=O)CO2]

a) A solution of 2-(4-cyclopropyl-3-oxo-1-oxa-4,9-diazaspiro[5.5]undecan-9-yl)-2-(4-(quinolin-7-yl)phenyl)acetic acid (0.142 mmol) in dichloromethane (1 mL) was treated with N-(3-dimethylaminopropyl)-N'-ethylcarbodiimide hydrochloride (0.213 mmol) and 4-(dimethylamino)pyridine (0.568 mmol). This mixture was stirred for ten minutes at which point ammonium bromide (0.171 mmol) was added. The reaction was stirred at room temperature for two days. The reaction was then concentrated to dryness under a stream of nitrogen. The resulting crude product was purified by reverse phase HPLC (10-40% acetonitrile with 0.1% TFA/water with 0.1% TFA). Fractions containing the desired product were combined and the pH of the resulting mixture was adjusted to ~10 with 30% w/v aq ammonium hydroxide. This mixture was concentrated to a minimal volume in vacuo and was then extracted three times with dichloromethane. The combined organic layer was dried over sodium sulfate, filtered and concentrated in vacuo. Resolution of the product by chiral HPLC (Chiralpak IC, acetonitrile:methanol 1:1) followed by lyophilization from water (1 mL w/5% acetonitrile) afforded the title compound as a white solid in >99% ee (25% yield). MS(ES)+ m/e 471.3 $[M+H]^+$; $α_D$=−58 deg (c=0.05, acetonitrile-methanol 1:1).

Example 20

(+)-2-(4-cyclopropyl-3-oxo-1-oxa-4,9-diazaspiro[5.5]undecan-9-yl)-2-(4-(quinolin-7-yl)phenyl)acetamide a) From Example 19a, the title product was isolated as a white solid using chiral HPLC (Chiralpak IC, acetonitrile:methanol 1:1) followed by lyophilization from water (w/5% acetonitrile) (25% yield). MS(ES)+ m/e 471.3 $[M+H]^+$, >97% ee, $α_D$=+56 deg (c=0.07, acetonitrile-methanol 1:1).

Example 21

2-(4-cyclopropyl-3-oxo-1-oxa-4,9-diazaspiro[5.5]undecan-9-yl)-2-(2-fluoro-4-(quinolin-7-yl)phenyl)acetamide

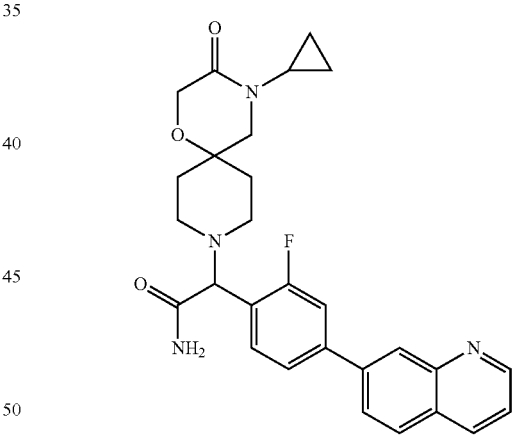

a) A solution of 2-(4-cyclopropyl-3-oxo-1-oxa-4,9-diazaspiro[5.5]undecan-9-yl)-2-(2-fluoro-4-(quinolin-7-yl)phenyl)acetic acid (0.257 mmol) in dichloromethane (2 mL) was treated with N-(3-Dimethylaminopropyl)-N'-ethylcarbodiimide hydrochloride (0.386 mmol) and 4-(dimethylamino)pyridine (1.030 mmol) at room temperature. This mixture was stirred for ten minutes at which point ammonium bromide (0.309 mmol) was added. The reaction was allowed to stir at room temperature overnight. The reaction was then concentrated to dryness under a stream of nitrogen. The resulting crude product was purified by reverse phase HPLC (10-40% acetonitrile with 0.1% TFA/water with 0.1% TFA). Fractions containing the desired product were combined and the pH of the resulting mixture was adjusted to ~10 with 30% w/v aq ammonium hydroxide. This mixture was concentrated to a minimal volume in vacuo and was extracted three times with dichloromethane. The combined organic layers were dried over sodium sulfate, filtered and concentrated in vacuo. Lyophilization from water afforded the title product as a white solid (47 mg, 35%). MS(ES)+ m/e 489.5 [M+H]+.

Example 22

4-cyclopropyl-9-(2-hydroxy-1-(4-(quinolin-7-yl)phenyl)ethyl)-1-oxa-4,9-diazaspiro[5.5]undecan-3-one

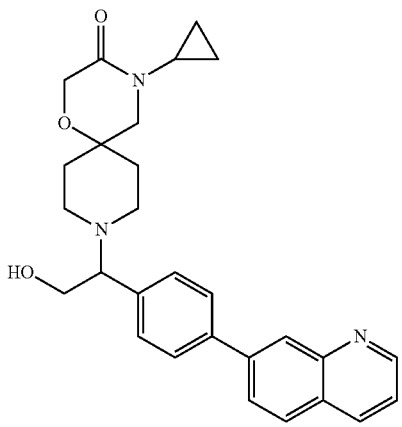

a) A solution of 4-cyclopropyl-1-oxa-4,9-diazaspiro[5.5]undecan-3-one (0.951 mmol) and 2-(4-bromophenyl)oxirane (0.951 mmol) in isopropanol (3 mL) was treated with nickel (II) acetate (0.048 mmol) (see Synlett 2004, 5, 846-850). The reaction mixture was stirred overnight at room temperature. The reaction was concentrated to dryness in vacuo, and the residue was purified by silica gel chromatography (0-9% methanol/dichloromethane). The desired intermediate was isolated as a 1:3 mixture (according to ¹H NMR) of regioisomers (109 mg, 0.266 mmol total). This mixture was diluted with 1,4-dioxane (2 mL) and was treated with 7-(4,4,5,5-tetramethyl-1,3,2-dioxaborolan-2-yl)quinoline (0.264 mmol), PdCl₂(dppf)-CH₂Cl₂ adduct (0.012 mmol) and 2M aq potassium carbonate (0.720 mmol). The reaction vessel was purged with nitrogen and sealed, and the mixture was irradiated in a Biotage Initiator Microwave at 120° C. for 15 min. The reaction mixture was diluted with water (50 mL) and its pH was adjusted to 3 using 1N aq HCl. The aqueous mixture was washed twice with ethyl acetate to remove some nonpolar impurities before the pH of the aqueous layer was adjusted to ~10 with 30% w/v aq ammonium hydroxide. The resulting basic solution was extracted three times with dichloromethane. The dichloromethane layers were combined, treated with Silicycle Si-thiol (50 mg), dried over sodium sulfate, filtered and concentrated in vacuo. Purification of the regioisomeric mixture by chiral HPLC (Chiralpak AS-H column, acetonitrile:methanol 9:1) followed by reverse phase HPLC (20-50% acetonitrile/water with 0.1% NH₄OH)

afforded the racemic title compound as a solid (13 mg, 3% yield). MS(ES)+ m/e 458.4 [M+H]+.

Example 23 methyl 3-(4-cyclopropyl-3-oxo-1-oxa-4,9-diazaspiro[5.5]undecan-9-yl)-3-(2-fluoro-4-(quinolin-7-yl)phenyl)propanoate

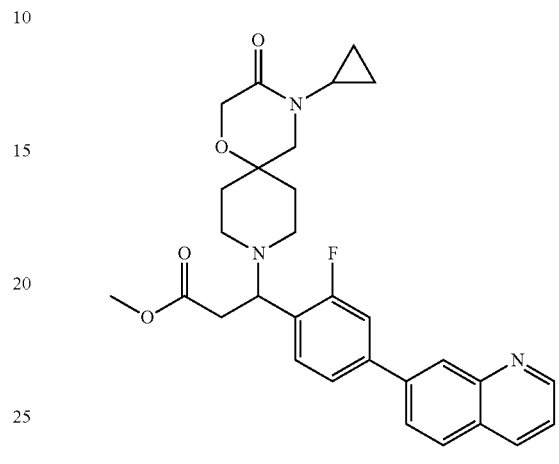

a) Methyl 3-(4-bromo-2-fluorophenyl)-3-(4-cyclopropyl-3-oxo-1-oxa-4,9-diazaspiro[5.5]undecan-9-yl)propanoate A suspension of 4-cyclopropyl-1-oxa-4,9-diazaspiro[5.5]undecan-3-one hydrochloride (4.05 mmol) in dichloromethane (10 mL) was treated with 1N aq NaOH (10.00 mmol) and was allowed to stir for 1 h, during which time the organic layer turned clear. The organic layer was partitioned from the aqueous layer, which was subsequently extracted with dichloromethane four times. The dichloromethane layers were combined, dried over sodium sulfate, filtered and concentrated in vacuo. This resulting residue was dissolved in dimethyl sulfoxide (7 mL) and was treated with 4-bromo-2-fluorobenzaldehyde (6.08 mmol), tert-butyl((1-methoxyvinyl)oxy)dimethylsilane (6.08 mmol) and trimethyl borate (8.11 mmol). The reaction was allowed to stir at room temperature for two days. At this point the reaction was slowly quenched with water (20 mL) and was stirred for one hour at room temperature. The solution was then extracted three times with ethyl acetate. The organic layers were combined, washed with brine, dried over sodium sulfate, filtered and concentrated in vacuo. The crude product was purified by silica gel chromatography (0-7% methanol/dichloromethane). The fractions containing the desired product were selected and concentrated in vacuo. The resulting oil was taken up in ethyl acetate (100 mL) and was washed three times with 30% w/v aq ammonium hydroxide, washed with brine, dried over sodium sulfate, filtered and concentrated to dryness in vacuo. The resulting oil was taken up in dichloromethane and concentrated to dryness in vacuo again to afford the title compound as a clear oil (1.148 g, 57% yield). MS(ES)+ m/e 469.2/471.2 [M+H]+ (bromide isotope pattern).

b) Methyl 3-(4-cyclopropyl-3-oxo-1-oxa-4,9-diazaspiro[5.5]undecan-9-yl)-3-(2-fluoro-4-(quinolin-7-yl)phenyl)propanoate A solution of methyl 3-(4-bromo-2-fluorophenyl)-3-(4-cyclopropyl-3-oxo-1-oxa-4,9-diazaspiro[5.5]undecan-9-yl)

propanoate (1.924 mmol) in 1,4-dioxane (6 mL) was treated with 7-(4,4,5,5-tetramethyl-1,3,2-dioxaborolan-2-yl)quinoline (2.116 mmol), PdCl₂(dppf)-CH₂Cl₂ adduct (0.096 mmol) and 2M aq potassium carbonate (5.77 mmol). The reaction vessel was purged with nitrogen and sealed, and the mixture was irradiated in a Biotage Initiator Microwave at 120° C. for 15 min. The resulting black mixture was diluted with water (50 mL) and extracted with dichloromethane three times. The combined organic layer was treated with Silicycle Si-thiol (100 mg), dried over sodium sulfate, filtered and concentrated in vacuo. Purification of the residue by silica gel chromatography (0-7% methanol/dichloromethane) afforded the title compound as a brown solid (802 mg, 72% yield). MS(ES)+ m/e 518.4 [M+H]⁺.

Example 24

4-cyclopropyl-9-(2-oxo-1-(4-(quinolin-7-yl)phenyl)propyl)-1-oxa-4,9-diazaspiro[5.5]undecan-3-one

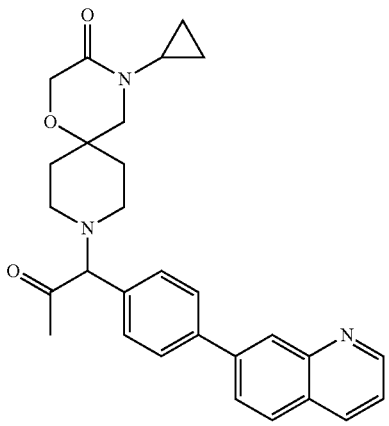 [SMILES: CC(=O)C(c1ccc(-c2ccc3cccnc3c2)cc1)N1CCC2(CC1)CN(C1CC1)C(=O)CO2]

a) 1-bromo-1-(4-bromophenyl)propan-2-one

A solution of 1-(4-bromophenyl)propan-2-one (1.173 mmol) in carbon tetrachloride (2.5 mL) was degassed with a stream of nitrogen for five minutes, at which point the solution was treated with N-bromosuccinimide (1.291 mmol) and azobisisobutyronitrile (0.059 mmol). The reaction vessel was purged with nitrogen and sealed, and the mixture was heated overnight at 80° C. with stirring. The resulting orange solution was concentrated to dryness in vacuo. Purification of the crude material by silica gel chromatography (0-35% ethyl acetate/hexanes) afforded the title compound (94 mg, 19%). ¹H NMR (400 MHz, DMSO-d₆) d ppm 2.27 (s, 3 H) 6.12 (s, 1 H) 7.39 (m, J=8.59 Hz, 2 H) 7.62 (d, J=8.59 Hz, 2 H).

b) 9-(1-(4-bromophenyl)-2-oxopropyl)-4-cyclopropyl-1-oxa-4,9-diazaspiro[5.5]undecan-3-one A solution of 1-bromo-1-(4-bromophenyl)propan-2-one (0.225 mmol) in N,N-dimethylformamide (1 mL) was treated with potassium carbonate (0.676 mmol) and 4-cyclopropyl-1-oxa-4,9-diazaspiro[5.5]undecan-3-one hydrochloride (0.237 mmol). The reaction mixture was stirred at room temperature overnight, at which point it was diluted with water (50 mL) and brine (20 mL). The aqueous mixture was extracted four times with dichloromethane. The organic layers were combined, dried over sodium sulfate, filtered and concentrated to dryness in vacuo to afford the crude title compound as a brown solid.

The crude solid was used directly in the next reaction. MS(ES)+ m/e 421.2/423.0 [M+H]⁺ (bromide isotope pattern).

c) 4-cyclopropyl-9-(2-oxo-1-(4-(quinolin-7-yl)phenyl)propyl)-1-oxa-4,9-diazaspiro[5.5]undecan-3-one A solution of the crude 9-(1-(4-bromophenyl)-2-oxopropyl)-4-cyclopropyl-1-oxa-4,9-diazaspiro[5.5]undecan-3-one from Example 24b in 1,4-dioxane (1.5 mL) was treated with 7-(4,4,5,5-tetramethyl-1,3,2-dioxaborolan-2-yl)quinoline (0.245 mmol), PdCl₂(dppf)-CH₂Cl₂ adduct (0.0113 mmol), and 2M aq potassium carbonate (0.668 mmol). The reaction vessel was purged with nitrogen and sealed, and the mixture irradiated in a Biotage
Initiator Microwave at 120° C. for 15 min. The resulting black mixture was diluted with water (50 mL) and extracted with dichloromethane three times. The combined organic layer was dried over sodium sulfate, filtered and concentrated in vacuo. Purification of the residue by silica gel chromatography (0-6% methanol/dichloromethane) followed by reverse phase HPLC (20-60% acetonitrile/water with 0.1% NH₄OH) afforded the title compound as a beige solid (38 mg, 34% yield over the two steps). MS(ES)+ m/e 470.3 [M+H]⁺.

Example 25

(+)-4-cyclopropyl-9-(1-(2-fluoro-4-(quinolin-7-yl)phenyl)-2-hydroxyethyl)-1-oxa-4,9-diazaspiro[5.5]undecan-3-one

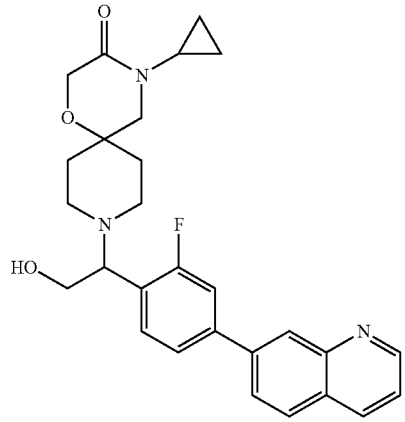 [SMILES: O=C1COC2(CCN(C(CO)c3ccc(-c4ccc5cccnc5c4)cc3F)CC2)CN1C1CC1]

a) 2-(4-bromo-2-fluorophenyl)ethanol

A solution of 2-(4-bromo-2-fluorophenyl)acetic acid (4.29 mmol) in 1M borane-tetrahydrofuran complex (20 mmol) was allowed to stir at room temperature for three days. At this point an additional portion of 1M borane-tetrahydrofuran complex (5 mmol) was added to the reaction. The reaction vessel was sealed and stirred at 50° C. for 3 h. The reaction was then allowed to cool to room temperature and was slowly quenched with the addition of 6N aq HCl (5 mL). The mixture was concentrated to dryness in vacuo and the crude material was diluted with ethyl acetate (200 mL). The organic mixture was washed twice with saturated aq sodium bicarbonate and once with brine. The organic layer was dried over sodium sulfate, filtered and concentrated to dryness in vacuo. Purification of the residue by silica gel chromatography (hexanes, then 0-60% ethyl acetate/hexanes) afforded the title compound as a semi-solid (660 mg, 63% yield). $^1$H NMR (400 MHz, DMSO-d$_6$) d ppm 2.72 (t, J=6.69 Hz, 2 H) 3.52-3.65 (m, 2 H) 4.74 (t, J=5.43 Hz, 1 H) 7.26-7.37 (m, 2 H) 7.47 (dd, J=9.73, 1.89 Hz, 1 H).

b) 4-bromo-2-fluorophenethyl acetate

A solution of 2-(4-bromo-2-fluorophenyl)ethanol (3.01 mmol) in dichloromethane (5 mL) and pyridine (10 mL) was treated with 4-(dimethylamino)pyridine (0.151 mmol) and acetic anhydride (9.04 mmol). The reaction was stirred overnight at room temperature. At this point the reaction was diluted with dichloromethane (100 mL). The organic layer was washed three times with 1N aq HCl, once with saturated aq sodium bicarbonate, and once with brine. The organic layer was dried over sodium sulfate, filtered and concentrated in vacuo to afford the title compound as a pale beige oil (710 mg, 81% yield). $^1$H NMR (400 MHz, DMSO-d$_6$) d ppm 1.96 (s, 3 H) 2.90 (t, J=6.44 Hz, 2 H) 4.20 (t, J=6.57 Hz, 2 H) 7.26-7.43 (m, 2 H) 7.51 (dd, J=9.73, 1.89 Hz, 1 H).

c) 2-bromo-2-(4-bromo-2-fluorophenyl)ethyl acetate

A solution of 4-bromo-2-fluorophenethyl acetate (2.72 mmol) in carbon tetrachloride (6 mL) was degassed with a stream of nitrogen for five minutes, at which point the solution was treated with N-bromosuccinimide (2.99 mmol) and azobisisobutyronitrile (0.272 mmol). The reaction vessel was purged with nitrogen and sealed, and the mixture stirred at 80° C. for 8 h, at which point the reaction was cooled to room temperature and was stirred overnight. The resulting mixture was concentrated to dryness in vacuo. Purification of the crude material by silica gel chromatography (0-50% ethyl acetate/hexanes) afforded the title compound as a beige oil (790 mg, 77% yield). $^1$H NMR (400 MHz, DMSO-d$_6$) d ppm 2.00 (s, 3 H) 4.57 (dd, J=11.62, 7.07 Hz, 1 H) 4.67 (dd, J=11.75, 7.20 Hz, 1 H) 5.52 (t, J=7.07 Hz, 1 H) 7.45-7.55 (m, 1 H) 7.59-7.70 (m, 2 H).

d) 2-(4-bromo-2-fluorophenyl)-2-(4-cyclopropyl-3-oxo-1-oxa-4,9-diazaspiro[5.5]undecan-9-yl)ethyl acetate A solution of 2-bromo-2-(4-bromo-2-fluorophenyl)ethyl acetate (0.971 mmol) in N,N-dimethylformamide (5 mL) was treated with potassium carbonate (2.91 mmol) and 4-cyclopropyl-1-oxa-4,9-diazaspiro[5.5]undecan-3-one hydrochloride (1.019 mmol). The reaction was allowed to stir at room temperature overnight. The reaction solution was then diluted with water (50 mL) and was extracted four times with ethyl acetate. The combined organic layer was washed four times with water, twice with brine, dried over sodium sulfate, filtered and concentrated in vacuo to afford the title compound as an oil (385 mg, 76% yield). MS(ES)+ m/e 469.1/471.2 [M+H]$^+$ (bromide isotope pattern).

e) 4-cyclopropyl-9-(1-(2-fluoro-4-(quinolin-7-yl) phenyl)-2-hydroxyethyl)-1-oxa-4,9-diazaspiro[5.5] undecan-3-one A solution of 2-(4-bromo-2-fluorophenyl)-2-(4-cyclopropyl-3-oxo-1-oxa-4,9-diazaspiro[5.5]undecan-9-yl)ethyl acetate (0.345 mmol) in 1,4-dioxane (1.5 mL) was treated with 7-(4,4,5,5-tetramethyl-1,3,2-dioxaborolan-2-yl)quinoline (0.380 mmol), PdCl$_2$(dppf)-CH$_2$Cl$_2$ adduct (0.017 mmol), and 2M aq potassium carbonate (1.035 mmol). The reaction vessel was purged with nitrogen and sealed, and the mixture irradiated in a Biotage Initiator Microwave at 120° C. for 15 min. The mixture was then concentrated to dryness in vacuo. The brown residue was diluted with ethanol (2 mL) and the solution was stirred in an oil bath at 50° C. overnight, after which the reaction was concentrated to dryness under a stream of nitrogen. The crude material was suspended in water (50 mL) and was extracted three times with ethyl acetate. The aqueous layer was further diluted with brine (20 mL) and was extracted once more with tetrahydrofuran. The organic layers (ethyl acetate and tetrahydrofuran) were combined, dried over sodium sulfate, filtered and concentrated in vacuo. Purification of the residue by silica gel chromatography (0-6% methanol/dichloromethane) and chiral HPLC (Chromegachiral CC$_4$, methanol) afforded the title compound as a white solid in >98% ee (21 mg, 12% yield). MS(ES)+ m/e 476.1 [M+H]$^+$. $\alpha_D$=+ 20 deg (c=0.04, methanol).

Example 26

(−)-4-cyclopropyl-9-(1-(2-fluoro-4-(quinolin-7-yl) phenyl)-2-hydroxyethyl)-1-oxa-4,9-diazaspiro[5.5] undecan-3-one a) From Example 25e, the title product was isolated as a white solid in >98% ee using chiral HPLC (Chromegachiral CC$_4$, methanol) followed by lyophilization from water (1 mL) (20 mg, 11% yield). MS(ES)+ m/e 476.1 [M+H]$^+$. $\alpha_D$=−22 deg (c=0.03, methanol).

Example 27

(+)-2-(4-cyclopropyl-3-oxo-1-oxa-4,9-diazaspiro [5.5]undecan-9-yl)-2-(2-fluoro-4-(quinolin-7-yl) phenyl)-N-methylacetamide

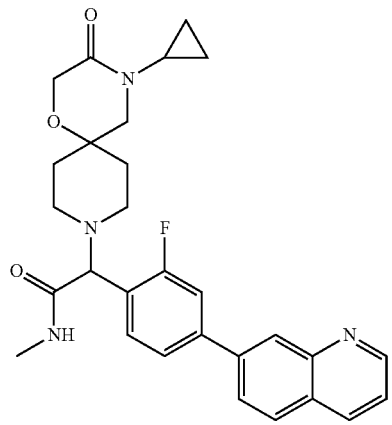 [SMILES: CNC(=O)C(c1ccc(-c2ccc3cccnc3c2)cc1F)N1CCC2(CC1)CN(C1CC1)C(=O)CO2]

a) 2-(4-bromo-2-fluorophenyl)-N-methylacetamide

A solution of 2-(4-bromo-2-fluorophenyl)acetic acid (10.56 mmol) in dichloromethane (20 mL) was treated with oxalyl chloride (31.7 mmol) and dimethylformamide (0.106 mmol). Effervescense was observed for fifteen minutes. When the bubbling had ceased, the reaction was concentrated to dryness in vacuo. The resulting oil was dissolved with dichloromethane and was concentrated to dryness in vacuo. The material was then diluted with tetrahydrofuran (20 mL) and was treated with methanamine (31.7 mmol) dropwise. Effervescense was again observed. A precipitate formed as the reaction was stirred over a two hour period. The contents of the reaction were concentrated to dryness in vacuo and were then dissolved in a minimal amount of methanol. Ethyl acetate was then added to this solution until a solid precipitated. The precipitate was collected by vacuum filtration. In a similar manner, two additional crops were collected from the mother liquor. The resulting solids were combined and triturated with dichloromethane. Purification of the solid by silica gel chromatography (0-5% methanol/dichloromethane) afforded the title compound as a white solid (610 mg, 22% yield). MS(ES)+ m/e 246.0/247.8 [M+H]$^+$ (bromide isotope pattern).

b) 2-bromo-2-(4-bromo-2-fluorophenyl)-N-methylacetamide

A solution of 2-(4-bromo-2-fluorophenyl)-N-methylacetamide (2.479 mmol) in carbon tetrachloride (5 mL) was degassed with a stream of nitrogen for five minutes, at which point the solution was treated with N-bromosuccinimide (2.73 mmol) and azobisisobutyronitrile (0.248 mmol). The reaction vessel was purged with nitrogen and sealed, and the mixture stirred at 80° C. overnight. After stirring overnight, the reaction was cooled to room temperature. The reaction mixture was degassed again with a stream of nitrogen for three minutes and was treated with N-bromosuccinimide (0.56 mmol) and azobisisobutyronitrile (0.124 mmol). The reaction vessel was purged with nitrogen and sealed, and the mixture stirred at 80° C. for two days. The reaction was then allowed to cool and was concentrated to dryness in vacuo. Purification of the residue by silica gel chromatography (0-50% ethyl acetate/hexanes) afforded the title compound as a white solid (296 mg, 33% yield). $^1$H NMR (400 MHz, DMSO-d$_6$) d ppm 2.65 (d, J=4.55 Hz, 3 H) 5.81 (s, 1 H) 7.49 (dd, J=8.59, 1.77 Hz, 1 H) 7.61 (dd, J=9.98, 1.89 Hz, 1 H) 7.72 (t, J=8.21 Hz, 1 H) 8.49 (br. s., 1 H).

c) 2-(4-bromo-2-fluorophenyl)-2-(4-cyclopropyl-3-oxo-1-oxa-4,9-diazaspiro[5.5]undecan-9-yl)-N-methylacetamide A solution of 2-bromo-2-(4-bromo-2-fluorophenyl)-N-methylacetamide (0.579 mmol) in N,N-dimethylformamide (3 mL) was treated with potassium carbonate (1.715 mmol) and 4-cyclopropyl-1-oxa-4,9-diazaspiro[5.5]undecan-3-one hydrochloride (0.632 mmol). The reaction was allowed to stir at room temperature overnight. The reaction solution was then diluted with water (50 mL) and was extracted three times with dichloromethane. The organic layers were combined and were washed with water three times, twice with brine, dried over sodium sulfate, filtered and concentrated in vacuo. Purification of the residue by silica gel chromatography (0-6% methanol/dichloromethane) afforded the title compound as a yellow oil (185 mg, 63% yield). MS(ES)+ m/e 454.0/455.9 [M+H]$^+$ (bromide isotope pattern).

d) (+)-2-(4-cyclopropyl-3-oxo-1-oxa-4,9-diazaspiro[5.5]undecan-9-yl)-2-(2-fluoro-4-(quinolin-7-yl)phenyl)-N-methylacetamide A solution of 2-(4-bromo-2-fluorophenyl)-2-(4-cyclopropyl-3-oxo-1-oxa-4,9-diazaspiro[5.5]undecan-9-yl)-N-methylacetamide (0.366 mmol) in 1,4-dioxane (2 mL) was treated with 7-(4,4,5,5-tetramethyl-1,3,2-dioxaborolan-2-yl)quinoline (0.403 mmol), PdCl$_2$(dppf)-CH$_2$Cl$_2$ adduct (0.018 mmol), and 2M aq potassium carbonate (1.099 mmol). The reaction vessel was purged with nitrogen and sealed, and the mixture irradiated in a Biotage Initiator Microwave at 120° C. for 15 min. The resulting black mixture was diluted with water (50 mL) and brine (20 mL), and extracted with dichloromethane four times. The combined organic layers were dried over sodium sulfate, filtered and concentrated in vacuo. The material was triturated with hexanes and the hexane solution was discarded. Purification of the residue by chiral HPLC (Chromegachiral CC$_4$, methanol) followed by lyophilization from water (w/25% acetonitrile) afforded the title compound as a beige solid in >98% ee (50 mg, 25% yield). MS(ES)+ m/e 503.1 [M+H]$^+$. $α_D$=+34 deg (c=0.04, methanol).

Example 28

(−)-2-(4-cyclopropyl-3-oxo-1-oxa-4,9-diazaspiro[5.5]undecan-9-yl)-2-(2-fluoro-4-(quinolin-7-yl)phenyl)-N-methylacetamide a) From Example 27d, the title product was isolated as a beige solid in >98% ee using chiral HPLC (Chromegachiral CC$_4$, methanol) followed by lyophilization from water (w/25% acetonitrile) (55 mg, 28% yield). MS(ES)+ m/e 503.1 [M+H]$^+$. $α_D$=−34 deg (c=0.03, methanol).

Example 29

(+)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide

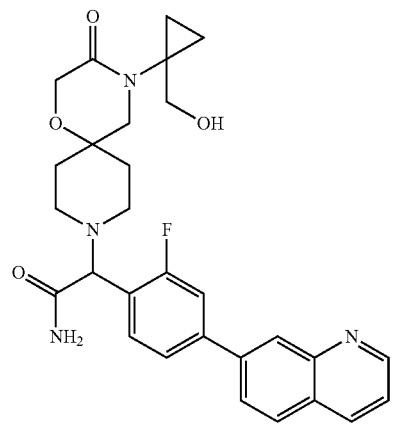 [SMILES: NC(=O)C(c1ccc(-c2ccc3cccnc3c2)cc1F)N1CCC2(CC1)CN(C1(CO)CC1)C(=O)CO2]

a) 1-(((tert-butyldimethylsilyl)oxy)methyl)cyclopropanamine

To a stirring solution of (1-aminocyclopropyl)methanol (9.69 mmol), 4-(dimethylamino)pyridine (0.484 mmol), and triethylamine (21.32 mmol) in anhydrous dichloromethane (25 mL) was added chloro(1,1-dimethylethyl)dimethylsilane (10.66 mmol). After stirring 20 h, the reaction was quenched with saturated aq ammonium chloride and extracted with dichloromethane. The extracts were washed with water, dried over magnesium sulfate, and concentrated under reduced pressure to afford the crude title compound (1.70 g, 78% yield) as a colorless liquid. MS(ES)+ m/e 202.2 [M+H]+.

b) tert-Butyl 4-(((1-(((tert-butyldimethylsilyl)oxy) methyl)cyclopropyl)amino)methyl)-4-hydroxypiperidine-1-carboxylate To a solution of 1-(((tert-butyldimethylsilyl)oxy)methyl) cyclopropanamine (10.09 mmol) in absolute ethanol (40 mL) was added tert-butyl 1-oxa-6-azaspiro[2.5]octane-6-carboxylate (9.61 mmol) in one portion. The reaction was heated at reflux for 20 h then cooled and evaporated onto silica. The solid was purified by flash chromatography (30-80% ethyl acetate in hexanes) to afford the title product (719 mg, 16% yield) as a colorless oil. MS(ES)+ m/e 415.5 [M+H]+.

c) tert-Butyl 4-((N-(1-(((tert-butyldimethylsilyl)oxy) methyl)cyclopropyl)-2-chloroacetamido)methyl)-4-hydroxypiperidine-1-carboxylate To a stirring solution of tert-butyl 4-(((1-(((tert-butyldimethylsilyl)oxy)methyl)cyclopropyl)amino)methyl)-4-hydroxypiperidine-1-carboxylate (1.688 mmol) and N,N-diisopropylethylamine (4.22 mmol) in anhydrous dichloromethane (30 mL) cooled to 0° C. was added neat chloroacetyl chloride (2.53 mmol). After 30 min, the reaction was diluted with saturated aq sodium bicarbonate and extracted with dichloromethane. The combined extracts were dried over magnesium sulfate and were evaporated onto silica. Purification of the solid by flash chromatography (30% ethyl acetate in hexanes) afforded the title product (742 mg, 85% yield) as a light orange oil. MS(ES)+ m/e 491.4 [M+H]+.

d) tert-Butyl 4-(1-(((tert-butyldimethylsilyl)oxy) methyl)cyclopropyl)-3-oxo-1-oxa-4,9-diazaspiro [5.5]undecane-9-carboxylate To a solution of tert-butyl 4-((N-(1-(((tert-butyldimethylsilyl)oxy)methyl)cyclopropyl)-2-chloroacetamido)methyl)-4-hydroxypiperidine-1-carboxylate (1.511 mmol) in anhydrous tetrahydrofuran (20 mL) was added 60% sodium hydride in mineral oil (3.02 mmol) in one portion. The suspension was heated at reflux for 1 h then cooled, quenched with water (1 mL), and evaporated to dryness in vacuo. Purification of the residue by flash chromatography (20-80% ethyl acetate in hexanes) afforded the title product (450 mg, 64% yield) as a colorless oil. MS(ES)+ m/e 455.3 [M+H]+. $^1$H NMR (400 MHz, CDCl$_3$) δ ppm 0.03 (s, 6 H) 0.76-0.98 (m, 13 H) 1.47 (s, 11 H) 1.70-1.89 (m, 2 H) 2.90-3.18 (m, 2 H) 3.35 (s, 2 H) 3.70 (br. s., 2 H) 3.85 (br. s., 2 H) 4.11 (s, 2 H).

e) 4-(1-(hydroxymethyl)cyclopropyl)-1-oxa-4,9-diazaspiro[5.5]undecan-3-one

A solution of tert-butyl 4-(1-(((tert-butyldimethylsilyl) oxy)methyl)cyclopropyl)-3-oxo-1-oxa-4,9-diazaspiro[5.5] undecane-9-carboxylate (0.988 mmol) in 1,4-dioxane (2 mL) was treated with 4N HCl in dioxane (8.00 mmol). The reaction was stirred at room temperature for 2.5 h. The reaction contents were then concentrated to dryness in vacuo, at which point it was determined that not all of the starting material had been consumed. The material was suspended in 1,4-dioxane (2 mL) and was treated with 4N HCl in dioxane (8.00 mmol). The mixture was allowed to stir at 50° C. for 2 h, at which point the reaction contents were concentrated to dryness in vacuo. The material was diluted with dichloromethane (5 mL) and was concentrated to dryness again to afford the crude title compound as a hydrochloride salt. The crude product was used directly in the next step. MS(ES)+ m/e 241.0 [M+H]+.

f) 2-(4-bromo-2-fluorophenyl)acetamide

To a solution of 4-bromo-1-(bromomethyl)-2-fluorobenzene (56.0 mmol) in ethanol (75.0 ml) and water (15.0 ml) was added sodium cyanide (67.2 mmol). The reaction was refluxed for 3 days then cooled and diluted with water. The solids were collected, slurried in water (100 mL) and 6N aq HCl (50 mL) for 1 h, and then filtered and dried via suction. The collected solids were slurried again in dichloromethane, and the solids were collected and dried to afford the title product (6.9 g, 52% yield) as a white solid. MS(ES)+ m/e 232.1, 233.9 [M+H]+. $^1$H NMR (400 MHz, DMSO-d6) δ ppm 3.43 (s, 2 H) 6.99 (br. s., 1 H) 7.28 (t, J=8.08 Hz, 1 H) 7.36 (dd, J=8.34, 2.02 Hz, 1 H) 7.47 (dd, J=9.60, 2.02 Hz, 1 H) 7.50 (br. s., 1 H).

g) 2-bromo-2-(4-bromo-2-fluorophenyl)acetamide

To a suspension of 2-(4-bromo-2-fluorophenyl)acetamide (29.7 mmol) and N-bromosuccinimide (37.2 mmol) in anhydrous carbon tetrachloride (85 ml) was added 2,2'-azobis(2-methylpropionitrile) (1.487 mmol). The reaction mixture was heated at 85° C. for 4 days. The resulting suspension was concentrated in vacuo and the residue was taken into brine and then extracted with ethyl acetate. The combined extracts were dried over sodium sulfate and decolorizing charcoal, filtered through a short pad of celite, and evaporated to a crude residue. Purification of the residue by flash chromatography (30% ethyl acetate in hexanes) afforded the title product (3.60 g, 38% yield) as a cream-colored solid. MS(ES)+m/e 310.1, 312.1 [M+H]+. $^1$H NMR (400 MHz, DMSO-d6) δ ppm 5.79 (s, 1 H) 7.48 (dd, J=8.59, 1.77 Hz, 1 H) 7.59 (br. s., 1 H) 7.61 (dd, J=9.85, 2.02 Hz, 1 H) 7.70 (t, J=8.21 Hz, 1 H) 7.91 (br. s., 1 H).

h) 2-(4-bromo-2-fluorophenyl)-2-(4-(1-(hydroxymethyl)cyclopropyl)-3-oxo-1-oxa-4,9-diazaspiro[5.5] undecan-9-yl)acetamide A solution of 2-bromo-2-(4-bromo-2-fluorophenyl)acetamide (1.037 mmol) in N,N-dimethylformamide (5 mL) was treated with potassium carbonate (2.96 mmol) and the crude 4-(1-(hydroxymethyl)cyclopropyl)-1-oxa-4,9-diazaspiro [5.5]undecan-3-one hydrochloride from Example 29a. The reaction was stirred at room temperature overnight. The reaction solution was then diluted with water (100 mL) and was extracted three times with ethyl acetate. The combined organic layers were washed three times with water, three times with brine, and was then dried over sodium sulfate, filtered and concentrated to dryness in vacuo to afford the crude title compound as a yellow oil (500 mg of 85% pure material as determined by $^1$H NMR, 91% yield over the two steps). MS(ES)+ m/e 470.1/472.0 [M+H]+ (bromide isotope pattern).

i) (+)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide A solution of crude (85% purity) 2-(4-bromo-2-fluorophenyl)-2-(4-(1-(hydroxymethyl)cyclopropyl)-3-oxo-1-oxa-4, 9-diazaspiro[5.5]undecan-9-yl)acetamide (0.488 mmol) in 1,4-dioxane (2 mL) was treated with 7-(4,4,5,5-tetramethyl-1,3,2-dioxaborolan-2-yl)quinoline (0.537 mmol), PdCl$_2$ (dppf)-CH₂Cl₂ adduct (0.024 mmol), and 2M aq potassium carbonate (1.464 mmol). The reaction vessel was purged with nitrogen and sealed, and the mixture irradiated in a Biotage Initiator Microwave at 120° C. for 15 min. Additional portions of 7-(4,4,5,5-tetramethyl-1,3,2-dioxaborolan-2-yl)quinoline (0.117 mmol) and PdCl₂(dppf)-CH₂Cl₂ adduct (0.012 mmol) were added. The reaction vessel was purged with nitrogen and sealed, and the mixture irradiated in a Biotage Initiator Microwave at 120° C. for 5 min. The resulting black mixture was diluted with water (50 mL) and brine (20 mL) and was extracted with ethyl acetate three times. The combined organic layers were treated with Silicycle Si-thiol (20 mg), dried over sodium sulfate, filtered and concentrated in vacuo. The resulting solid was purified by reverse phase HPLC (20-60% acetonitrile/water with 0.1% NH₄OH). Fractions containing the desired product were selected, combined and concentrated to dryness in vacuo. Further purification by chiral HPLC (Chromegachiral CC₄, methanol) followed by lyophilization from water (w/25% acetonitrile) afforded the title compound as a white solid in >98% ee (43 mg, 16% yield). MS(ES)+ m/e 519.3 [M+H]⁺. α_D=+47 deg (c=0.05, methanol).

Example 30

(−)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide a) From Example 29i, the title product was isolated as a white solid in >98% ee using chiral HPLC (Chromegachiral CC₄, methanol) followed by lyophilization from water (w/25% acetonitrile) (46 mg, 17% yield). MS(ES)+ m/e 519.3 [M+H]⁺. α_D=−32 deg (c=0.05, methanol).

Example 31

(+)-2-(4-cyclopropyl-3-oxo-1-oxa-4,9-diazaspiro[5.5]undecan-9-yl)-2-(2-fluoro-4-(2-methylquinolin-7-yl)phenyl)acetamide

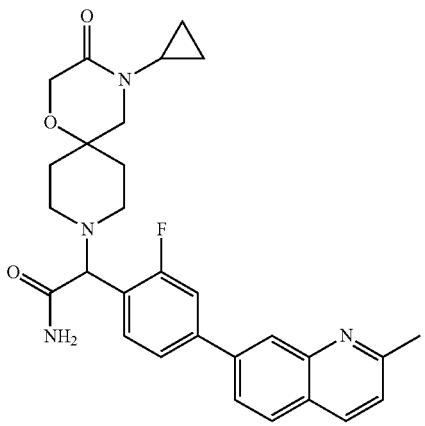 [SMILES: Cc1ccc2ccc(-c3ccc(C(C(N)=O)N4CCC5(CC4)CN(C4CC4)C(=O)CO5)c(F)c3)cc2n1]

a) A solution of 2-(4-bromo-2-fluorophenyl)-2-(4-cyclopropyl-3-oxo-1-oxa-4,9-diazaspiro[5.5]undecan-9-yl)acetamide (0.341 mmol) in dry 1,4-dioxane (1.5 mL) was treated with bis(pinacolato)diboron (0.409 mmol), potassium acetate (0.499 mmol) and PdCl₂(dppf)-CH₂Cl₂ adduct (0.017 mmol). The solution was degassed with a stream of nitrogen for three minutes, at which point the reaction vessel was purged with nitrogen and sealed, and the mixture stirred in an oil bath at 100° C. overnight. At this point the reaction was cooled to room temperature and 7-bromo-2-methylquinoline (0.341 mmol), PdCl₂(dppf)-CH₂Cl₂ adduct (0.017 mmol), and 2M aq potassium carbonate (1.022 mmol) were added. The reaction vessel was purged with nitrogen and sealed, and the mixture irradiated in a Biotage Initiator Microwave at 120° C. for 15 min. The resulting black mixture was diluted with water (100 mL) and brine (30 mL) and was extracted with ethyl acetate three times. The combined organic layers were treated with Silicycle Si-thiol (20 mg), dried over sodium sulfate, filtered and concentrated in vacuo. Purification of the residue by silica gel chromatography (0-9% methanol/dichloromethane) followed by chiral HPLC (Chromegachiral CC₄, methanol) and lyophilization from water (w/25% acetonitrile) afforded the title compound as a white solid in >98% ee (38 mg, 21% yield). MS(ES)+ m/e 503.0 [M+H]⁺. α_D=+48 deg (c=0.04, methanol).

Example 32

(−)-2-(4-cyclopropyl-3-oxo-1-oxa-4,9-diazaspiro[5.5]undecan-9-yl)-2-(2-fluoro-4-(2-methylquinolin-7-yl)phenyl)acetamide a) From Example 31a, the title product was isolated as a white solid in >98% ee using chiral HPLC (Chromegachiral CC₄, methanol) followed by lyophilization from water (w/25% acetonitrile) (38 mg, 21% yield). MS(ES)+ m/e 503.0 [M+H]⁺. α_D=−27 deg (c=0.04, methanol).

Example 33

2-(4-cyclopropyl-3-oxo-1-oxa-4,9-diazaspiro[5.5]undecan-9-yl)-2-(3-fluoro-4'-methoxy-[1,1'-biphenyl]-4-yl)acetamide

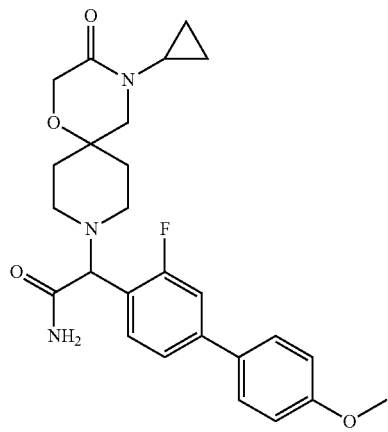 [SMILES: COc1ccc(-c2ccc(C(C(N)=O)N3CCC4(CC3)CN(C3CC3)C(=O)CO4)c(F)c2)cc1]

a) A solution of 2-(4-bromo-2-fluorophenyl)-2-(4-cyclopropyl-3-oxo-1-oxa-4,9-diazaspiro[5.5]undecan-9-yl)acetamide (0.341 mmol) in dry 1,4-dioxane (1.5 mL) was treated with (4-methoxyphenyl)boronic acid (0.375 mmol), PdCl₂(dppf)-CH₂Cl₂ adduct (0.017 mmol) and 2M aq potassium carbonate (1.022 mmol). The solution was degassed with a stream of nitrogen for three minutes, at which point the reaction vessel was purged with nitrogen and sealed, and the mixture irradiated in a Biotage Initiator Microwave at 120° C. for 15 min. The resulting black mixture was diluted with water (50 mL) and was extracted with dichloromethane three times. The combined organic layers were treated with Silicycle Si-thiol (20 mg), dried over sodium sulfate, filtered and concentrated in vacuo.

The crude material was purified by silica gel chromatography (0-6% methanol/dichloromethane) followed by reverse phase HPLC (20-60% acetonitrile/water with 0.1% NH$_4$OH). Fractions containing the desired product were selected, combined and concentrated to dryness in vacuo. Lyophilization of the product from water (w/25% acetonitrile) afforded the title compound as a white solid (87 mg, 51% yield). MS(ES)+m/e 468.2 [M+H]$^+$.

Example 34

2-(4-cyclopropyl-3-oxo-1-oxa-4,9-diazaspiro[5.5]undecan-9-yl)-2-(2-fluoro-4-(2-hydroxyquinolin-7-yl)phenyl)acetamide

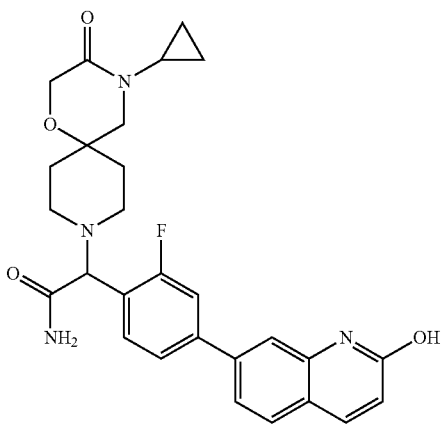 [SMILES: NC(=O)C(c1ccc(-c2ccc3ccc(O)nc3c2)cc1F)N1CCC2(CC1)CN(C1CC1)C(=O)CO2]

a) A solution of 2-(4-bromo-2-fluorophenyl)-2-(4-cyclopropyl-3-oxo-1-oxa-4,9-diazaspiro[5.5]undecan-9-yl)acetamide (0.341 mmol) in dry 1,4-dioxane (1.5 mL) was treated with bis(pinacolato)diboron (0.409 mmol), potassium acetate (0.499 mmol) and PdCl$_2$(dppf)-CH$_2$Cl$_2$ adduct (0.017 mmol). The solution was degassed with a stream of nitrogen for three minutes, at which point the reaction vessel was purged with nitrogen and sealed, and the mixture heated in an oil bath at 100° C. overnight. The black solution was allowed to cool to room temperature, at which point 7-chloroquinolin-2-ol (0.341 mmol), PdCl$_2$(dppf)-CH$_2$Cl$_2$ adduct (0.017 mmol), and 2M aq potassium carbonate (1.022 mmol) were added. The reaction vessel was purged with nitrogen and sealed, and the mixture irradiated in a Biotage Initiator Microwave at 120° C. for 15 min. Due to incomplete conversion of the starting material, the reaction solution was treated with an additional portion of PdCl$_2$(dppf)-CH$_2$Cl$_2$ adduct (0.017 mmol), at which point the reaction vessel was purged with nitrogen and sealed, and the mixture stirred in an oil bath at 100° C. for 60 h. At this point the reaction was cooled to room temperature before it was treated again with PdCl$_2$(dppf)-CH$_2$Cl$_2$ adduct (0.017 mmol), purged with nitrogen, sealed and stirred in an oil bath at 120° C. overnight. The reaction was cooled to room temperature and was diluted with water (50 mL) and brine (10 mL). The mixture was extracted five times with ethyl acetate. The combined organic layers were treated with Si-Thiol (100 mg), dried over sodium sulfate, filtered and concentrated in vacuo. The crude material was purified by silica gel chromatography (0-9% methanol/dichloromethane), by reverse phase HPLC (20-60% acetonitrile/water with 0.1% NH$_4$OH), and by reverse phase HPLC (5-35% acetonitrile with 0.1% TFA/water with 0.1% TFA). Fractions containing the desired product were combined and the pH of the resulting mixture was adjusted to ~10 with 30% w/v aq ammonium hydroxide. This mixture was concentrated to a minimal volume in vacuo and was then extracted with ethyl acetate three times. The combined organic layers were dried over sodium sulfate, filtered and concentrated in vacuo. Lyophilization of the product from water (w/25% acetonitrile) afforded the title compound as a white solid (15 mg, 8% yield). MS(ES)+ m/e 505.3 [M+H]$^+$.

Example 35

2-(4-cyclopropyl-3-oxo-1-oxa-4,9-diazaspiro[5.5]undecan-9-yl)-2-(3,4'-difluoro-[1,1'-biphenyl]-4-yl)acetamide

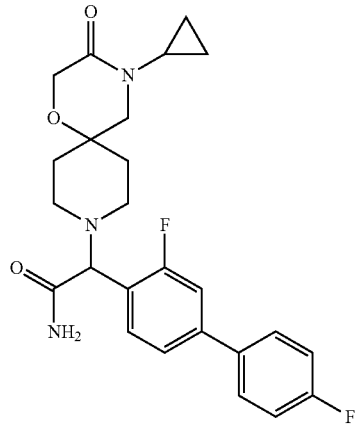 [SMILES: NC(=O)C(c1ccc(-c2ccc(F)cc2)cc1F)N1CCC2(CC1)CN(C1CC1)C(=O)CO2]

a) A solution of 2-(4-bromo-2-fluorophenyl)-2-(4-cyclopropyl-3-oxo-1-oxa-4,9-diazaspiro[5.5]undecan-9-yl)acetamide (0.341 mmol) in dry 1,4-dioxane (1.5 mL) was treated with (4-fluorophenyl)boronic acid (0.375 mmol), PdCl$_2$(dppf)-CH$_2$Cl$_2$ adduct (0.017 mmol) and 2M aq potassium carbonate (1.022 mmol). The solution was degassed with a stream of nitrogen for three minutes, at which point the reaction vessel was purged with nitrogen and sealed, and the mixture irradiated in a Biotage Initiator Microwave at 120° C. for 15 min. The resulting black mixture was diluted with water (50 mL) and extracted three times with ethyl acetate. The combined organic layers were treated with Silicycle Si-thiol (20 mg), dried over sodium sulfate, filtered and concentrated in vacuo. The crude material was purified by reverse phase HPLC (20-65% acetonitrile/water with 0.1% NH$_4$OH) and by reverse phase HPLC (10-50% acetonitrile with 0.1% TFA/water with 0.1% TFA). Fractions containing the desired product were combined and the pH of the resulting mixture was adjusted to ~10 with 30% w/v aq ammonium hydroxide. This mixture was concentrated to a minimal volume in vacuo and was then extracted with dichloromethane three times. The combined organic layers were dried over sodium sulfate, filtered and concentrated in vacuo. Lyophilization of the

Example 36

(+)-2-(4-cyclopropyl-3-oxo-1-oxa-4,9-diazaspiro[5.5]undecan-9-yl)-2-(2-fluoro-4-(quinolin-7-yl)phenyl)-N-hydroxyacetamide

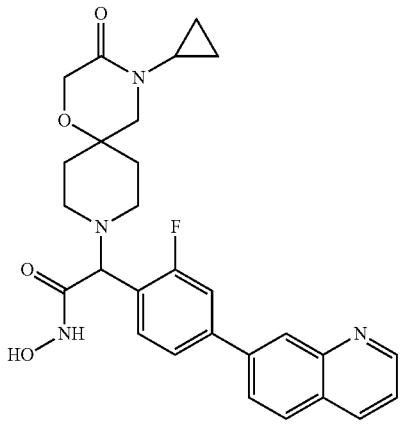 [SMILES: O=C(NO)C(c1ccc(-c2ccc3cccnc3c2)cc1F)N1CCC2(CC1)CN(C1CC1)C(=O)CO2]

a) 2-(4-bromo-2-fluorophenyl)acetonitrile

To a solution of 4-bromo-1-(bromomethyl)-2-fluorobenzene (56.0 mmol) in ethanol (75.0 ml) and water (15.0 ml) was added sodium cyanide (67.2 mmol). The reaction was refluxed for 3 days then cooled and diluted with water. The solids were collected, slurried in water (100 mL) and 6N aq HCl (50 mL) for 1 h, and then filtered and dried via suction. The collected solids were slurried again in dichloromethane, and the solids were collected and dried to afford 2-(4-bromo-2-fluorophenyl)acetamide (6.9 g, 52% yield) as a white solid. The dichloromethane filtrate was evaporated to afford a crude mixture (72% purity by LCMS) of the title product and 2-(4-bromo-2-fluorophenyl)acetamide (1.4:1 ratio) as a light yellow solid (4.5 g). A portion of this mixture was used directly in the next step. Title product: MS(ES)+ m/e 214.0, 216.2 [M+H]$^+$.

b) Methyl 2-(4-bromo-2-fluorophenyl)acetate

A solution of a crude (72% purity) mixture of 2-(4-bromo-2-fluorophenyl)acetonitrile and 2-(4-bromo-2-fluorophenyl)acetamide (1.4:1 ratio, 2.0 g) in methanol (6 mL) was treated dropwise with conc. sulfuric acid (4 mL, 75 mmol). The vessel was then sealed, heated in an oil bath at 80° C., and stirred for three days. At this point the reaction was cooled to room temperature and was diluted slowly with water (50 mL). The mixture was then extracted twice with dichloromethane. The organic layers were combined and washed with saturated aq sodium bicarbonate and brine. The organic solution was dried over sodium sulfate, filtered and concentrated in vacuo to afford the crude title compound as a clear oil. The crude oil was used directly in the next reaction. $^1$H NMR (400 MHz, DMSO-d$_6$) δ ppm 3.63 (s, 3 H) 3.74 (s, 2 H) 7.34 (t, J=8.08 Hz, 1 H) 7.38-7.43 (m, 1 H) 7.55 (dd, J=9.60, 2.02 Hz, 1 H).

c) Methyl 2-bromo-2-(4-bromo-2-fluorophenyl)acetate

A solution of the crude methyl 2-(4-bromo-2-fluorophenyl)acetate from Example 36b in carbon tetrachloride (15 mL) was degassed with a stream of nitrogen for 5 min. This solution was then treated with N-bromosuccinimide (10.37 mmol) and azobisisobutyronitrile (0.944 mmol). The reaction vessel was purged with nitrogen and sealed, and the mixture was stirred in an oil bath at 80° C. overnight. The reaction was then cooled and was concentrated to dryness in vacuo. Purification of the residue by silica gel chromatography (0-30% ethyl acetate/hexanes) afforded the title compound (2.5 g). $^1$H NMR (400 MHz, DMSO-d$_6$) δ ppm 3.74 (s, 3 H) 6.19 (s, 1 H) 7.47-7.58 (m, 2 H) 7.66 (dd, J=10.11, 1.77 Hz, 1 H).

d) Methyl 2-(4-bromo-2-fluorophenyl)-2-(4-cyclopropyl-3-oxo-1-oxa-4,9-diazaspiro[5.5]undecan-9-yl)acetate A solution of methyl 2-bromo-2-(4-bromo-2-fluorophenyl)acetate (7.29 mmol) in N,N-dimethylformamide (30 mL) was treated with potassium carbonate (19.90 mmol) and 4-cyclopropyl-1-oxa-4,9-diazaspiro[5.5]undecan-3-one hydrochloride (8.31 mmol). The reaction was stirred at room temperature for two days. The reaction solution was diluted with water (200 mL) and was extracted three times with ethyl acetate. The combined organic layers were washed five times with water and three times with brine. The organic solution was dried over sodium sulfate, filtered and concentrated in vacuo. The resulting semi-solid was diluted with dichloromethane (10 mL) and was concentrated to dryness in vacuo. This was repeated twice, at which point the resulting solid was dried under high vacuum overnight, affording the title compound as a white solid (3.05 g, 87% yield). MS(ES)+ m/e 454.8/456.9 [M+H]$^+$ (bromide isotope pattern).

e) Methyl 2-(4-cyclopropyl-3-oxo-1-oxa-4,9-diazaspiro[5.5]undecan-9-yl)-2-(2-fluoro-4-(quinolin-7-yl)phenyl)acetate A solution of methyl 2-(4-bromo-2-fluorophenyl)-2-(4-cyclopropyl-3-oxo-1-oxa-4,9-diazaspiro[5.5]undecan-9-yl)acetate (2.53 mmol) in 1,4-dioxane (8 mL) was treated with 7-(4,4,5,5-tetramethyl-1,3,2-dioxaborolan-2-yl)quinoline (2.78 mmol), PdCl$_2$(dppf)-CH$_2$Cl$_2$ adduct (0.126 mmol), and 2M aq potassium carbonate (7.58 mmol). The reaction vessel was purged with nitrogen and sealed, and the mixture irradiated in a Biotage Initiator Microwave at 120° C. for 15 min. The resulting black mixture was diluted with water (100 mL) and brine (20 mL) and was extracted three times with ethyl acetate. The combined organic layers were washed with brine, dried over sodium sulfate, filtered and concentrated in vacuo. Purification of the residue by silica gel chromatography (0-5% methanol/dichloromethane) afforded the desired product, which was dissolved with dichloromethane and concentrated in vacuo three times to afford the title compound as a brown gel (1.21 grams, 81% yield). MS(ES)+ m/e 504.1 [M+H]$^+$.

f) (+)-2-(4-cyclopropyl-3-oxo-1-oxa-4,9-diazaspiro[5.5]undecan-9-yl)-2-(2-fluoro-4-(quinolin-7-yl)phenyl)-N-hydroxyacetamide A solution of methyl 2-(4-cyclopropyl-3-oxo-1-oxa-4,9-diazaspiro[5.5]undecan-9-yl)-2-(2-fluoro-4-(quinolin-7-yl)phenyl)acetate (0.560 mmol) in methanol (2 mL) and tetrahydrofuran (2 mL) was treated with potassium hydroxide (1.782 mmol) and hydroxylamine (50% w/v in water, 8.16 mmol). The reaction mixture was stirred at room temperature for 3 h. The reaction solution was then concentrated to dryness under a stream of nitrogen. Purification of the residue by reverse phase HPLC (20-60% acetonitrile/water with 0.1% $NH_4OH$) followed by chiral HPLC (Chiralpak AS-H column, acetonitrile:methanol 98:2) and lyophilization from water (w/25% acetonitrile) afforded the title compound as a white solid (20 mg, 6%). MS(ES)+ m/e 504.9 [M+H]+, >99% ee, $\alpha_D$=+17 deg (c=0.02, acetonitrile:methanol 98:2).

Example 37

(−)-2-(4-cyclopropyl-3-oxo-1-oxa-4,9-diazaspiro [5.5]undecan-9-yl)-2-(2-fluoro-4-(quinolin-7-yl) phenyl)-N-hydroxyacetamide a) From Example 36f, the title product was isolated as a white solid in >98% ee using chiral HPLC (Chiralpak AS-H column, acetonitrile:methanol 98:2) followed by lyophilization from water (w/25% acetonitrile) (21 mg, 7% yield). MS(ES)+ m/e 505.0 [M+H]+. $\alpha_D$=−18 deg (c=0.014, acetonitrile:methanol 98:2).

Example 38

(+)-4-cyclopropyl-9-(1-(2,6-difluoro-4-(quinolin-7-yl)phenyl)-2-hydroxyethyl)-1-oxa-4,9-diazaspiro [5.5]undecan-3-one

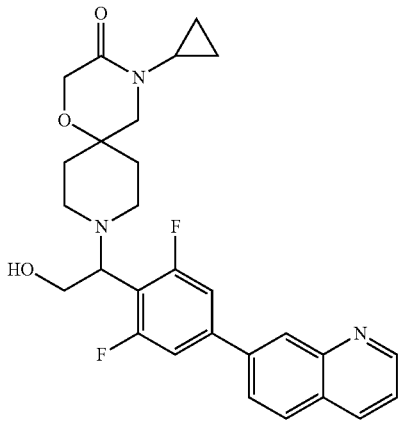 [SMILES: O=C1COC2(CCN(C(CO)c3c(F)cc(-c4ccc5cccnc5c4)cc3F)CC2)CN1C1CC1]

a) 2-(4-bromo-2,6-difluorophenyl)acetic acid

A suspension of 2-(4-bromo-2,6-difluorophenyl)acetamide (7.20 mmol) in ethanol (10 mL) was treated with 6N aq sodium hydroxide (90 mmol) at room temperature. The vessel was then stirred in an oil bath at 80° C. After one hour the reaction mixture had turned clear. After stirring overnight, the reaction mixture was cooled to room temperature, at which point the pH was adjusted to ~1 with 6N aq HCl. A white precipitate formed, and the solution was concentrated to a volume of ~10 mL, at which point it was extracted three times with ethyl acetate. The combined organic layers were washed twice with brine, dried over sodium sulfate, filtered and concentrated in vacuo to afford the title compound as a solid (837 mg, 41% yield). $^1$H NMR (400 MHz, DMSO-$d_6$) δ ppm 3.60 (s, 2 H) 7.49 (d, J=6.82 Hz, 2 H) 12.82 (br. s., 1 H).

b) 2-(4-bromo-2,6-difluorophenyl)ethanol

A solution of 2-(4-bromo-2,6-difluorophenyl)acetic acid (2.131 mmol) in borane-tetrahydrofuran complex (1M, 20.00 mmol) was stirred in an oil bath at 40° C. for two days. At this point, the reaction contents were concentrated to dryness in vacuo. The material was resuspended in water (50 mL) and was extracted three times with ethyl acetate. The combined organic layers were washed twice with saturated aq sodium bicarbonate and once with brine, and were dried over sodium sulfate, filtered and concentrated in vacuo. Purification of the residue by silica gel chromatography (0-50% ethyl acetate/ hexanes) afforded the title compound as a clear oil (330 mg, 58% yield). $^1$H NMR (400 MHz, DMSO-$d_6$) δ ppm 2.74 (t, J=6.82 Hz, 2 H) 3.46-3.60 (m, 2 H) 4.83 (t, J=5.68 Hz, 1 H) 7.35-7.49 (m, 2 H).

c) 4-bromo-2,6-difluorophenethyl acetate

A solution of 2-(4-bromo-2,6-difluorophenyl)ethanol (1.392 mmol) in dichloromethane (2 mL) was treated with pyridine (4.00 mL), acetic anhydride (4.18 mmol), and 4-(dimethylamino)pyridine (0.070 mmol). The reaction was stirred at room temperature for three days. At this point, the reaction contents were concentrated to in vacuo to minimum volume. The material was diluted with water (50 mL) and was extracted twice with ethyl acetate. The combined organic layers were washed with saturated aq sodium bicarbonate, twice with brine, dried over sodium sulfate, filtered and concentrated in vacuo to afford the title compound as a beige oil (330 mg, 76% yield). $^1$H NMR (400 MHz, DMSO-$d_6$) δ ppm 1.95 (s, 3 H) 2.91 (t, J=6.32 Hz, 2 H) 4.18 (t, J=6.44 Hz, 2 H) 7.47 (d, J=7.07 Hz, 2 H).

d) 2-bromo-2-(4-bromo-2,6-difluorophenyl)ethyl acetate

A solution of 4-bromo-2,6-difluorophenethyl acetate (1.182 mmol) in carbon tetrachloride (3 mL) was degassed with a stream of nitrogen for 5 min and was then treated with N-bromosuccinimide (1.301 mmol) and azobisisobutyronitrile (0.118 mmol). The reaction vessel was purged with nitrogen and sealed, and the mixture was stirred in an oil bath at 80° C. overnight. The reaction was then cooled and was concentrated to dryness under a stream of nitrogen. The crude material was dissolved in ethyl acetate (50 mL) and was washed twice with water. The organic layer was then dried over sodium sulfate, filtered and concentrated in vacuo. The product was dissolved in dichloromethane and was again concentrated to dryness in vacuo to afford the title compound as a yellow oil (403 mg, 86% yield). $^1$H NMR (400 MHz, DMSO-$d_6$) δ ppm 2.01 (s, 3 H) 4.55-4.70 (m, 2 H) 5.50 (t, J=7.45 Hz, 1 H) 7.55-7.67 (m, 2 H).

e) 2-(4-bromo-2,6-difluorophenyl)-2-(4-cyclopropyl-3-oxo-1-oxa-4,9-diazaspiro[5.5]undecan-9-yl)ethyl acetate A solution of 2-bromo-2-(4-bromo-2,6-difluorophenyl) ethyl acetate (1.013 mmol) in N,N-dimethylformamide (5 mL) was treated with potassium carbonate (3.04 mmol) and 4-cyclopropyl-1-oxa-4,9-diazaspiro[5.5]undecan-3-one hydrochloride (1.115 mmol). The reaction was stirred at room temperature overnight. The reaction solution was diluted with water (100 mL) and was extracted three times with diethyl ether. The combined organic layers were washed with brine, dried over sodium sulfate, filtered and concentrated in vacuo to afford the crude title compound as a yellow solid (405 mg of 80% pure material as estimated by $^1$H NMR, 65% yield). MS(ES)+ m/e 487.2/489.3 [M+H]+ (bromide isotope pattern).

f) (+)-4-cyclopropyl-9-(1-(2,6-difluoro-4-(quinolin-7-yl)phenyl)-2-hydroxyethyl)-1-oxa-4,9-diazaspiro[5.5]undecan-3-one A solution of crude (80% purity) 2-(4-bromo-2,6-difluorophenyl)-2-(4-cyclopropyl-3-oxo-1-oxa-4,9-diazaspiro[5.5]undecan-9-yl)ethyl acetate (0.361 mmol) in 1,4-dioxane (2 mL) was treated with 7-(4,4,5,5-tetramethyl-1,3,2-dioxaborolan-2-yl)quinoline (0.397 mmol), PdCl$_2$(dppf)-CH$_2$Cl$_2$ adduct (0.018 mmol), and 2M aq potassium carbonate (1.083 mmol). The reaction vessel was purged with nitrogen and sealed, and the mixture irradiated in a Biotage Initiator Microwave at 120° C. for 15 min. The reaction was cooled at which point additional portions of 7-(4,4,5,5-tetramethyl-1,3,2-dioxaborolan-2-yl)quinoline (0.08 mmol) and PdCl$_2$(dppf)-CH$_2$Cl$_2$ adduct (0.006 mmol) were added. The reaction vessel was purged with nitrogen and sealed, and the mixture irradiated in a Biotage Initiator Microwave at 120° C. for 5 min. The black reaction mixture was then concentrated to minimal volume (~0.5 mL) under a stream of nitrogen at which point it was diluted with a mixture of ethanol and water (2 mL, 1:1). This mixture was stirred in an oil bath at 80° C. overnight. The resulting solution was concentrated to dryness under a stream of nitrogen and then diluted with water (50 mL) and brine (20 mL). This aqueous mixture was extracted four times with ethyl acetate. The combined organic layers were treated with Silicycle Si-thiol (50 mg), dried over sodium sulfate, filtered and concentrated in vacuo. Purification of the residue by silica gel chromatography (0-7% methanol/dichloromethane) and chiral HPLC (Chromegachiral CC$_4$, methanol) followed by lyophilization from water (w/25% acetonitrile) afforded the title compound as a white solid in >99% ee (29 mg, 15% yield). MS(ES)+ m/e 494.1 [M+H]$^+$. $\alpha_D$=+4 deg (c=0.06, methanol).

Example 39

(−)-4-cyclopropyl-9-(1-(2,6-difluoro-4-(quinolin-7-yl)phenyl)-2-hydroxyethyl)-1-oxa-4,9-diazaspiro[5.5]undecan-3-one a) From Example 38f, the title product was isolated as a white solid in >98% ee using chiral HPLC (Chromegachiral CC$_4$, methanol) followed by lyophilization from water (w/25% acetonitrile) (32 mg, 17% yield). MS(ES)+ m/e 494.1 [M+H]$^+$. $\alpha_D$=−5 deg (c=0.09, methanol).

Example 40

(+)-2-(4-cyclopropyl-3-oxo-1-oxa-4,9-diazaspiro[5.5]undecan-9-yl)-2-(2-fluoro-4-(quinolin-5-yl)phenyl)acetamide

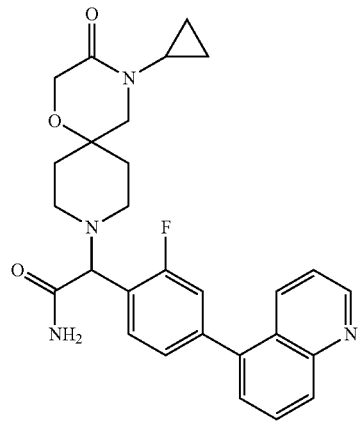 [SMILES: NC(=O)C(c1ccc(-c2cccc3ncccc23)cc1F)N1CCC2(CC1)CN(C1CC1)C(=O)CO2]

a) A solution of 2-(4-bromo-2-fluorophenyl)-2-(4-cyclopropyl-3-oxo-1-oxa-4,9-diazaspiro[5.5]undecan-9-yl)acetamide (0.273 mmol) in dry 1,4-dioxane (1.5 mL) was treated with quinolin-5-ylboronic acid (0.300 mmol), PdCl$_2$(dppf)-CH$_2$Cl$_2$ adduct (0.014 mmol) and 2M aq potassium carbonate (0.818 mmol). The reaction vessel was purged with nitrogen and sealed, and the mixture irradiated in a Biotage Initiator Microwave at 120° C. for 15 min. The resulting black mixture was diluted with water (50 mL) and brine (20 mL) and was extracted with ethyl acetate three times. The combined organic layers were washed with brine, dried over sodium sulfate, filtered and concentrated in vacuo. Purification of the residue by silica gel chromatography (0-9% methanol/dichloromethane) and chiral HPLC (Chromegachiral CC$_4$, methanol) followed by lyophilization from water (w/25% acetonitrile) afforded the title compound as a white solid in >99% ee (30 mg, 21% yield). MS(ES)+ m/e 489.5 [M+H]$^+$, $\alpha_D$=+38 deg (c=0.05, methanol).

Example 41

(−)-2-(4-cyclopropyl-3-oxo-1-oxa-4,9-diazaspiro[5.5]undecan-9-yl)-2-(2-fluoro-4-(quinolin-5-yl)phenyl)acetamide a) From Example 40a, the title product was isolated as a white solid in >99% ee using chiral HPLC (Chiralpak Chromegachiral CC$_4$, methanol) followed by lyophilization from water (w/25% acetonitrile) (31 mg, 22% yield). MS(ES)+ m/e 489.5 [M+H]$^+$, $\alpha_D$=−38 deg (c=0.05, methanol).

Example 42

(−)-2-(4-cyclopropyl-3-oxo-1-oxa-4,9-diazaspiro[5.5]undecan-9-yl)-2-(2-fluoro-4-(quinolin-7-yl)phenyl)-N,N-dimethylacetamide

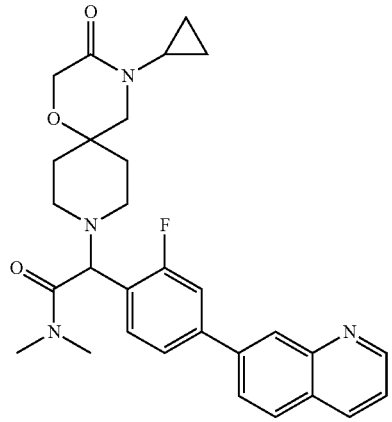 [SMILES: CN(C)C(=O)C(c1ccc(-c2ccc3cccnc3c2)cc1F)N1CCC2(CC1)CN(C1CC1)C(=O)CO2]

a) A solution of 2-(4-cyclopropyl-3-oxo-1-oxa-4,9-diazaspiro[5.5]undecan-9-yl)-2-(2-fluoro-4-(quinolin-7-yl)phenyl)acetic acid (0.153 mmol) in dichloromethane (1 mL) was treated with N-(3-dimethylaminopropyl)-N'-ethylcarbodiimide hydrochloride (0.230 mmol) and 4-(dimethylamino)pyridine (0.766 mmol). This mixture was stirred at room temperature for 10 min at which point dimethylamine hydrochloride (0.306 mmol) was added. The reaction vessel was sealed and the reaction was stirred at room temperature overnight. At this point an additional portion of N-(3-Dimethylaminopropyl)-N'-ethylcarbodiimide hydrochloride (0.230 mmol) was added. The reaction vessel was sealed and the reaction was stirred at room temperature overnight. The resulting reaction mixture was concentrated to dryness under a stream of nitrogen. Purification of the residue by reverse phase HPLC (20-65% acetonitrile/water with 0.1% NH$_4$OH) followed by chiral HPLC (Chromegachiral CC$_4$, methanol) and lyophilization from water (w/25% acetonitrile) afforded the title compound as a solid (25 mg, 30%). MS(ES)+ m/e 517.4 [M+H]$^+$, >99% ee, $\alpha_D$=−69 deg (c=0.01, methanol).

Example 43

(+)-2-(4-cyclopropyl-3-oxo-1-oxa-4,9-diazaspiro [5.5]undecan-9-yl)-2-(2-fluoro-4-(quinolin-7-yl) phenyl)-N,N-dimethylacetamide a) From Example 42a, the title product was isolated as a solid in >99% ee using chiral HPLC (Chiralpak Chromegachiral CC$_4$, methanol) followed by trituration with hexanes, reverse phase HPLC (Kromasil silica gel, dichloromethane: methanol 95:5), and lyophilization from water (w/25% acetonitrile) (17 mg, 20% yield). MS(ES)+ m/e 517.5 [M+H]$^+$. $\alpha_D$=+68 deg (c=0.02, methanol).

Example 44

(+)-2-(4-cyclopropyl-3-oxo-1-oxa-4,9-diazaspiro [5.5]undecan-9-yl)-2-(2-fluoro-4-(2-methylquinolin-5-yl)phenyl)acetamide

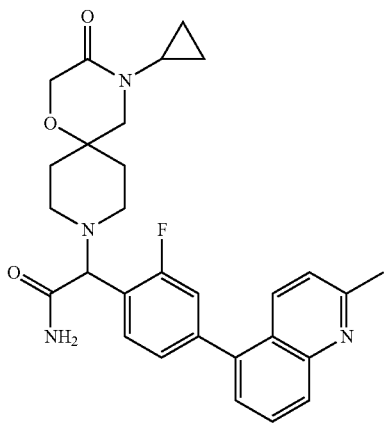 [SMILES: Cc1ccc2c(-c3ccc(C(C(N)=O)N4CCC5(CC4)CN(C4CC4)C(=O)CO5)c(F)c3)cccc2n1]

a) A solution of 2-(4-bromo-2-fluorophenyl)-2-(4-cyclopropyl-3-oxo-1-oxa-4,9-diazaspiro[5.5]undecan-9-yl)acetamide (0.341 mmol) in dry 1,4-dioxane (1.5 mL) was treated with bis(pinacolato)diboron (0.409 mmol), potassium acetate (0.499 mmol) and PdCl$_2$(dppf)-CH$_2$Cl$_2$ adduct (0.017 mmol). The solution was degassed with a stream of nitrogen for 3 min, at which point the reaction vessel was purged with nitrogen and sealed, and the mixture stirred in an oil bath at 90° C. overnight. The reaction mixture was cooled to room temperature and treated with 5-chloro-2-methylquinoline (0.341 mmol), PdCl$_2$(dppf)-CH$_2$Cl$_2$ adduct (0.017 mmol), and 2M aq potassium carbonate (1.022 mmol). The reaction vessel was purged with nitrogen and sealed, and the mixture irradiated in a Biotage Initiator Microwave at 120° C. for 15 min. The reaction was cooled to room temperature, at which point another portion of PdCl$_2$(dppf)-CH$_2$Cl$_2$ adduct (0.017 mmol) was added. The reaction vessel was purged with nitrogen and sealed, and the mixture irradiated in a Biotage Initiator Microwave at 150° C. for 1 h. The reaction was cooled to room temperature and treated with an alternate catalyst, Pd-XPhos Precatalyst (Strem 46-0268) (0.012 mmol). The reaction vessel was purged with nitrogen and sealed, and the mixture irradiated in a Biotage Initiator Microwave at 120° C. for 30 min. The resulting black mixture was diluted with water (50 mL) and was extracted with dichloromethane four times. The combined organic layers were treated with Silicycle Si-thiol (20 mg), dried over sodium sulfate, filtered and concentrated in vacuo. Purification of the residue by reverse phase HPLC (20-65% acetonitrile/water with 0.1% NH$_4$OH) followed by chiral HPLC (Chromegachiral CC$_4$, methanol) and lyophilization from water (w/25% acetonitrile) afforded the title compound as a white solid (22 mg, 12%). MS(ES)+ m/e 503.1 [M+H]$^+$, >99% ee, $\alpha_D$=+25 deg (c=0.03, methanol).

Example 45

(−)-2-(4-cyclopropyl-3-oxo-1-oxa-4,9-diazaspiro [5.5]undecan-9-yl)-2-(2-fluoro-4-(2-methylquinolin-5-yl)phenyl)acetamide a) From Example 44a, the title product was isolated as a solid in >99% ee using chiral HPLC (Chiralpak Chromegachiral CC$_4$, methanol) followed by lyophilization from water (w/25% acetonitrile) (22 mg, 12% yield). MS(ES)+ m/e 503.1 [M+H]$^+$. $\alpha_D$=−26 deg (c=0.03, methanol).

Example 46

(+)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate

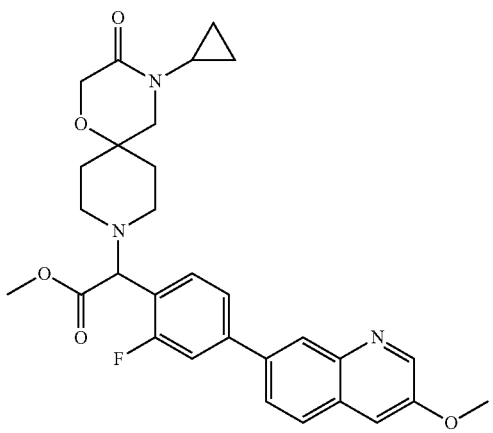

a) 7-Bromo-3-methoxyquinoline

Following the procedure in Example 62a using 1,1,2-trimethoxyethane provided the title compound (61%). $^1$H NMR (400 MHz, DMSO-d$_6$) δ ppm 3.94 (s, 3 H) 7.72 (dd, J=8.84, 2.02 Hz, 1 H) 7.83 (d, J=3.03 Hz, 1 H) 7.89 (d, J=8.84 Hz, 1 H) 8.17 (d, =1.77 Hz, 1 H) 8.68 (d, J=3.03 Hz, 1 H).

b) (+)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate A solution of methyl 2-(4-bromo-2-fluorophenyl)-2-(4-cyclopropyl-3-oxo-1-oxa-4,9-diazaspiro[5.5]undecan-9-yl)acetate (0.626 mmol) in 1,4-dioxane (2.5 mL) was treated with 4,4,4',4',5,5,5',5'-octamethyl-2,2'-bi(1,3,2-dioxaborolane) (0.751 mmol), potassium acetate (0.939 mmol), and PdCl$_2$(dppf)-CH$_2$Cl$_2$ adduct (0.031 mmol). The reaction vessel was purged with nitrogen and sealed, and the mixture stirred in an oil bath at 80° C. overnight. The reaction mixture was cooled to room temperature and was treated with 7-bromo-3-methoxyquinoline (0.626 mmol), PdCl$_2$(dppf)-CH$_2$Cl$_2$ adduct (0.031 mmol), and 2M aq potassium carbonate (1.878 mmol). The solution was degassed with a stream of nitrogen for 3 min, at which point the reaction vessel was purged with nitrogen and sealed, and the mixture irradiated in a Biotage Initiator Microwave at 120° C. for 15 min. The resulting black mixture was diluted with water (100 mL) and was extracted three times with chloroform. The combined organic layers were treated with Silicycle Si-thiol (50 mg), dried over sodium sulfate, filtered and concentrated in vacuo. Purification of the residue by reverse phase HPLC (20-65% acetonitrile/water with 0.1% NH$_4$OH) followed by chiral HPLC (Chiralpak IA column, methanol:acetonitrile-1:1) and lyophilization from water (w/25% acetonitrile) afforded the title compound as a white solid (94 mg, 26%). MS(ES)+ m/e 534.2 [M+H]$^+$, >99% ee, $\alpha_D$=+58 deg (c=0.05, methanol:acetonitrile 1:1).

Example 47

(−)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate a) From Example 46b, the title product was isolated as a solid in >99% ee using chiral HPLC (Chiralpak IA column, methanol:acetonitrile 1:1) followed by lyophilization from water (w/25% acetonitrile) (84 mg, 23% yield). MS(ES)+ m/e 534.2 [M+H]$^+$. $\alpha_D$=−62 deg (c=0.03, methanol:acetonitrile 1:1).

Example 48

(+)-2-(4-cyclopropyl-3-oxo-1-oxa-4,9-diazaspiro[5.5]undecan-9-yl)-2-(2-fluoro-4-(2-hydroxyquinolin-7-yl)phenyl)acetamide a) A solution of 2-(4-bromo-2-fluorophenyl)-2-(4-cyclopropyl-3-oxo-1-oxa-4,9-diazaspiro[5.5]undecan-9-yl)acetamide (0.302 mmol) in 1,4-dioxane (1.5 mL) was treated with 4,4,4',4',5,5,5',5'-octamethyl-2,2'-bi(1,3,2-dioxaborolane) (0.362 mmol), potassium acetate (0.453 mmol), and PdCl$_2$(dppf)-CH$_2$Cl$_2$ adduct (0.030 mmol). The solution was degassed with a stream of nitrogen for 3 min, at which point the reaction vessel was purged with nitrogen and sealed, and the mixture stirred in an oil bath at 90° C. overnight. The reaction mixture was cooled to room temperature and was treated with 7-chloroquinolin-2-ol (0.302 mmol), 2M aq potassium carbonate (0.906 mmol), and Pd-XPhos Precatalyst (Strem 46-0268) (0.030 mmol). The reaction vessel was purged with nitrogen and sealed, and the mixture stirred in an bath at 90° C. for 16 h. The resulting black mixture was diluted with water (50 mL) and brine (20 mL) and was extracted three times with chloroform. The combined organic layers were dried over sodium sulfate, filtered and concentrated in vacuo. The resulting crude material was purified by reverse phase HPLC (10-40% acetonitrile with 0.1% TFA/water with 0.1% TFA). Fractions containing the desired product were combined and the pH of the resulting mixture was adjusted to ~7 with saturated aq sodium bicarbonate. This mixture was concentrated to a minimal volume in vacuo and was then extracted three times with chloroform. The combined organic layers were dried over sodium sulfate, filtered and concentrated in vacuo. Purification of the residue by chiral HPLC (Chiralpak AS-H column, acetonitrile:methanol 9:1) followed by lyophilization from water (w/25% acetonitrile) afforded the title compound as a white solid (20 mg, 12%). MS(ES)+ m/e 505.2 [M+H]$^+$, >99% ee, $\alpha_D$=+43 deg (c=0.02, acetonitrile:methano19:1).

Example 49

(−)-2-(4-cyclopropyl-3-oxo-1-oxa-4,9-diazaspiro[5.5]undecan-9-yl)-2-(2-fluoro-4-(2-hydroxyquinolin-7-yl)phenyl)acetamide a) From Example 48a, the title product was isolated as a solid in >99% ee using chiral HPLC (Chiralpak AS-H column, acetonitrile:methanol 9:1) followed by lyophilization from water (w/25% acetonitrile) (21 mg, 13% yield). MS(ES)+ m/e 505.3 [M+H]$^+$. $\alpha_D$=−37 deg (c=0.01, acetonitrile:methanol 9:1).

Example 50

(+)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide

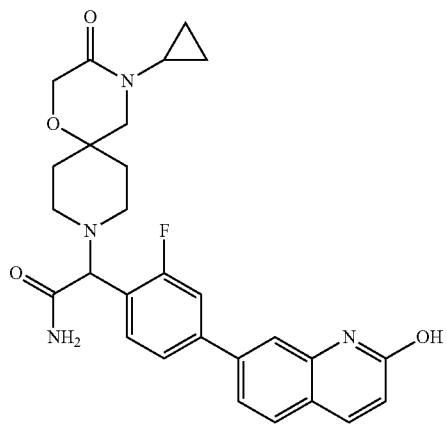 [SMILES: NC(=O)C(c1ccc(-c2ccc3ccc(O)nc3c2)cc1F)N1CCC2(CC1)CN(C1CC1)C(=O)CO2]

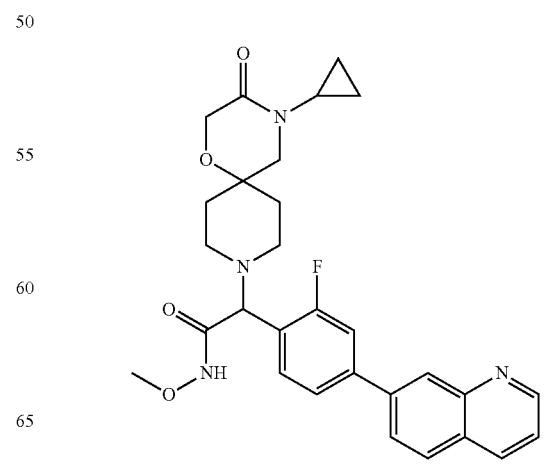

a) 2-(4-bromo-2-fluorophenyl)-2-(4-cyclopropyl-3-oxo-1-oxa-4,9-diazaspiro[5.5]undecan-9-yl)-N-methoxyacetamide A solution of 2-(4-bromo-2-fluorophenyl)-2-(4-cyclopropyl-3-oxo-1-oxa-4,9-diazaspiro[5.5]undecan-9-yl)acetic acid (0.453 mmol) in dichloromethane (1 mL) was treated with N-(3-dimethylaminopropyl)-N'-ethylcarbodiimide hydrochloride (0.680 mmol) and 4-(dimethylamino)pyridine (2.266 mmol) at room temperature. This mixture was stirred for 10 min at which point O-methylhydroxylamine hydrochloride (0.906 mmol) was added. The reaction vessel was sealed and the mixture was stirred at room temperature for 18 h and at 45° C. for 24 h. The reaction was then cooled to room temperature and was treated with pyridine (0.5 mL). The reaction vessel was resealed and stirred overnight in an oil bath at 45° C. At this point the reaction was cooled to room temperature and treated with additional portions of N-(3-dimethylaminopropyl)-N'-ethylcarbodiimide hydrochloride (0.680 mmol) and O-methylhydroxylamine hydrochloride (0.906 mmol). The reaction vessel was resealed and stirred in an oil bath at 45° C. for 2 h. The reaction mixture was then concentrated to dryness in vacuo. The resulting orange residue was dissolved in dichloromethane (10 mL) and was concentrated in vacuo. Purification of the residue by reverse phase HPLC (10-40% acetonitrile/water with 0.1% $NH_4OH$) afforded the title compound as a clear oily solid (89 mg, 38% yield). MS(ES)+ m/e 470.1/472.1 $[M+H]^+$ (bromide isotope pattern).

b) (+)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide A solution of 2-(4-bromo-2-fluorophenyl)-2-(4-cyclopropyl-3-oxo-1-oxa-4,9-diazaspiro[5.5]undecan-9-yl)-N-methoxyacetamide (0.170 mmol) in dry 1,4-dioxane (1 mL) was treated with 7-(4,4,5,5-tetramethyl-1,3,2-dioxaborolan-2-yl)quinoline (0.187 mmol), $PdCl_2$(dppf)-$CH_2Cl_2$ adduct (8.52 µmol) and 2M aq potassium carbonate (0.511 mmol). The reaction vessel was purged with nitrogen and sealed, and the mixture irradiated in a Biotage Initiator Microwave at 120° C. for 15 min. The resulting black mixture was diluted with water (50 mL) and brine (20 mL) and was extracted four times with chloroform. The combined organic layers were dried over sodium sulfate, filtered and concentrated in vacuo. Purification of the residue by reverse phase HPLC (20-50% acetonitrile/water with 0.1%

$NH_4OH$) followed by chiral HPLC (Chromegachiral $CC_4$, methanol) and lyophilization from water (w/25% acetonitrile) afforded the title compound as a white solid (11 mg, 11%). MS(ES)+ m/e 519.3 $[M+H]^+$, >99% ee, $\alpha_D$=+11 deg (c=0.03, methanol).

Example 51

(−)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide a) From Example 50b, the title product was isolated as a white solid in >99% ee using chiral HPLC (Chiralpak Chromegachiral $CC_4$, methanol) followed by lyophilization from water (w/25% acetonitrile) (10 mg, 10% yield). MS(ES)+ m/e 519.3 $[M+H]^+$. $\alpha_D$=−10 deg (c=0.03, methanol).

Example 52

(+)-2-(4-ethyl-3-oxo-1-oxa-4,9-diazaspiro[5.5]undecan-9-yl)-2-(2-fluoro-4-(8-fluoroquinolin-7-yl)phenyl)acetamide

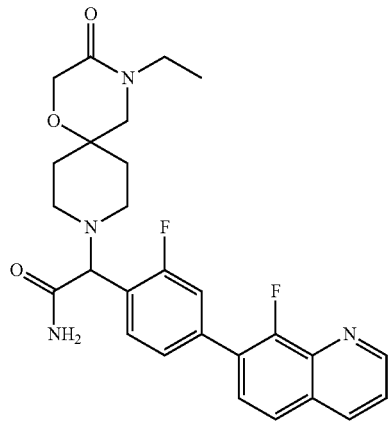 [SMILES: CCN1CC2(CCN(C(C(N)=O)c3ccc(-c4ccc5cccnc5c4F)cc3F)CC2)OCC1=O]

a) 7-bromo-8-fluoroquinoline

A 500 mL round bottom flask equipped with a stirbar and air-condenser was charged with 3-bromo-2-fluoroaniline (10.00 g, 52.6 mmol), sodium 3-nitrobenzenesulfonate (21.13 g, 94 mmol), and propane-1,2,3-triol (glycerol) (13.57 g, 147 mmol). The mixture was taken up in water (11.38 mL), carefully treated with conc. sulfuric acid (21.06 mL), and then heated to 150° C. with stirring for 2 h. The reaction was then cooled to room temperature and the flask fitted with an ice bath. The reaction mixture was carefully neutralized with 5N aq sodium hydroxide (~180 mL). The mixture was then allowed to stir for 20 min, checked for neutral pH, and then diluted with dichloromethane (1000 mL). The entire mixture was transferred to a separatory funnel and the resulting emulsion was treated with ~200 mL saturated brine and allowed to stand overnight to separate the layers. The organic layer was isolated and the aqueous layer was extracted with an additional quantity of dichloromethane (~400 mL). The organics were then pooled, washed with 400 mL 1N aq sodium hydroxide solution, dried over sodium sulfate, filtered, and concentrated to a residue. The residue solidified under high vacuum to afford the title compound as a dark brown solid (9.16 g, 75% yield). MS(ES)+ m/e 225.9, 227.8 $[M+H]^+$.

b) (+)-2-(4-ethyl-3-oxo-1-oxa-4,9-diazaspiro[5.5]undecan-9-yl)-2-(2-fluoro-4-(8-fluoroquinolin-7-yl)phenyl)acetamide A 20 mL reaction vial equipped with a stirbar was charged with 2-(4-bromo-2-fluorophenyl)-2-(4-ethyl-3-oxo-1-oxa-4,9-diazaspiro[5.5]undecan-9-yl)acetamide (0.150 g, 0.350 mmol), bis(pinacolato)diboron (0.205 g, 0.806 mmol), $PdCl_2$(dppf)-$CH_2Cl_2$ adduct (0.020 g, 0.025 mmol), and potassium acetate (0.076 g, 0.770 mmol). The solids were diluted with 1,4-dioxane (3.12 mL) and the reaction mixture was warmed to 90° C. with stirring overnight. The reaction mixture was then treated with PdCl$_2$(dppf)-CH$_2$Cl$_2$ adduct (0.020 g, 0.025 mmol), 2M aq potassium carbonate (0.385 mL, 0.770 mmol), and 7-bromo-8-fluoroquinoline (0.091 g, 0.403 mmol), and the resulting reaction mixture was stirred at 90° C. for 1 h. The mixture was then diluted with 20 mL dichloromethane and filtered through a stacked pad of sodium sulfate over celite. The filtrate was concentrated to a residue, which was purified by silica gel flash chromatography (0.5-10% methanol:ethyl acetate). Fractions containing the desired material were pooled and concentrated to a hard lacquer and the product was resolved by chiral preparative HPLC (Chromegachiral CC4, 100% methanol) to afford the title compound in >99% ee as an off white solid (42 mg, 0.081 mmol, 23% yield). MS(ES)$^+$ m/e 495.4 [M+H]$^+$. $\alpha_D$=+40 deg (c=0.06, methanol).

Example 53

(−)-2-(4-ethyl-3-oxo-1-oxa-4,9-diazaspiro[5.5]undecan-9-yl)-2-(2-fluoro-4-(8-fluoroquinolin-7-yl)phenyl)acetamide a) From Example 52b, the title product was isolated in >99% ee using chiral HPLC (Chromegachiral CC4, methanol) (42 mg, 0.081 mmol, 23% yield). MS(ES)$^+$ m/e 495.3 [M+H]$^+$. $\alpha_D$=−39 deg (c=0.06, methanol).

Example 54

(+)-2-(4-ethyl-3-oxo-1-oxa-4,9-diazaspiro[5.5]undecan-9-yl)-2-(2-fluoro-4-(8-methoxyquinolin-7-yl)phenyl)acetamide

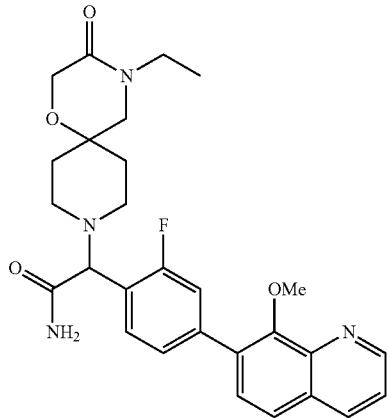 [SMILES: CCN1CC2(CCN(C(C(N)=O)c3ccc(-c4ccc5cccnc5c4OC)cc3F)CC2)OCC1=O]

a) 7-bromo-8-methoxyquinoline

In an oven dried round bottom flask under nitrogen, a solution of 7-bromoquinolin-8-ol (1 g, 4.46 mmol) in N,N-dimethylformamide (20 mL) at room temperature was treated with sodium hydride (60% dispersion in mineral oil, 0.268 g, 6.69 mmol) to give a bright yellow mixture and was stirred for 3 min. Iodomethane (0.307 mL, 4.91 mmol) was then added by syringe and the reaction was stirred for 30 min. The reaction was quenched carefully with water (50 mL) and diluted with ethyl acetate (100 mL). The layers were separated and the organic layer was dried over magnesium sulfate and concentrated in vacuo to give a liquid, which solidified to a white solid (1.06 g, quantitative yield) on standing overnight. MS(ES)+ m/e 237.8, 239.7 [M+H]$^+$.

b) Following the procedure described in Example 52b with 7-bromo-8-methoxyquinoline afforded the title product (26% yield) in >99% ee after chiral HPLC (Chromegachiral CC4, methanol). MS(ES)$^+$ m/e 507.3 [M+H]$^+$. $\alpha_D$=+49 deg (c=0.08, methanol).

Example 55

(−)-2-(4-ethyl-3-oxo-1-oxa-4,9-diazaspiro[5.5]undecan-9-yl)-2-(2-fluoro-4-(8-methoxyquinolin-7-yl)phenyl)acetamide a) From Example 56b, the title product was isolated in >99% ee using chiral HPLC (Chromegachiral CC4, methanol) (28% yield). MS(ES)$^+$ m/e 507.3 [M+H]$^+$. $\alpha_D$=−42 deg (c=0.08, methanol).

Example 56

2-(4-cyclopropyl-3-oxo-1-oxa-4,9-diazaspiro[5.5]undecan-9-yl)-2-(2,6-difluoro-4-(quinolin-7-yl)phenyl)acetamide

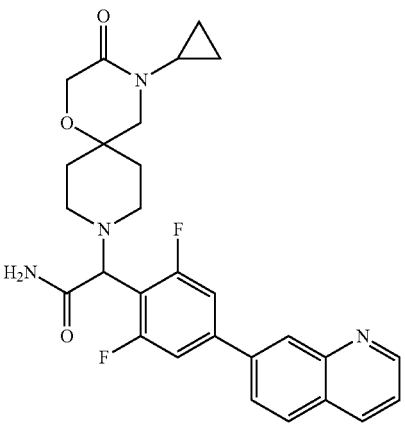

a) 2-(4-bromo-2,6-difluorophenyl)acetonitrile

To a mixture of potassium cyanide (0.55 g, 8.4 mmol) in dimethyl sulfoxide (10 mL) at 23° C. was slowly added 5-bromo-2-(bromomethyl)-1,3-difluorobenzene (2 g, 7.0 mmol), and the reaction mixture was stirred for 3 h. The reaction mixture was poured into saturated aqueous sodium chloride (100 mL) and was extracted with ether (3×100 mL). The combined organic layers were washed with saturated aq sodium chloride (3×50 mL), dried over anhydrous sodium sulfate, and concentrated to dryness. Purification of the residue by flash chromatography (0-100% ethyl acetate/hexanes) afforded the title product (0.84 g, 52%). $^1$H NMR (400 MHz, DMSO-d$_6$) δ ppm 4.04 (s, 2 H) 7.60-7.62 (m, 1 H) 7.62-7.65 (m, 1 H).

b) 2-(4-bromo-2,6-difluorophenyl)acetamide

To a solution of sulfuric acid (0.96 mL, 18.1 mmol) in acetic acid (20 mL) was slowly added 2-(4-bromo-2,6-difluorophenyl)acetonitrile (0.84 g, 3.6 mmol) portion-wise while stirring, and the reaction mixture was then stirred for 1 h at 100° C. After cooling to 5° C., the mixture was carefully adjusted to pH 9 with 28-30% aq ammonium hydroxide and then was extracted with chloroform (3×40 mL). The combined organic layers were dried over anhydrous sodium sulfate and concentrated in vacuo. Purification of the residue by flash chromatography (0-100% ethyl acetate/hexanes) provided the title product (0.71 g, 78%). MS(ES$^+$) m/e 250 [M+H]$^+$; $^1$H NMR (400 MHz, CD$_2$Cl$_2$) δ ppm 3.60 (s, 2 H) 5.54 (br. s., 2 H) 7.10-7.21 (m, 2 H).

c) 2-bromo-2-(4-bromo-2,6-difluorophenyl)acetamide

A solution of 2-(4-bromo-2,6-difluorophenyl)acetamide (0.4 g, 1.6 mmol) in carbon tetrachloride (5 mL) was degassed with nitrogen for 5 min. To this was added N-bromosuccinimide (0.28 g, 1.6 mmol) and then azobisisobutyronitrile (0.039 g, 0.24 mmol) while stirring. The reaction mixture was stirred at 80° C. overnight and then cooled to room temperature. The reaction mixture was concentrated to dryness in vacuo, and the residue was purified by flash chromatography (0-100% ethyl acetate/hexanes) to afford the title product (60 mg, 11%). MS(ES)$^+$ m/e 328 [M+H]$^+$.

d) 2-(4-cyclopropyl-3-oxo-1-oxa-4,9-diazaspiro[5.5] undecan-9-yl)-2-(2,6-difluoro-4-(quinolin-7-yl)phenyl)acetamide A solution of 4-cyclopropyl-1-oxa-4,9-diazaspiro[5.5]undecan-3-one hydrochloride (45.0 mg, 0.18 mmol) in N,N-dimethylformamide (0.5 mL) was treated with 2M aq potassium carbonate (0.1 mL, 0.2 mmol), followed by the 2-bromo-2-(4-bromo-2,6-difluorophenyl)acetamide (60 mg, 0.18 mmol). The reaction mixture was stirred at 40° C. for overnight, at which point it had proceeded to completion. The reaction mixture was poured into water (20 mL) and extracted with ethyl acetate (20 mL×3). The combined organic layers were dried and concentrated to dryness to afford the crude intermediate. To a solution of this crude intermediate, 7-(4,4,5,5-tetramethyl-1,3,2-dioxaborolan-2-yl)quinoline (23.3 mg, 0.09 mmol), and 2M aq potassium carbonate (0.1 mL, 0.2 mmol) in 1,4-dioxane (2.5 mL) was added PdCl$_2$(dppf)-CH$_2$Cl$_2$ adduct (6 mg, 7.3 μmol). The reaction mixture was purged with nitrogen, sealed, and irradiated in the microwave at 110° C. for 25 min, at which point the reaction had proceeded to completion. The reaction mixture was diluted with ethyl acetate (25 mL) and washed with 5 mL of 1M aq HCl. The organic phase was then washed with brine (5 mL), dried over anhydrous sodium sulfate, filtered through a pad of celite, and concentrated in vacuo. The crude product was purified by reverse phase HPLC (5-45% acetonitrile+0.1% TFA:water+0.1% TFA). The appropriate fractions were collected and evaporated to yield the title compound as a trifluoroacetate salt (11 mg, 9%). MS(ES)$^+$ m/e 507 [M+H]$^+$; $^1$H NMR (400 MHz, CD$_2$Cl$_2$) δ ppm 0.61-0.71 (m, 2 H) 0.78-0.89 (m, 2 H) 1.98-2.06 (m, 4 H) 2.69-2.79 (m, 2 H) 2.90 (br. s., 1 H) 3.21 (s, 3 H) 3.38 (br. s., 2 H) 4.01 (s, 2 H) 5.96 (br. s., 1 H) 7.16 (br. s., 1 H) 7.54 (d, J=9.35 Hz, 2 H) 7.91 (dd, J=8.34, 5.05 Hz, 1 H) 8.09 (dd, J=8.72, 1.64 Hz, 1 H) 8.26 (d, J=8.59 Hz, 1 H) 8.76-8.85 (m, 2 H) 9.28 (dd, J=5.18, 1.64 Hz, 1 H).

Example 57 ethyl 2-(4-ethyl-3-oxo-1-oxa-4,9-diazaspiro[5.5] undecan-9-yl)-2-(2-fluoro-4-(quinolin-7-yl)phenyl)acetate

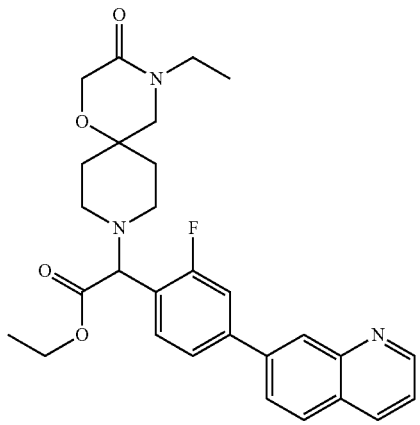 [SMILES: CCOC(=O)C(c1ccc(-c2ccc3cccnc3c2)cc1F)N1CCC2(CC1)CN(CC)C(=O)CO2]

a) Ethyl 2-bromo-2-(4-bromo-2-fluorophenyl)acetate

To a stirring solution of ethyl 2-(4-bromo-2-fluorophenyl)acetate (3.92 g, 15.0 mmol) in carbon tetrachloride (50 mL) was slowly added N-bromosuccinimide (2.67 g, 15.0 mmol) and then azobisisobutyronitrile (0.37 g, 2.3 mmol). The reaction mixture was stirred for 9 h at 90° C. and then cooled to room temperature. The residue was purified by flash chromatography (0-100% ethyl acetate/hexanes) to provide the title product (4.9 g, 96% yield). MS(ES)$^+$ m/e 340.9 [M+H]$^+$.

b) ethyl 2-(4-ethyl-3-oxo-1-oxa-4,9-diazaspiro[5.5] undecan-9-yl)-2-(2-fluoro-4-(quinolin-7-yl)phenyl)acetate To a solution of tert-butyl 4-ethyl-3-oxo-1-oxa-4,9-diazaspiro[5.5]undecane-9-carboxylate (1 g, 3.35 mmol) in dichloromethane (10 mL) was added TFA (0.775 mL, 10.05 mmol). The reaction mixture was stirred at room temperature overnight, at which point the deprotection had proceeded to completion. The reaction mixture was concentrated in vacuo, dichloromethane was added, and the solution was concentrated in vacuo again. The residue was dissolved with N,N-dimethylformamide (12 mL). To this solution was added potassium carbonate (0.463 g, 3.35 mmol) and ethyl 2-bromo-2-(4-bromophenyl)acetate (1.079 g, 3.35 mmol). The reaction mixture was stirred at 40° C. for overnight, at which point the reaction had proceeded to completion. The reaction mixture was poured into water (120 mL) and was extracted with ethyl acetate (80 mL×3). The combined organic layers were dried and concentrated in vacuo. Crude ethyl 2-(4-bromo-2-fluorophenyl)-2-(4-ethyl-3-oxo-1-oxa-4,9-diazaspiro[5.5]undecan-9-yl)acetate was obtained (590 mg) and was used directly in the next step. MS(ES)$^+$ m/e 457 [M+H]$^+$.

To a solution of the crude ethyl 2-(4-bromo-2-fluorophenyl)-2-(4-ethyl-3-oxo-1-oxa-4,9-diazaspiro[5.5]undecan-9-yl)acetate (590 mg), 7-(4,4,5,5-tetramethyl-1,3,2-dioxaborolan-2-yl)quinoline (329 mg, 1.29 mmol) and 2M aq K$_2$CO$_3$ (1.4 mL, 2.8 mmol) in 1,4-dioxane (2.5 mL) was added PdCl$_2$(dppf)-CH$_2$Cl$_2$ adduct (53 mg, 0.065 mmol). The reaction mixture was purged with nitrogen, sealed, and irradiated in the microwave at 110° C. for 25 min, at which point the reaction had proceeded to completion. The reaction mixture was diluted with ethyl acetate (25 mL) and washed with 5 mL of 1M aq HCl. The organic phase was washed with brine (5 mL), dried over anhydrous sodium sulfate, filtered through a pad of celite, and concentrated in vacuo. The crude product was purified with reverse phase HPLC (25-55% acetonitrile+ 0.1% TFA:water+0.1% TFA). The appropriate fractions were collected and evaporated to yield the title compound as a trifluoroacetate salt (31 mg, 2% over the two steps). MS(ES)+ m/e 506 [M+H]+; 1H NMR (400 MHz, CD2Cl2) δ ppm 1.14 (t, J=7.20 Hz, 3 H) 1.28 (t, J=7.07 Hz, 3 H) 2.14 (s, 1 H) 2.11 (s, 1 H) 2.28-2.38 (m, 2 H) 3.05 (t, J=11.75 Hz, 1 H) 3.22 (t, J=13.26 Hz, 1 H) 3.30 (s, 2 H) 3.44 (d, J=7.07 Hz, 2 H) 3.62 (d, J=10.11 Hz, 1 H) 3.76 (d, J=13.89 Hz, 1 H) 4.06 (s, 2 H) 4.29-4.41 (m, 2 H) 5.43 (s, 1 H) 7.71-7.82 (m, 3 H) 7.89-7.96 (m, 1 H) 8.13 (d, J=8.59 Hz, 1 H) 8.26 (d, J=8.59 Hz, 1 H) 8.79-8.84 (m, 2 H) 9.27-9.32 (m, 1 H).

Example 58

(+)-2-(4-ethyl-3-oxo-1-oxa-4,9-diazaspiro[5.5]undecan-9-yl)-2-(2-fluoro-4-(quinolin-7-yl)phenyl)acetamide

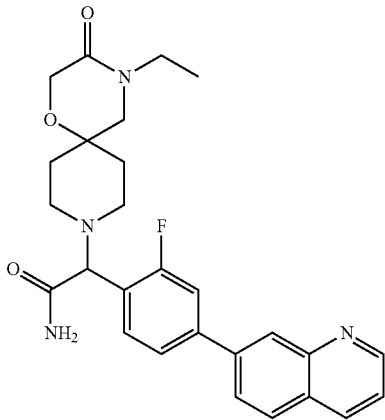 [SMILES: CCN1CC2(CCN(C(C(N)=O)c3ccc(-c4ccc5cccnc5c4)cc3F)CC2)OCC1=O]

a) 2-(4-bromo-2-fluorophenyl)-2-(4-ethyl-3-oxo-1-oxa-4,9-diazaspiro[5.5]undecan-9-yl)acetamide To a mixture of 2-bromo-2-(4-bromo-2-fluorophenyl)acetamide (250 mg, 0.8 mmol) and 4-ethyl-1-oxa-4,9-diazaspiro[5.5]undecan-3-one hydrochloride (189 mg, 0.8 mmol) in N,N-dimethylformamide (2 mL) at 23° C. was added potassium carbonate (333 mg, 2.4 mmol). The reaction mixture was stirred for 3 h and then was poured into brine (100 mL) and extracted with ether (3×100 mL). The combined organic layers were washed with brine (3×50 mL), dried over anhydrous Na2SO4, filtered and concentrated in vacuo. Purification of the residue by flash chromatography (0-100% ethyl acetate/hexanes) afforded the title product (214 mg, 62%). MS(ES)+ m/e 428 [M+H]+; 1H NMR (400 MHz, CD3CN) δ ppm 1.07 (t, J=7.07 Hz, 3 H) 1.65-1.77 (m, 2 H) 1.79-1.91 (m, 2 H) 2.10-2.16 (m, 1 H) 2.44 (br. s., 1 H) 2.54 (s, 1 H) 2.66 (br. s., 1 H) 3.17 (s, 2 H) 3.35 (q, J=7.16 Hz, 2 H) 3.93 (d, J=1.52 Hz, 2 H) 4.39 (s, 1 H) 6.00 (br. s., 1 H) 7.19 (br. s., 1 H) 7.27-7.35 (m, 1 H) 7.39 (t, J=2.27 Hz, 1 H) 7.41 (t, J=2.15 Hz, 1 H).

b) (+)-2-(4-ethyl-3-oxo-1-oxa-4,9-diazaspiro[5.5]undecan-9-yl)-2-(2-fluoro-4-(quinolin-7-yl)phenyl)acetamide To a solution of 2-(4-bromo-2-fluorophenyl)-2-(4-ethyl-3-oxo-1-oxa-4,9-diazaspiro[5.5]undecan-9-yl)acetamide (214 mg, 0.5 mmol), 7-(4,4,5,5-tetramethyl-1,3,2-dioxaborolan-2-yl)quinoline (127 mg, 0.5 mmol) and 2M aq K2CO3 (0.55 mL, 1.1 mmol) in 1,4-dioxane (2.5 mL) was added PdCl2 (dppf)-CH2Cl2 adduct (20.4 mg, 0.025 mmol). The reaction mixture was purged with nitrogen and the vessel was sealed and irradiated in the microwave at 110° C. for 25 min, at which point the reaction had proceeded to completion. The reaction mixture was diluted with ethyl acetate (25 mL) and washed with 5 mL of 1M aq HCl. The organic phase was then washed with brine (5 mL), dried over anhydrous sodium sulfate, filtered through a pad of celite, and concentrated in vacuo. Purification of the residue by reverse phase HPLC (5-65% acetonitrile:water with 0.1% NH4OH) afforded the title product as a racemate, which was resolved by chiral HPLC (Chromegachiral CC4, methanol) to yield the title product in >98% ee (31 mg, 13%). αD=+21 deg (c=0.06, methanol); MS(ES)+ m/e 477 [M+H]+; 1H NMR (400 MHz, CD2Cl2) δ ppm 1.13 (t, J=7.20 Hz, 3 H) 1.65-1.74 (m, 1 H) 1.75-1.80 (m, 1 H) 1.89-2.01 (m, 2 H) 2.31-2.41 (m, 1 H) 2.58-2.70 (m, 2 H) 2.78 (br. s., 1 H) 3.19 (s, 2 H) 3.41 (q, J=7.33 Hz, 2 H) 3.97-4.08 (m, 2 H) 4.54 (s, 1 H) 5.65 (br. s., 1 H) 7.27 (br. s., 1 H) 7.43-7.48 (m, 2 H) 7.55 (d, J=1.77 Hz, 1 H) 7.64 (dd, J=7.96, 1.89 Hz, 1 H) 7.87 (dd, J=8.59, 2.02 Hz, 1 H) 7.98 (d, J=8.59 Hz, 1 H) 8.25 (dd, J=8.34, 1.01 Hz, 1 H) 8.36 (d, J=1.77 Hz, 1 H) 8.97 (dd, J=4.04, 1.77 Hz, 1 H).

Example 59

(−)-2-(4-ethyl-3-oxo-1-oxa-4,9-diazaspiro[5.5]undecan-9-yl)-2-(2-fluoro-4-(quinolin-7-yl)phenyl)acetamide a) From Example 58b, the title product was also isolated in >98% ee using chiral HPLC (Chromegachiral CC4, methanol) followed by concentration in vacuo and lyophilization (36 mg, 15% yield). αD=−22 deg (c=0.04, methanol); MS(ES)+ m/e 477 [M+H]+; 1H NMR (400 MHz, CD2Cl2) δ ppm 1.13 (t, J=7.20 Hz, 3 H) 1.68-1.80 (m, 2 H) 1.90-2.02 (m, 2 H) 2.31-2.40 (m, 1 H) 2.65 (t, J=12.63 Hz, 2 H) 2.80 (t, J=12.13 Hz, 1 H) 3.19 (s, 2 H) 3.41 (d, J=7.07 Hz, 2 H) 4.02 (d, J=1.77 Hz, 2 H) 4.54 (s, 1 H) 5.63 (br. s., 1 H) 7.27 (br. s., 1 H) 7.43-7.53 (m, 2 H) 7.55 (d, J=1.77 Hz, 1 H) 7.64 (dd, J=7.96, 1.89 Hz, 1 H) 7.87 (dd, J=8.46, 1.89 Hz, 1 H) 7.98 (d, J=8.34 Hz, 1 H) 8.26 (d, J=8.34 Hz, 1 H) 8.36 (s, 1 H) 8.97 (dd, J=4.29, 1.77 Hz, 1 H).

Example 60

(+)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide

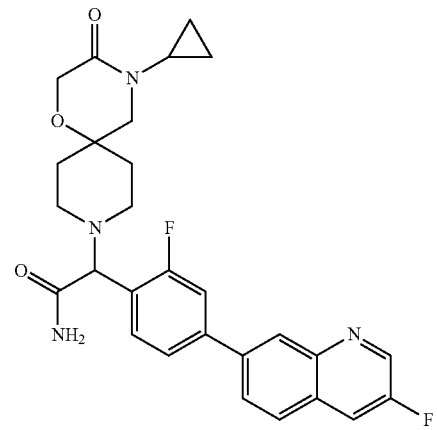 [SMILES: NC(=O)C(c1ccc(-c2ccc3cc(F)cnc3c2)cc1F)N1CCC2(CC1)CN(C1CC1)C(=O)CO2]

a) 2-(7-bromoquinolin-3-yl)isoindoline-1,3-dione

A mixture of 2-(2,2-diethoxyethyl)isoindoline-1,3-dione (3.16 g, 12.00 mmol), 2-amino-4-bromobenzaldehyde (2 g, 10.00 mmol) and p-toluenesulfonic acid monohydrate (1.902 g, 10.00 mmol) in toluene (60 mL) was heated under reflux using Dean-Stark apparatus overnight. A very dark/black solid precipitated overnight and was collected, washed with toluene and hexanes, then dissolved in chloroform fortified with DMF. The mixture was washed with aq. NaHCO$_3$ solution (×2), ensuring any precipitate was dissolved in additional chloroform during separation. The organic layer was dried (sodium sulfate) and evaporated onto silica gel. Purification by flash chromatography (0-2% methanol in dichloromethane) afforded the title compound (1.6 g, 45%). $^1$H NMR (400 MHz, DMSO-d$_6$) δ ppm 9.05 (d, 1 H), 8.57 (d, J=2.3 Hz, 1 H), 8.35 (d, J=1.8 Hz, 1 H), 8.11 (d, J=8.6 Hz, 1 H), 8.09-8.02 (m, 2 H), 8.02-7.93 (m, 2 H), 7.87 (dd, J=1.9, 8.7 Hz, 1 H).

b) 7-bromoquinolin-3-amine

A suspension of 2-(7-bromoquinolin-3-yl)isoindoline-1,3-dione (10 g, 28.3 mmol) in ethanol (200 mL) was treated with hydrazine (1.777 mL, 56.6 mmol) then heated under reflux for 1 h. The mixture was allowed to cool, the precipitate was collected and washed with a little ethanol, and the filtrate was evaporated to a grey solid. The isolated solid was dissolved in warm ethanol and adsorbed onto silica gel. Purification of the solid by silica gel chromatography (50-100% ethyl acetate/hexanes) afforded the title compound (3.5 g, 56%). $^1$H NMR (400 MHz, DMSO-d$_6$) δ ppm 5.83 (s, 2 H) 7.14 (d, J=2.53 Hz, 1 H) 7.49 (dd, J=8.84, 2.02 Hz, 1 H) 7.54-7.65 (m, 1 H) 7.94 (d, J=1.77 Hz, 1 H) 8.46 (d, J=2.78 Hz, 1 H).

c) 7-bromo-3-fluoroquinoline

A solution of 7-bromoquinolin-3-amine (1.0 g, 4.48 mmol) in chlorobenzene (10 mL) was added dropwise over 10 min onto boron trifluoride dihydrate (0.429 mL, 6.72 mmol). The mixture was heated to 50° C. and t-butyl nitrite (0.773 mL, 4.48 mmol) was added at this temperature over 20 min. The temperature was then raised to 100° C. and the mixture was stirred for 30 min. The reaction mixture was cooled and poured onto ice/aqueous sodium bicarbonate solution. The resulting solid was suspended in ethanol, diluted with additional aqueous sodium bicarbonate solution, and extracted with chloroform (×3). The combined extracts were washed with dilute brine, dried (sodium sulfate) and evaporated under reduced pressure. Purification of the residue by silica gel chromatography (100% dichloromethane) afforded the title compound (350 mg, 35%). $^1$H NMR (400 MHz, DMSO-d6) δ ppm 7.84 (dd, J=8.72, 1.39 Hz, 1 H) 8.00 (d, J=8.84 Hz, 1 H) 8.31 (d, J=2.02 Hz, 1 H) 8.34 (dd, J=9.47, 2.91 Hz, H) 9.00 (d, 1 H).

d) (+)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide To a solution of 2-(4-bromo-2-fluorophenyl)-2-(4-cyclopropyl-3-oxo-1-oxa-4,9-diazaspiro[5.5]undecan-9-yl)acetamide (110 mg, 0.25 mmol), 4,4,4',4',5,5,5',5'-octamethyl-2,2'-bi(1,3,2-dioxaborolane) (63 mg, 0.25 mmol), and potassium acetate (49 mg, 0.5 mmol) in 1,4-dioxane (2.5 mL) was added PdCl$_2$(dppf)-CH$_2$Cl$_2$ adduct (20.4 mg, 0.025 mmol). The reaction mixture was purged with nitrogen and then was heated at 120° C. for 4 h. The reaction mixture was cooled and 7-bromo-3-fluoroquinoline (56.5 mg, 0.25 mmol) and 2M aq K$_2$CO$_3$ (0.27 mL, 0.55 mmol) were added. The reaction mixture was purged with nitrogen and was heated with stirring at 100° C. for one hour. The reaction mixture was diluted with dichloromethane (60 mL), and salts were filtered away. The organic mixture was filtered through a plug of celite and sodium sulfate. The filtrate was treated with a small amount of Silicycle Si-thiol resin for 30 min and was then filtered and concentrated in vacuo. Purification of the residue by reverse phase HPLC (10-70% acetonitrile:water with 0.1% NH$_4$OH) followed by chiral HPLC (Chromegachiral CC4, methanol) afforded the title product in >98% ee (34 mg, 27%). α$_D$=+37 deg (c=0.04, methanol); MS(ES)$^+$ m/e 507 [M+H]$^+$; $^1$H NMR (400 MHz, CD$_2$Cl$_2$) δ ppm 0.60-0.69 (m, 2 H) 0.77-0.86 (m, 2 H) 1.64-1.77 (m, 2 H) 1.85-1.97 (m, 2 H) 2.26-2.38 (m, 1 H) 2.57 (d, J=14.40 Hz, 1 H) 2.66-2.76 (m, 2 H) 2.79 (d, J=10.86 Hz, 1 H) 3.15 (s, 2 H) 4.00 (d, J=1.77 Hz, 2 H) 4.53 (s, 1 H) 5.63 (br. s., 1 H) 7.26 (d, J=3.79 Hz, 1 H) 7.46 (t, J=7.71 Hz, 1 H) 7.56 (d, J=1.77 Hz, 1 H) 7.62 (dd, J=7.96, 1.89 Hz, 1 H) 7.84-7.93 (m, 2 H) 7.93-8.00 (m, 1 H) 8.38 (s, 1 H) 8.88 (d, J=2.78 Hz, 1 H).

Example 61

(−)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide a) From Example 60d, the title product was also isolated in >98% ee from chiral HPLC (Chromegachiral CC4, methanol) followed by concentration in vacuo and lyophilization (33 mg, 26% yield). α$_D$=−38 deg (c=0.03, methanol); MS(ES)$^+$ m/e 507 [M+H]$^+$; $^1$H NMR (400 MHz, CD$_2$Cl$_2$) δ ppm 0.61-0.66 (m, 2 H) 0.79-0.85 (m, 2 H) 1.64-1.77 (m, 2 H) 1.86-1.97 (m, 2 H) 2.28-2.36 (m, 1 H) 2.57-2.61 (m, 1 H) 2.62-2.74 (m, 2 H) 2.79 (d, J=11.12 Hz, 1 H) 3.15 (s, 2 H) 4.00 (d, J=1.77 Hz, 2 H) 4.53 (s, 1 H) 5.61 (br. s., 1 H) 7.26 (d, J=4.29 Hz, 1 H) 7.46 (t, J=7.71 Hz, 1 H) 7.54 (d, J=1.77 Hz, 1 H) 7.62 (dd, J=8.08, 1.77 Hz, 1 H) 7.87 (d, J=2.27 Hz, 2 H) 7.95-8.00 (m, 1 H) 8.30-8.42 (m, 1 H) 8.88 (d, J=2.78 Hz, 1 H).

Example 62

2-(4-(3-cyanoquinolin-7-yl)-2-fluorophenyl)-2-(4-cyclopropyl-3-oxo-1-oxa-4,9-diazaspiro[5.5]undecan-9-yl)acetamide

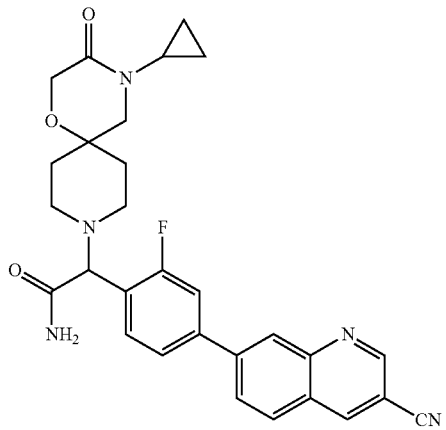 [SMILES: N#Cc1cnc2cc(-c3ccc(C(C(N)=O)N4CCC5(CC4)CN(C4CC4)C(=O)CO5)c(F)c3)ccc2c1]

a) 7-bromoquinoline-3-carbonitrile

A mixture of 3,3-diethoxypropanenitrile (1.80 mL, 12.00 mmol), 2-amino-4-bromobenzaldehyde (2 g, 10.00 mmol) and p-toluenesulfonic acid monohydrate (0.380 g, 2.000 mmol) in toluene (30 mL) was heated under reflux using Dean-Stark apparatus for 3 h. The reaction was cooled, evaporated under reduced pressure, and the residue was dissolved in a small amount of DMF, diluted with chloroform, and washed with aq. sodium bicarbonate solution. The aqueous layer was extracted with chloroform, and the combined extracts were washed with brine, dried ($Na_2SO_4$), and concentrated in vacuo. Purification by flash chromatography (0-3% methanol in dichloromethane) followed by trituration in diethyl ether provided the title compound (1.75 g, 75%). $^1$H NMR (400 MHz, DMSO-$d_6$) δ ppm 7.95 (dd, J=8.72, 1.89 Hz, 1 H) 8.08 (d, J=8.84 Hz, 1 H) 8.38 (d, J=2.02 Hz, 1 H) 9.13 (d, J=1.52 Hz, 1 H) 9.21 (d, 1 H).

b) 2-(4-(3-cyanoquinolin-7-yl)-2-fluorophenyl)-2-(4-cyclopropyl-3-oxo-1-oxa-4,9-diazaspiro[5.5]undecan-9-yl)acetamide To a solution of 2-(4-bromo-2-fluorophenyl)-2-(4-cyclopropyl-3-oxo-1-oxa-4,9-diazaspiro[5.5]undecan-9-yl)acetamide (125 mg, 0.28 mmol) and 4,4,4',4',5,5,5',5'-octamethyl-2,2'-bi(1,3,2-dioxaborolane) (72 mg, 0.28 mmol) in 1,4-dioxane (2.0 mL) was added potassium acetate (61 mg, 0.63 mmol) and $PdCl_2$(dppf)-$CH_2Cl_2$ adduct (23 mg, 0.03 mmol). The reaction mixture was purged with nitrogen and heated at 120° C. for 4 h. The reaction mixture was cooled and 7-bromoquinoline-3-carbonitrile (66.2 mg, 0.28 mmol) and 2M aq $K_2CO_3$ (0.3 mL, 0.6 mmol) were added. The reaction mixture was purged with nitrogen and heated with stirring at 100° C. for 1 h. The cooled reaction mixture was diluted with dichloromethane (60 mL) and salts were filtered away. The organic mixture was filtered through a plug of celite and sodium sulfate and the filtrate was treated with a small amount of Silicycle Si-thiol resin for 30 min. The mixture was filtered and concentrated in vacuo. The residue was purified by reverse phase HPLC (10-70% acetonitrile:water with 0.1% $NH_4OH$) and the appropriate fractions were collected, combined and concentrated in vacuo to give expected product as a racemate (87 mg, 60%). Chiral HPLC was performed on this material in Example 63a. MS(ES)$^+$ m/e 514 [M+H]$^+$; $^1$H NMR (400 MHz, $CD_2Cl_2$) δ ppm 0.56-0.66 (m, 2 H) 0.75-0.87 (m, 2 H) 1.64-1.70 (m, 1 H) 1.72-1.77 (m, 1 H) 1.85-1.97 (m, 2 H) 2.31 (td, J=11.24, 2.53 Hz, 1 H) 2.56-2.61 (m, 1 H) 2.62-2.74 (m, 2 H) 2.77-2.86 (m, 1 H) 3.15 (s, 2 H) 4.00 (d, J=2.02 Hz, 2 H) 4.55 (s, 1 H) 5.65 (d, J=4.29 Hz, 1 H) 7.27 (d, J=4.04 Hz, 1 H) 7.49 (t, J=7.71 Hz, 1 H) 7.56 (d, J=1.77 Hz, 1 H) 7.65 (dd, J=7.96, 1.89 Hz, 1 H) 8.00 (dd, J=8.34, 1.77 Hz, 1 H) 8.06 (d, J=8.34 Hz, 1 H) 8.39-8.47 (m, 1 H) 8.63 (dd, J=2.02, 0.76 Hz, 1 H) 9.10 (d, J=2.27 Hz, 1 H).

Example 63

(+)-2-(4-(3-cyanoquinolin-7-yl)-2-fluorophenyl)-2-(4-cyclopropyl-3-oxo-1-oxa-4,9-diazaspiro[5.5]undecan-9-yl)acetamide a) Purification of the product from Example 62b using chiral HPLC (Chromegachiral CC4, methanol) afforded the title product in >98% ee (38 mg, 48% yield). $α_D$=+43 deg (c=0.05, methanol); MS(ES)$^+$ m/e 514 [M+H]$^+$; $^1$H NMR (400 MHz, $CD_2Cl_2$) δ ppm 0.58-0.71 (m, 2 H) 0.76-0.87 (m, 2 H) 1.63 (br. s., 2 H) 1.89-2.02 (m, 2 H) 2.32 (br. s., 1 H) 2.59 (s, 1 H) 2.65 (br. s., 1 H) 2.68-2.77 (m, 2 H) 2.82 (br. s., 1 H) 3.19 (br. s., 2 H) 4.02 (br. s., 2 H) 5.71 (br. s., 1 H) 7.29 (br. s., 1 H) 7.56-7.65 (m, 2 H) 7.65-7.78 (m, 1 H) 8.00 (d, J=1.77 Hz, 1 H) 8.03-8.11 (m, 1 H) 8.38-8.47 (m, 1 H) 8.64 (d, J=1.52 Hz, 1 H) 9.10 (d, J=2.02 Hz, 1 H).

Example 64

(−)-2-(4-(3-cyanoquinolin-7-yl)-2-fluorophenyl)-2-(4-cyclopropyl-3-oxo-1-oxa-4,9-diazaspiro[5.5]undecan-9-yl)acetamide a) From Example 63a, the title product was also isolated in >98% ee using chiral HPLC (Chromegachiral CC4, methanol) (38 mg, 48% yield). $α_D$=−44 deg (c=0.2, methanol); MS(ES)$^+$ m/e 514 [M+H]$^+$; $^1$H NMR (400 MHz, $CD_2Cl_2$) δ ppm 0.60-0.70 (m, 2 H) 0.77-0.85 (m, 2 H) 1.66 (br. s., 2 H) 1.86-1.99 (m, 2 H) 2.33 (br. s., 1 H) 2.65 (br. s., 2 H) 2.67-2.76 (m, 1 H) 2.82 (br. s., 1 H) 3.16 (s, 2 H) 3.95-4.07 (m, 2 H) 4.58 (br. s., 1 H) 5.74 (br. s., 1 H) 7.30 (br. s., 1 H) 7.51 (br. s., 1 H) 7.59 (d, J=1.77 Hz, 1 H) 7.65 (d, J=7.83 Hz, 1 H) 7.99 (d, J=1.77 Hz, 1 H) 8.03-8.10 (m, 1 H) 8.39-8.46 (m, 1 H) 8.63 (dd, J=2.02, 0.76 Hz, 1 H) 9.10 (d, J=2.02 Hz, 1 H).

Example 65

(+)-2-(4-(3-chloroquinolin-7-yl)-2-fluorophenyl)-2-(4-cyclopropyl-3-oxo-1-oxa-4,9-diazaspiro[5.5]undecan-9-yl)acetamide

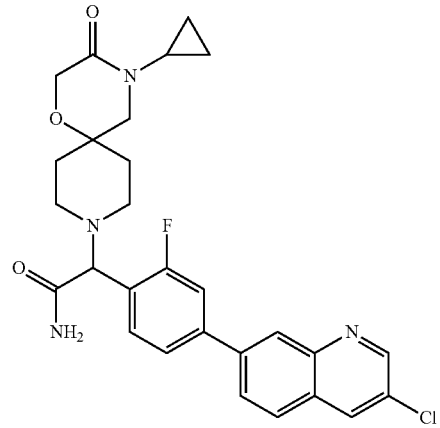 [SMILES: NC(=O)C(c1ccc(-c2ccc3cc(Cl)cnc3c2)cc1F)N1CCC2(CC1)CN(C1CC1)C(=O)CO2]

a) 7-bromo-3-chloroquinoline

Following the procedure described in Example 62a using 2-chloro-1,1-diethoxyethane afforded the title compound as a yellow solid (54%). $^1$H NMR (400 MHz, DMSO-d6) δ ppm 7.85 (dd, J=8.84, 2.02 Hz, 1 H), 7.98 (d, J=8.59 Hz, 1 H), 8.29 (d, J=1.77 Hz, 1 H), 8.65 (d, J=2.02 Hz, 1 H), 8.94 (d, J=2.53 Hz, 1 H).

b) (+)-2-(4-(3-chloroquinolin-7-yl)-2-fluorophenyl)-2-(4-cyclopropyl-3-oxo-1-oxa-4,9-diazaspiro[5.5]undecan-9-yl)acetamide To a solution of 7-bromo-3-chloroquinoline (100 mg, 0.41 mmol), bis(pinacolato)diboron (230 mg, 0.91 mmol) and potassium acetate (81 mg, 0.82 mmol) in 1,4-dioxane (2 mL) was added $PdCl_2$(dppf)-$CH_2Cl_2$ adduct (33.7 mg, 0.04 mmol). The reaction mixture was purged under nitrogen and then irradiated in the microwave at 100° C. for 4 h. The reaction mixture was cooled and diluted with dichloromethane (60 mL) and any salts were filtered away. The organic mixture was concentrated in vacuo onto silica gel and was purified by flash chromatography (15-100% ethyl acetate/hexanes). The appropriate fractions were collected and concentrated in vacuo to afford a crude mixture of 3-chloro-7-(4,4,5,5-tetramethyl-1,3,2-dioxaborolan-2-yl)quinoline and the corresponding boronic acid (45 mg), which was used directly in the next step. MS(ES)$^+$ m/e 290 [M+H]$^+$.

To a solution of 2-(4-bromo-2-fluorophenyl)-2-(4-cyclopropyl-3-oxo-1-oxa-4,9-diazaspiro[5.5]undecan-9-yl)acetamide (137 mg, 0.31 mmol), crude 3-chloro-7-(4,4,5,5-tetramethyl-1,3,2-dioxaborolan-2-yl)quinoline/boronic acid mixture (45.0 mg), and 2M aq potassium carbonate (0.17 mL, 0.342 mmol) in 1,4-dioxane (0.5 mL) was added PdCl$_2$(dppf)-CH$_2$Cl$_2$ adduct (10.2 mg, 0.012 mmol). The reaction mixture was purged with nitrogen, sealed, and irradiated in the microwave at 110° C. for 25 min, at which point the reaction had proceeded to completion. The reaction mixture was diluted with ethyl acetate (25 mL) and washed with 5 mL of 1M aq HCl. The organic phase was washed with brine (5 mL), dried over anhydrous sodium sulfate, filtered through a pad of celite, and concentrated to dryness. Purification of the residue by reverse phase HPLC (5-45% acetonitrile+0.1% TFA:water+0.1% TFA) followed by resolution of the racemate by chiral HPLC (Chromegachiral CC4, methanol) afforded the title product in >98% ee (9 mg, 4% yield over the two steps). $\alpha_D$=+41 deg (c=0.02, methanol); MS(ES)$^+$ m/e 523.5 [M+H]$^+$; $^1$H NMR (400 MHz, CD$_2$Cl$_2$) δ ppm 0.65 (br. s., 2 H) 0.82 (d, J=5.81 Hz, 2 H) 1.59 (br. s., 4 H) 1.92 (br. s., 1 H) 2.72 (br. s., 3 H) 3.16 (br. s., 3 H) 4.01 (br. s., 2 H) 4.53 (br. s., 1 H) 5.58 (s, 1 H) 7.27 (br. s., 1 H) 7.63 (br. s., 1 H) 7.92 (d, J=7.07 Hz, 2 H) 8.25 (d, J=2.02 Hz, 1 H) 8.35 (s, 1 H) 8.89 (d, J=2.27 Hz, 1 H).

Example 66

(−)-2-(4-(3-chloroquinolin-7-yl)-2-fluorophenyl)-2-(4-cyclopropyl-3-oxo-1-oxa-4,9-diazaspiro[5.5]undecan-9-yl)acetamide a) From Example 65b, the title product was also isolated in >98% ee using chiral HPLC (Chromegachiral CC4, methanol) followed by concentration in vacuo and lyophilization (14 mg, 7% yield). $\alpha_D$=−40 deg (c=0.015, methanol); MS(ES)$^+$ m/e 514 [M+H]$^+$.

Example 67

2-(4-cyclopropyl-3-oxo-1-oxa-4,9-diazaspiro[5.5]undecan-9-yl)-2-(2-fluoro-4-(8-fluoroquinolin-7-yl)phenyl)acetamide a) Following the procedure of Example 62b using 7-bromo-8-fluoroquinoline provided the title racemic product as an off-white solid (123 mg, 85% yield). Chiral HPLC was performed on this material in Example 68a. MS(ES)$^+$ m/e 507 [M+H]$^+$; $^1$H NMR (400 MHz, CD$_2$Cl$_2$) δ ppm 0.61-0.68 (m, 2 H) 0.75-0.87 (m, 2 H) 1.62-1.71 (m, 1 H) 1.72-1.77 (m, 1 H) 1.86-1.98 (m, 2 H) 2.30-2.40 (m, 1 H) 2.64-2.75 (m, 3 H) 2.82 (br. s., 1 H) 3.15 (s, 2 H) 4.02 (d, J=1.26 Hz, 2 H) 4.53 (s, 1 H) 5.74 (br. s., 1 H) 7.25 (br. s., 1 H) 7.46-7.58 (m, 4 H) 7.70 (d, J=6.82 Hz, 1 H) 7.74-7.80 (m, 1 H) 8.28 (dt, J=8.34, 1.52 Hz, 1 H) 9.03 (dd, J=4.17, 1.64 Hz, 1 H).

Example 68

(+)-2-(4-cyclopropyl-3-oxo-1-oxa-4,9-diazaspiro[5.5]undecan-9-yl)-2-(2-fluoro-4-(8-fluoroquinolin-7-yl)phenyl)acetamide a) Purification of the product from Example 67a using chiral HPLC (Lux Cell-4, methanol) afforded the title product in >99.9% ee (36 mg, 29% yield). $\alpha_D$=+3.7 deg (c=1.2, methanol); MS(ES)$^+$ m/e 507 [M+H]$^+$; $^1$H NMR (400 MHz, CD$_2$Cl$_2$) δ ppm 0.59-0.68 (m, 2 H) 0.78-0.87 (m, 2 H) 1.61-1.73 (m, 2 H) 1.86-1.90 (m, 1 H) 1.90-1.94 (m, 1 H) 2.34 (td, J=11.24, 2.02 Hz, 1 H) 2.64-2.75 (m, 3 H) 2.80 (d, J=11.62 Hz, 1 H) 3.15 (s, 2 H) 4.02 (d, J=1.26 Hz, 2 H) 4.53 (s, 1 H) 5.70 (d, J=4.29 Hz, 1 H) 7.26 (d, J=3.79 Hz, 1 H) 7.46-7.58 (m, 4 H) 7.70 (d, J=6.82 Hz, 1 H) 7.76 (d, J=0.76 Hz, 1 H) 8.28 (dt, J=8.34, 1.64 Hz, 1 H) 9.03 (dd, J=4.17, 1.64 Hz, 1 H).

Example 69

(−)-2-(4-cyclopropyl-3-oxo-1-oxa-4,9-diazaspiro[5.5]undecan-9-yl)-2-(2-fluoro-4-(8-fluoroquinolin-7-yl)phenyl)acetamide a) From Example 68a, the title product was also isolated in 99.2% ee using chiral HPLC (Lux Cell-4, methanol) (34 mg, 28% yield). $\alpha_D$=−10 deg (c=0.4, methanol); MS(ES)$^+$ m/e 507 [M+H]$^+$; $^1$H NMR (400 MHz, CD$_2$Cl$_2$) δ ppm 0.62-0.70 (m, 2 H) 0.79-0.86 (m, 2 H) 1.72-1.77 (m, 2 H) 1.87-1.98 (m, 2 H) 2.31-2.39 (m, 1 H) 2.58-2.65 (m, 1 H) 2.65-2.75 (m, 2 H) 2.80 (d, J=11.62 Hz, 1 H) 3.16 (s, 2 H) 3.97-4.06 (m, 2 H) 4.54 (s, 1 H) 5.62 (br. s., 1 H) 7.23-7.30 (m, 1 H) 7.48-7.58 (m, 4 H) 7.70 (d, J=6.82 Hz, 1 H) 7.77 (d, J=8.84 Hz, 1 H) 8.28 (dt, J=8.34, 1.52 Hz, 1 H) 9.03 (dd, J=4.17, 1.64 Hz, 1 H).

Example 70

2-(2,6-difluoro-4-(quinolin-7-yl)phenyl)-2-(4-ethyl-3-oxo-1-oxa-4,9-diazaspiro[5.5]undecan-9-yl)acetamide

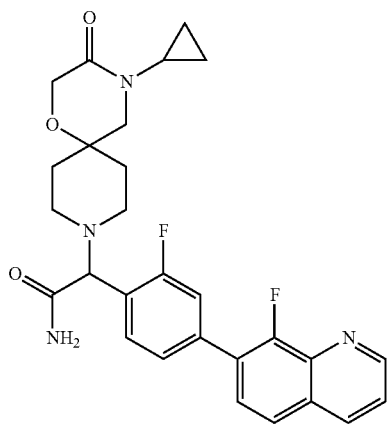 [SMILES: NC(=O)C(c1ccc(-c2ccc3cccnc3c2F)cc1F)N1CCC2(CC1)CN(C1CC1)C(=O)CO2]

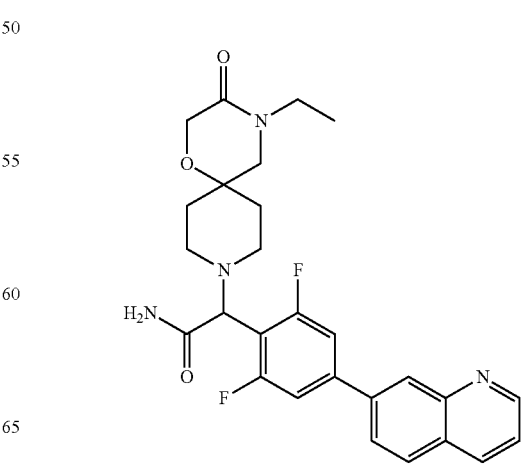

a) 2-(4-bromo-2,6-difluorophenyl)-2-hydroxyacetamide

To a solution of cyanopotassium (4.4 g, 67.9 mmol) and ammonium chloride (9.1 g, 170 mmol) in water (30 mL) was added 4-bromo-2,6-difluorobenzaldehyde (7.5 g, 33.9 mmol) followed by diethyl ether (60.0 mL). The reaction mixture was stirred vigorously at room temperature for 30 min. Analysis of the reaction by TLC indicated aldehyde starting material still remained. Acetic acid (5.5 mL, 49.4 mmol) was added to give a reaction pH of about 6. After 30 min, analysis by TLC indicated the aldehyde starting material had been consumed. The reaction mixture was diluted with water and the two phases were separated. The aqueous phase was extracted with ether. The combined ether phases were dried over sodium sulfate and evaporated under reduced pressure to give the intermediate cyanohydrin as a light yellow solid. To a solution of the crude cyanohydrin in 1,4-dioxane (40 mL) was added concentrated hydrochloric acid (15 mL, 493 mmol). The reaction was stirred at 90° C. for 45 min, at which point the reaction had proceeded to completion. The reaction mixture was poured into ice-cold water (100 mL) and the cloudy solution was extracted with ethyl acetate (2×120 mL). The combined organic extracts were washed with saturated aqueous sodium bicarbonate (2×15 mL) and brine (15 mL) and then dried over anhydrous sodium sulfate, filtered, and evaporated under reduced pressure to afford the title product (6.1 g, 68%) as a light yellow solid. MS(ES)$^+$ m/e 266 [M+H]$^+$; $^1$H NMR (400 MHz, DMSO-d$_6$) δ ppm 5.12 (d, J=5.56 Hz, 1 H) 6.48 (d, J=5.31 Hz, 1 H) 7.45 (d, J=7.58 Hz, 2 H) 7.49 (d, J=7.83 Hz, 2 H).

b) tert-butyl 4-((ethylamino)methyl)-4-hydroxypiperidine-1-carboxylate

Into a 100 mL round bottom flask was placed tert-butyl 1-oxa-6-azaspiro[2.5]octane-6-carboxylate (2 g, 9.38 mmol). To this was added 2M ethanamine in methanol (23.44 ml, 46.9 mmol). A condenser was attached to the flask and the solution was stirred at reflux (100° C.) overnight. The solution was cooled and concentrated in vacuo to afford the title compound (2.4 g) which was carried forward without further purification. MS(ES)+ m/e 259.1 [M+H]$^+$.

c) tert-butyl 4-((2-chloro-N-ethylacetamido)methyl)-4-hydroxypiperidine-1-carboxylate To a 100 mL round bottom flask containing tert-butyl 4-((ethylamino)methyl)-4-hydroxypiperidine-1-carboxylate (2.4 g) was added dichloromethane (30 mL) and triethylamine (3 mL, 21.52 mmol). An addition funnel was attached to the flask. The vessel was placed under nitrogen and the solution was cooled to 0° C. with an ice bath. In a separate vial, chloroacetyl chloride (1 mL, 12.48 mmol) was diluted with dichloromethane (20 mL) and transferred to the addition funnel. This mixture was added dropwise to the cold starting material over 10 min. The reaction mixture was then allowed to stir under nitrogen for 3 h while slowly allowing the ice bath to warm to room temperature. The reaction mixture was diluted with dichloromethane (100 mL) and was washed with water (2×50 mL) and brine (1×50 mL). The organic layer was separated, dried over sodium sulfate, filtered, and concentrated in vacuo to afford the title compound (3.23 g) which was carried forward without further purification. MS(ES)+ m/e 335.2 [M+H]$^+$.

d) tert-butyl 4-ethyl-3-oxo-1-oxa-4,9-diazaspiro[5.5]undecane-9-carboxylate

To a 250 mL round bottom flask containing tert-butyl 4-((2-chloro-N-ethylacetamido)methyl)-4-hydroxypiperidine-1-carboxylate (3.14 g) was added tetrahydrofuran (50 mL). The entire vessel was placed under nitrogen and stirred at room temperature. To this was portionwise added NaH (60% in mineral oil, 2 g, 50.0 mmol). After complete addition, the reaction mixture was stirred at room temperature. After 3 hours, saturated aq sodium bicarbonate (70 mL) was added to the flask (slowly dropwise via pipette at first, then the final 60 mL can be added directly). The solution was transferred to a reparatory funnel containing ethyl acetate (150 mL) and water (50 mL). The organic layer was washed with the aqueous solution, separated, and set aside. The aqueous layer was washed with ethyl acetate (1×50 mL). The combined organic extracts were washed with brine (2×50 mL), separated, dried over sodium sulfate, filtered, and concentrated in vacuo. Purification of the residue by flash chromatography (50-100% ethyl acetate:hexanes) afforded the title compound (1.7 g, 61%). MS(ES)+ m/e 299.5 [M+H]$^+$.

e) 4-ethyl-1-oxa-4,9-diazaspiro[5.5]undecan-3-one hydrochloride

To a 100 mL round bottom flask containing tert-butyl 4-ethyl-3-oxo-1-oxa-4,9-diazaspiro[5.5]undecane-9-carboxylate (800 mg, 2.68 mmol) was added 4M HCl in dioxane (10 mL, 40.0 mmol). The reaction mixture was placed under a nitrogen atmosphere and stirred at room temperature. After 1 h, analysis by LCMS indicated the reaction had gone to completion. The reaction mixture was concentrated in vacuo to afford the title compound as the HCl salt, which was carried forward without further purification. MS(ES)+ m/e 199.0 [M+H]$^+$.

f) 2-(4-bromo-2,6-difluorophenyl)-2-(4-ethyl-3-oxo-1-oxa-4,9-diazaspiro[5.5]undecan-9-yl)acetamide To a solution of 2-(4-bromo-2,6-difluorophenyl)-2-hydroxyacetamide (0.86 g, 3.2 mmol) and triethylamine (1.4 mL, 9.7 mmol) in anhydrous acetonitrile (5 mL) was added neat methanesulfonyl chloride (0.33 mL, 4.2 mmol). The reaction mixture was stirred vigorously at 40° C. for 3 h, at which point the reaction had progressed to completion. To this mesylate intermediate mixture was added more triethylamine (1.4 mL, 9.7 mmol) followed by 4-ethyl-1-oxa-4,9-diazaspiro[5.5]undecan-3-one hydrochloride (0.11 g, 0.48 mmol). The reaction mixture was heated at 90° C. for 3 h until the starting material was consumed. The reaction was diluted with water and was extracted with ether (3×35 mL). The combined ether phases were dried over sodium sulfate, filtered, and evaporated under reduced pressure. Purification of the residue by flash chromatography (65-100% of 10% methanol in dichloromethane:dichloromethane) afforded the title product (261 mg, 18% yield). MS(ES)$^+$ m/e 446 [M+H]$^+$; $^1$H NMR (400 MHz, CD$_2$Cl$_2$) δ ppm 1.12 (t, J=7.20 Hz, 3 H) 1.64-1.71 (m, 1 H) 1.73 (dd, J=4.17, 2.65 Hz, 1 H) 1.90-1.99 (m, 2 H) 2.19-2.27 (m, 1 H) 2.54-2.66 (m, 1 H) 2.67-2.73 (m, 1 H) 2.75-2.81 (m, 1 H) 3.15 (s, 2 H) 3.41 (q, J=6.91 Hz, 2 H) 3.98 (s, 2 H) 4.69 (s, 1 H) 5.68 (br. s., 1 H) 7.15-7.25 (m, 2 H) 7.36 (br. s., 1 H).

g) 2-(2,6-difluoro-4-(quinolin-7-yl)phenyl)-2-(4-ethyl-3-oxo-1-oxa-4,9-diazaspiro[5.5]undecan-9-yl)acetamide To a solution of 2-(4-bromo-2,6-difluorophenyl)-2-(4-ethyl-3-oxo-1-oxa-4,9-diazaspiro[5.5]undecan-9-yl)acetamide (252 mg, 0.57 mmol), 7-(4,4,5,5-tetramethyl-1,3,2-dioxaborolan-2-yl)quinoline (144 mg, 0.57 mmol) and 2M aq $K_2CO_3$ (0.62 mL, 1.24 mmol) in 1,4-dioxane (2.5 mL) was added $PdCl_2$(dppf)-$CH_2Cl_2$ adduct (23 mg, 0.03 mmol). The reaction mixture was purged with nitrogen, sealed, and irradiated in the microwave at 110° C. for 25 min, at which point the reaction had proceeded to completion. The reaction mixture was diluted with ethyl acetate (25 mL) and washed with 5 mL of 1M aq HCl. The organic phase was washed with brine (5 mL), dried over anhydrous sodium sulfate, filtered through a pad of celite, and concentrated in vacuo. Purification of the residue by reverse phase HPLC (25-55% acetonitrile+0.1% TFA:water+0.1% TFA) afforded the title product as a trifluoroacetate salt (163 mg, 47% yield). $MS(ES)^+$ m/e 495 $[M+H]^+$; $^1H$ NMR (400 MHz, $CD_2Cl_2$) δ ppm 1.12 (t, J=7.20 Hz, 3 H) 1.69-1.81 (m, 2 H) 1.92-2.04 (m, 2 H) 2.31-2.39 (m, 1 H) 2.64-2.74 (m, 1 H) 2.75-2.83 (m, 1 H) 2.87 (d, J=12.38 Hz, 1 H) 3.17 (s, 2 H) 3.41 (q, J=7.07 Hz, 2 H) 3.99 (s, 2 H) 4.79 (s, 1 H) 5.65 (d, J=4.04 Hz, 1 H) 7.39-7.46 (m, 3 H) 7.49 (dd, J=8.34, 4.29 Hz, 1 H) 7.85 (dd, J=8.46, 1.89 Hz, 1 H) 8.00 (d, J=8.59 Hz, 1 H) 8.26 (dd, J=8.46, 1.14 Hz, 1 H) 8.36 (d, J=1.77 Hz, 1 H) 8.99 (dd, J=4.29, 1.77 Hz, 1 H).

Example 71

(+)-2-(2,6-difluoro-4-(quinolin-7-yl)phenyl)-2-(4-ethyl-3-oxo-1-oxa-4,9-diazaspiro[5.5]undecan-9-yl)acetamide a) From Example 70 g, the title product was isolated in >99.9% ee using chiral HPLC (Chiralpak IC, 60:40 heptane:ethanol) (29 mg, 22% yield). $α_D$=+23 deg (c=0.18, methanol); $MS(ES)^+$ m/e 495 $[M+H]^+$; $^1H$ NMR (400 MHz, $CD_2Cl_2$) δ ppm 1.12 (t, J=7.20 Hz, 3 H) 1.70-1.81 (m, 2 H) 1.99 (s, 2 H) 2.31-2.39 (m, 1 H) 2.63-2.75 (m, 1 H) 2.75-2.84 (m, 1 H) 2.88 (d, J=11.87 Hz, 1 H) 3.18 (s, 2 H) 3.41 (q, J=7.16 Hz, 2 H) 3.99 (s, 2 H) 4.79 (s, 1 H) 5.69 (br. s., 1 H) 7.43 (d, J=9.60 Hz, 2 H) 7.45 (s, 1 H) 7.49 (dd, J=8.21, 4.17 Hz, 1 H) 7.82-7.91 (m, 1 H) 8.00 (d, J=8.59 Hz, 1 H) 8.27 (d, J=8.34 Hz, 1 H) 8.36 (s, 1 H) 8.99 (dd, J=4.04, 1.77 Hz, 1 H).

Example 72

(−)-2-(2,6-difluoro-4-(quinolin-7-yl)phenyl)-2-(4-ethyl-3-oxo-1-oxa-4,9-diazaspiro[5.5]undecan-9-yl)acetamide a) From Example 71a, the title product was also isolated in 99.3% ee using chiral HPLC (Chiralpak IC, 60:40 heptane:ethanol) (31 mg, 23% yield). $α_D$=−38 deg (c=0.16, methanol); $MS(ES)^+$ m/e 495 $[M+H]^+$; $^1H$ NMR (400 MHz, $CD_2Cl_2$) δ ppm 1.12 (t, J=7.20 Hz, 3 H) 1.69-1.81 (m, 2 H) 1.93-2.02 (m, 2 H) 2.35 (t, J=10.61 Hz, 1 H) 2.63-2.74 (m, 1 H) 2.74-2.83 (m, 1 H) 2.87 (d, J=11.37 Hz, 1 H) 3.17 (s, 2 H) 3.41 (q, J=7.33 Hz, 2 H) 3.99 (s, 2 H) 4.79 (s, 1 H) 5.73 (br. s., 1 H) 7.38-7.47 (m, 3 H) 7.49 (dd, J=8.34, 4.29 Hz, 1 H) 7.85 (dd, J=8.46, 1.89 Hz, 1 H) 8.00 (d, J=8.59 Hz, 1 H) 8.25 (d, J=1.01 Hz, 1 H) 8.36 (d, J=2.02 Hz, 1 H) 8.99 (dd, J=4.29, 1.77 Hz, 1 H).

Example 73

(+)-2-(4-cyclopropyl-3-oxo-1-oxa-4,9-diazaspiro[5.5]undecan-9-yl)-2-(2,6-difluoro-4-(quinolin-7-yl)phenyl)acetamide

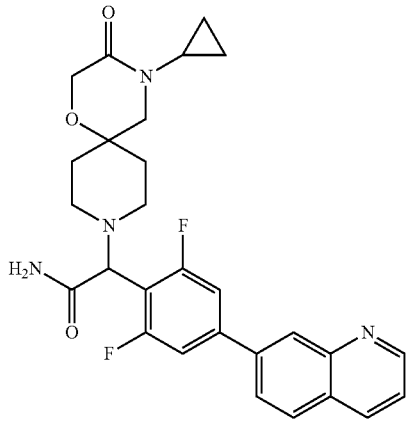 [SMILES: NC(=O)C(c1c(F)cc(-c2ccc3cccnc3c2)cc1F)N1CCC2(CC1)CN(C1CC1)C(=O)CO2]

a) 2-(4-bromo-2,6-difluorophenyl)-2-(4-cyclopropyl-3-oxo-1-oxa-4,9-diazaspiro[5.5]undecan-9-yl)acetamide To a solution of 2-(4-bromo-2,6-difluorophenyl)-2-hydroxyacetamide (4.56 g, 17.1 mmol) and triethylamine (7.17 mL, 51.4 mmol) in anhydrous acetonitrile (25 mL) was added neat methanesulfonyl chloride (1.7 mL, 22.3 mmol). The reaction mixture was stirred vigorously at 40° C. for 3 h, at which point the reaction had proceeded to completion. To the mesylate intermediate was added more triethylamine (7.2 mL, 51.4 mmol) followed by 4-cyclopropyl-1-oxa-4,9-diazaspiro[5.5]undecan-3-one hydrochloride (4.23 g, 17.1 mmol). The reaction was heated at 90° C. for 3 h until starting material was consumed. The reaction was diluted with water (25 mL) then the phases were separated and the aqueous phase was extracted with ether (3×25 mL). The combined ether phases were dried over anhydrous sodium sulfate, filtered, and concentrated in vacuo. Purification of the residue by flash chromatography (65-100% of 10% methanol in dichloromethane:dichloromethane) provided the title product (1.26 g, 16% yield). $MS(ES)^+$ m/e 458 $[M+H]^+$; $^1H$ NMR (400 MHz, $CD_2Cl_2$) δ ppm 0.59-0.69 (m, 2 H) 0.75-0.86 (m, 2 H) 1.61-1.74 (m, 2 H) 1.85-1.95 (m, 2 H) 2.21 (s, 1 H) 2.53-2.64 (m, 2 H) 2.66-2.76 (m, 3 H) 2.79 (br. s., 1 H) 3.96 (s, 2 H) 4.68 (s, 1 H) 5.64 (br. s., 1 H) 7.16-7.26 (m, 2 H) 7.35 (br. s., 1 H).

b) (+)-2-(4-cyclopropyl-3-oxo-1-oxa-4,9-diazaspiro[5.5]undecan-9-yl)-2-(2,6-difluoro-4-(quinolin-7-yl)phenyl)acetamide To a solution of 2-(4-bromo-2,6-difluorophenyl)-2-(4-cyclopropyl-3-oxo-1-oxa-4,9-diazaspiro[5.5]undecan-9-yl)acetamide (246 mg, 0.54 mmol), 7-(4,4,5,5-tetramethyl-1,3,2-dioxaborolan-2-yl)quinoline (137 mg, 0.54 mmol) and 2M aq $K_2CO_3$ (0.59 mL, 1.18 mmol) in 1,4-dioxane (2.5 mL) was added $PdCl_2$(dppf)-$CH_2Cl_2$ adduct (21.9 mg, 0.03 mmol). The reaction mixture was purged with nitrogen, sealed, and irradiated in the microwave at 110° C. for 25 min, at which point the reaction had proceeded to completion. The reaction mixture was diluted with ethyl acetate (25 mL) and washed with 5 mL of 1M aq HCl. The organic phase was washed with brine (5 mL), dried over anhydrous sodium sulfate, filtered through a pad of celite, and concentrated in vacuo. Purification of the residue with reverse phase HPLC (10-70% acetonitrile:water with 0.1% $NH_4OH$) followed by chiral HPLC (Lux Cell 4, methanol) afforded the title product in 99.9% ee (61 mg, 22% yield). $\alpha_D$=+30 deg (c=0.1, methanol); MS(ES)$^+$ m/e 507 [M+H]$^+$; $^1$H NMR (400 MHz, $CD_2Cl_2$) δ ppm 0.58-0.71 (m, 2 H) 0.76-0.87 (m, 2 H) 1.65 (dd, J=11.12, 4.29 Hz, 1 H) 1.71-1.81 (m, 1 H) 1.95 (s, 1 H) 1.92 (s, 1 H) 2.29-2.38 (m, 1 H) 2.64-2.75 (m, 2 H) 2.75-2.84 (m, 1 H) 2.84-2.96 (m, 1 H) 3.14 (s, 2 H) 3.98 (s, 2 H) 4.78 (s, 1 H) 5.68 (br. s., 1 H) 7.40-7.47 (m, 3 H) 7.49 (dd, J=8.21, 4.17 Hz, 1 H) 7.85 (dd, J=8.59, 2.02 Hz, 1 H) 8.00 (d, J=8.59 Hz, 1 H) 8.27 (d, J=8.34 Hz, 1 H) 8.36 (s, 1 H) 8.99 (dd, J=4.29, 1.77 Hz, 1 H).

Example 74

(−)-2-(4-cyclopropyl-3-oxo-1-oxa-4,9-diazaspiro [5.5]undecan-9-yl)-2-(2,6-difluoro-4-(quinolin-7-yl) phenyl)acetamide a) Following Example 73b, the title product was also isolated in 99.3% ee using chiral HPLC (Lux Cell 4, methanol) (59 mg, 21% yield). $\alpha_D$=−33.3 deg (c=0.3, methanol); MS(ES)$^+$ m/e 507 [M+H]$^+$; $^1$H NMR (400 MHz, $CD_2Cl_2$) δ ppm 0.61-0.66 (m, 2 H) 0.77-0.86 (m, 2 H) 1.66-1.78 (m, 2 H) 1.86-1.97 (m, 2 H) 2.32 (t, J=10.61 Hz, 1 H) 2.63-2.75 (m, 2 H) 2.75-2.82 (m, 1 H) 2.87 (d, J=11.12 Hz, 1 H) 3.14 (s, 2 H) 3.98 (s, 2 H) 4.78 (s, 1 H) 5.85 (d, J=4.29 Hz, 1 H) 7.39-7.46 (m, 3 H) 7.49 (dd, J=8.34, 4.29 Hz, 1 H) 7.85 (dd, J=8.59, 1.77 Hz, 1 H) 8.00 (d, J=8.59 Hz, 1 H) 8.26 (dd, J=8.46, 0.88 Hz, 1 H) 8.34-8.39 (m, 1 H) 8.99 (dd, J=4.17, 1.64 Hz, 1 H).

Example 75

(+)-2-(4-cyclopropyl-3-oxo-1-oxa-4,9-diazaspiro [5.5]undecan-9-yl)-2-(2-fluoro-4-(3-methoxyquinolin-7-yl)phenyl)acetamide

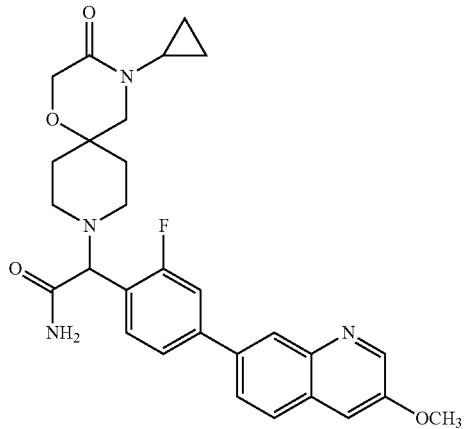 [SMILES: COc1cnc2cc(-c3ccc(C(C(N)=O)N4CCC5(CC4)CN(C4CC4)C(=O)CO5)c(F)c3)ccc2c1]

a) Following the procedure of Example 60d using 7-bromo-3-methoxyquinoline provided the title product as a racemate, which was resolved using chiral HPLC (Chromegachiral CC4, methanol) to afford the title product as an off-white solid in >98% ee (20 mg, 15% yield). $\alpha_D$=+49 deg (c=0.05, methanol); MS(ES)$^+$ m/e 519 [M+H]$^+$; $^1$H NMR (400 MHz, $CD_2Cl_2$) δ ppm 0.59-0.71 (m, 2 H) 0.82 (d, J=6.06 Hz, 2 H) 1.64-1.76 (m, 2 H) 1.91 (t, J=15.03 Hz, 2 H) 2.27-2.40 (m, 1 H) 2.62-2.67 (m, 1 H) 2.72 (ddd, J=10.93, 7.01, 4.04 Hz, 2 H) 2.76-2.80 (m, 1 H) 3.15 (br. s., 2 H) 4.01 (s, 5 H) 4.52 (br. s., 1 H) 5.58 (br. s., 1 H) 7.26 (br. s., 1 H) 7.49 (d, J=2.78 Hz, 2 H) 7.52-7.59 (m, 1 H) 7.62 (br. s., 1 H) 7.79-7.87 (m, 1 H) 7.90 (d, J=8.34 Hz, 1 H) 8.30 (s, 1 H) 8.72 (d, J=2.78 Hz, 1 H).

Example 76

(−)-2-(4-cyclopropyl-3-oxo-1-oxa-4,9-diazaspiro [5.5]undecan-9-yl)-2-(2-fluoro-4-(3-methoxyquinolin-7-yl)phenyl)acetamide a) Following Example 75a, the title product was also isolated in >98% ee using chiral HPLC (Chromegachiral CC4, methanol) (20 mg, 15% yield). $\alpha_D$=−67 deg (c=0.07, methanol); MS(ES)$^+$ m/e 519 [M+H]$^+$; $^1$H NMR (400 MHz, $CD_2Cl_2$) δ ppm 0.59-0.71 (m, 2 H) 0.77-0.88 (m, 2 H) 1.75 (s, 1 H) 1.72 (s, 1 H) 1.93 (br. s., 2 H) 2.33 (br. s., 1 H) 2.65 (d, J=6.57 Hz, 1 H) 2.72 (ddd, J=11.12, 7.33, 4.04 Hz, 3 H) 3.16 (br. s., 2 H) 4.01 (s, 5 H) 4.52 (br. s., 1 H) 5.60 (d, J=17.94 Hz, 1 H) 7.27 (br. s., 1 H) 7.49 (d, J=3.03 Hz, 2 H) 7.53 (s, 1 H) 7.64 (br. s., 1 H) 7.78-7.86 (m, 1 H) 7.90 (d, J=8.59 Hz, 1 H) 8.30 (s, 1 H) 8.72 (d, J=2.78 Hz, 1 H).

Example 77

(+)-2-(4-cyclopropyl-3-oxo-1-oxa-4,9-diazaspiro [5.5]undecan-9-yl)-2-(2-fluoro-4-(8-methoxyquinolin-7-yl)phenyl)acetamide

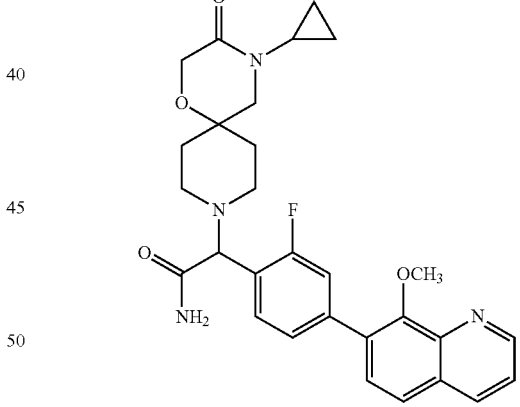

a) Following the procedure of Example 62b using 7-bromo-8-methoxyquinoline provided the title product as a racemate, which was resolved using chiral HPLC (Lux Cell 4, methanol) to afford the title product as an off-white solid in >98% ee (31 mg, 21% yield). $\alpha_D$=+31 deg (c=1.2, methanol); MS(ES)$^+$ m/e 519 [M+H]$^+$; $^1$H NMR (400 MHz, $CD_2Cl_2$) δ ppm 0.61-0.69 (m, 2 H) 0.77-0.87 (m, 2 H) 1.64-1.75 (m, 2 H) 1.86-1.98 (m, 2 H) 2.29-2.41 (m, 1 H) 2.57-2.68 (m, 2 H) 2.68-2.75 (m, 1 H) 2.75-2.85 (m, 1 H) 3.16 (s, 2 H) 4.02 (d, J=1.77 Hz, 2 H) 4.04 (s, 3 H) 4.51 (s, 1 H) 5.61 (br. s., 1 H) 7.23-7.31 (m, 1 H) 7.42-7.54 (m, 4 H) 7.61 (d, J=8.34 Hz, 1 H) 7.70 (d, J=8.59 Hz, 1 H) 8.24 (dd, J=8.21, 1.64 Hz, 1 H) 8.99 (dd, J=4.29, 1.77 Hz, 1 H).

Example 78

(−)-2-(4-cyclopropyl-3-oxo-1-oxa-4,9-diazaspiro[5.5]undecan-9-yl)-2-(2-fluoro-4-(8-methoxyquinolin-7-yl)phenyl)acetamide a) Following Example 77a, the title product was also isolated in >98% ee using chiral HPLC (Lux Cell 4, methanol) (34 mg, 23% yield). $\alpha_D=-18$ deg (c=0.7, methanol); MS(ES)$^+$ m/e 519 [M+H]$^+$; $^1$H NMR (400 MHz, CD$_2$Cl$_2$) δ ppm 0.60-0.68 (m, 2 H) 0.77-0.86 (m, 2 H) 1.63-1.71 (m, 1 H) 1.73-1.77 (m, 1 H) 1.85-1.97 (m, 2 H) 2.30-2.41 (m, 1 H) 2.58-2.69 (m, 2 H) 2.69-2.76 (m, 1 H) 2.76-2.84 (m, 1 H) 3.16 (s, 2 H) 4.02 (d, J=1.77 Hz, 2 H) 4.04 (s, 3 H) 4.51 (s, 1 H) 5.62 (d, J=4.55 Hz, 1 H) 7.24-7.29 (m, 1 H) 7.42-7.54 (m, 4 H) 7.61 (d, J=8.59 Hz, 1 H) 7.70 (d, J=8.34 Hz, 1 H) 8.24 (dd, J=8.34, 1.77 Hz, 1 H) 8.99 (dd, J=4.29, 1.77 Hz, 1 H).

Example 79

4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one

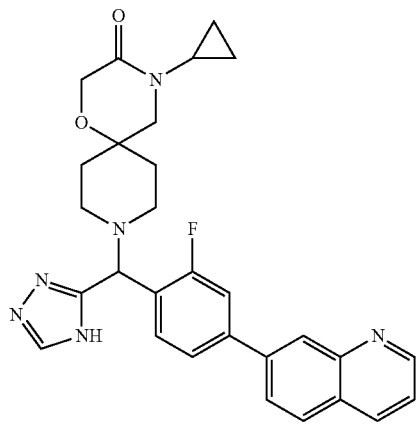 [SMILES: O=C1COC2(CCN(C(c3nnc[nH]3)c3ccc(-c4ccc5cccnc5c4)cc3F)CC2)CN1C1CC1]

a) To 1,1-dimethoxy-N,N-dimethylmethanamine (5 g, 42 mmol) was added 2-(4-cyclopropyl-3-oxo-1-oxa-4,9-diazaspiro[5.5]undecan-9-yl)-2-(2-fluoro-4-(quinolin-7-yl)phenyl)acetamide (245 mg, 0.5 mmol). The reaction mixture was heated with stirring at 105° C. overnight and then was concentrated under reduced pressure. To the crude intermediate was added acetic acid (10 mL) and hydrazine hydrate (75 mg, 1.5 mmol). The resulting reaction mixture was heated with stirring at 110° C. for 2 h, at which point the reaction had proceeded to completion. The reaction mixture was concentrated in vacuo and the residue was purified by reverse phase HPLC (10-45% acetonitrile+0.1% TFA:water+0.1% TFA) to afford the title product as a trifluoroacetate salt (114 mg, 36%). MS(ES)$^+$ m/e 513 [M+H]$^+$; $^1$H NMR (400 MHz, CD$_2$Cl$_2$) δ ppm 0.61-0.68 (m, 2 H) 0.78-0.87 (m, 2 H) 2.01-2.13 (m, 2 H) 2.18-2.30 (m, 2 H) 2.72 (m, J=7.26, 7.26, 4.04, 3.66 Hz, 1 H) 3.11-3.21 (m, 1 H) 3.25 (s, 2 H) 3.32-3.42 (m, 1 H) 3.48-3.57 (m, 1 H) 3.71 (d, J=12.13 Hz, 1 H) 4.08 (s, 2 H) 6.14 (s, 1 H) 7.61 (s, 1 H) 7.68 (d, J=8.59 Hz, 1 H) 7.90 (dd, J=8.34, 5.05 Hz, 1 H) 8.08 (dd, J=8.72, 1.64 Hz, 1 H) 8.19-8.29 (m, 2 H) 8.35 (s, 1 H) 8.75 (s, 1 H) 8.82 (d, J=8.34 Hz, 1 H) 9.21 (dd, J=5.05, 1.52 Hz, 1 H).

Example 80

(+)-4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one a) From Example 79a, the title product was isolated in >99.9% ee using chiral HPLC (Lux Cell 4, methanol) (26 mg, 27% yield). $\alpha_D=+18$ deg (c=0.07, methanol); MS(ES)$^+$ m/e 513 [M+H]$^+$; $^1$H NMR (400 MHz, CD$_2$Cl$_2$) δ ppm 0.56-0.69 (m, 2 H) 0.74-0.86 (m, 2 H) 1.60-1.73 (m, 2 H) 1.77-1.89 (m, 2 H) 2.38-2.49 (m, 1 H) 2.51-2.61 (m, 1 H) 2.64-2.76 (m, 3 H) 3.11 (s, 2 H) 4.03 (s, 2 H) 5.32 (s, 1 H) 7.45-7.51 (m, 2 H) 7.60 (dd, J=8.21, 1.89 Hz, 1 H) 7.81 (br. s., 1 H) 7.83 (dd, J=8.46, 1.89 Hz, 2 H) 7.97 (d, J=8.59 Hz, 1 H) 8.12 (s, 1 H) 8.26 (dd, J=8.34, 1.01 Hz, 1 H) 8.33-8.40 (m, 1 H) 8.98 (dd, J=4.17, 1.64 Hz, 1 H).

Example 81

(−)-4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one a) From Example 80a, the title product was also isolated in 99.6% ee using chiral HPLC (Lux Cell 4, methanol) (26 mg, 27% yield). $\alpha_D=-32$ deg (c=0.07, methanol); MS(ES)$^+$ m/e 513 [M+H]$^+$; $^1$H NMR (400 MHz, CD$_2$Cl$_2$) δ ppm 0.60-0.68 (m, 2 H) 0.75-0.86 (m, 2 H) 1.64-1.77 (m, 2 H) 1.79-1.91 (m, 2 H) 2.46 (t, J=10.48 Hz, 1 H) 2.55-2.66 (m, 1 H) 2.67-2.80 (m, 3 H) 3.13 (s, 2 H) 4.03 (s, 2 H) 7.45-7.55 (m, 2 H) 7.62 (dd, J=8.08, 1.77 Hz, 1 H) 7.77-7.82 (m, 1 H) 7.84 (dd, J=8.59, 1.77 Hz, 1 H) 7.98 (d, J=8.59 Hz, 1 H) 8.10 (s, 3 H) 8.27 (dd, J=8.34, 1.01 Hz, 1 H) 8.34-8.38 (m, 1 H) 8.98 (dd, J=4.17, 1.64 Hz, 1 H).

Example 82

2-(4-(3-cyanoquinolin-7-yl)-2-fluorophenyl)-2-(4-ethyl-3-oxo-1-oxa-4,9-diazaspiro[5.5]undecan-9-yl)acetamide

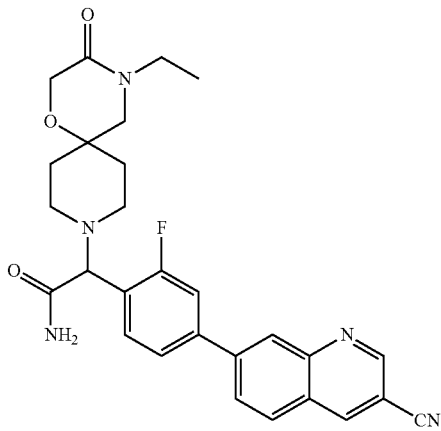 [SMILES: CCN1CC2(CCN(C(C(N)=O)c3ccc(-c4ccc5cc(C#N)cnc5c4)cc3F)CC2)OCC1=O]

a) To a solution of 2-(4-bromo-2-fluorophenyl)-2-(4-ethyl-3-oxo-1-oxa-4,9-diazaspiro[5.5]undecan-9-yl)acetamide (202 mg, 0.47 mmol), 4,4,4',4',5,5,5',5'-octamethyl-2,2'-bi(1,3,2-dioxaborolane) (120 mg, 0.47 mmol), and potassium acetate (93 mg, 0.94 mmol) in 1,4-dioxane (2.5 mL) was added PdCl₂(dppf)-CH₂Cl₂ adduct (38.5 mg, 0.05 mmol). The reaction mixture was purged with nitrogen and heated at 120° C. for 4 h. The reaction mixture was cooled and 7-bromoquinoline-3-carbonitrile (110 mg, 0.47 mmol) and 2M aq K₂CO₃ (0.52 mL, 1.04 mmol) were added. The reaction mixture was purged with nitrogen and heated with stirring at 100° C. for 1 h. The reaction mixture was diluted with dichloromethane (60 mL) and any salts were filtered away. The organic mixture was filtered through a plug of celite and sodium sulfate and the filtrate was treated with a small amount of Silicycle Si-thiol resin for 30 min. The mixture was filtered and concentrated in vacuo. Purification of the residue by reverse phase HPLC (10-70% acetonitrile:water with 0.1% NH₄OH) afforded the title product (138 mg, 55% yield). MS(ES)⁺ m/e 502 [M+H]⁺; ¹H NMR (400 MHz, CD₂Cl₂) δ ppm 1.13 (t, J=7.20 Hz, 3 H) 1.65-1.84 (m, 2 H) 1.86-2.04 (m, 2 H) 2.25-2.40 (m, 1 H) 2.55-2.74 (m, 2 H) 2.75-2.87 (m, 1 H) 3.18 (s, 2 H) 3.41 (q, J=7.07 Hz, 2 H) 3.92-4.11 (m, 2 H) 4.56 (s, 1 H) 5.62 (d, J=3.54 Hz, 1 H) 7.28 (d, J=4.29 Hz, 1 H) 7.49 (t, J=7.71 Hz, 1 H) 7.58 (dd, J=11.12, 1.77 Hz, 1 H) 7.65 (dd, J=8.08, 1.77 Hz, 1 H) 8.00 (dd, J=8.59, 1.77 Hz, 1 H) 8.06 (d, J=8.34 Hz, 1 H) 8.43 (s, 1 H) 8.63 (d, J=2.02 Hz, 1 H) 9.10 (d, J=2.02 Hz, 1 H).

Example 83

(+)-2-(4-(3-cyanoquinolin-7-yl)-2-fluorophenyl)-2-(4-ethyl-3-oxo-1-oxa-4,9-diazaspiro[5.5]undecan-9-yl)acetamide a) From Example 82a, the title product was isolated in 98.2% ee using chiral HPLC (ChiralPak IC, 40:60 isopropyl alcohol:acetonitrile) (37 mg, 27% yield). α_D=+49 deg (c=0.25, methanol); MS(ES)⁺ m/e 502 [M+H]⁺; ¹H NMR (400 MHz, CD₂Cl₂) δ ppm 1.13 (t, J=7.20 Hz, 3 H) 1.68-1.74 (m, 1 H) 1.75-1.80 (m, 1 H) 1.89-1.94 (m, 1 H) 1.96 (br. s., 1 H) 2.27-2.39 (m, 1 H) 2.58-2.70 (m, 2 H) 2.75-2.86 (m, 1 H) 3.18 (s, 2 H) 3.37-3.46 (m, 2 H) 4.01 (d, J=2.02 Hz, 2 H) 4.56 (s, 1 H) 5.95 (br. s., 1 H) 7.28 (br. s., 1 H) 7.49 (t, J=7.71 Hz, 1 H) 7.56 (d, J=2.02 Hz, 1 H) 7.64 (dd, J=7.83, 1.77 Hz, 1 H) 8.01 (d, J=1.77 Hz, 1 H) 8.03-8.08 (m, 1 H) 8.40-8.44 (m, 1 H) 8.63 (dd, J=2.15, 0.63 Hz, 1 H) 9.10 (d, J=2.02 Hz, 1 H).

Example 84

(−)-2-(4-(3-cyanoquinolin-7-yl)-2-fluorophenyl)-2-(4-ethyl-3-oxo-1-oxa-4,9-diazaspiro[5.5]undecan-9-yl)acetamide a) From Example 83a, the title product was also isolated in 98.8% ee using chiral HPLC (Chiralpak IC 40:60 isopropyl alcohol:acetonitrile) (33 mg, 24% yield). α_D=−35 deg (c=0.47, methanol); MS(ES)⁺ m/e 502 [M+H]⁺; ¹H NMR (400 MHz, CD₂Cl₂) δ ppm 1.13 (t, J=7.20 Hz, 3 H) 1.68-1.80 (m, 2 H) 1.90-1.94 (m, 1 H) 1.94-1.98 (m, 1 H) 2.33 (td, J=11.18, 2.15 Hz, 1 H) 2.58-2.70 (m, 2 H) 2.80-2.87 (m, 1 H) 3.18 (s, 2 H) 3.41 (q, J=7.07 Hz, 2 H) 4.01 (d, J=2.02 Hz, 2 H) 4.56 (s, 1 H) 5.70-5.78 (m, 1 H) 7.27 (br. s., 1 H) 7.49 (t, J=7.71 Hz, 1 H) 7.56 (d, J=1.77 Hz, 1 H) 7.65 (dd, J=8.08, 1.77 Hz, 1 H) 7.98-8.08 (m, 2 H) 8.37-8.44 (m, 1 H) 8.63 (dd, J=2.15, 0.63 Hz, 1 H) 9.10 (d, J=2.27 Hz, 1 H).

Example 85

2-(4-ethyl-3-oxo-1-oxa-4,9-diazaspiro[5.5]undecan-9-yl)-2-(2-fluoro-4-(3-methylquinolin-7-yl)phenyl)acetamide

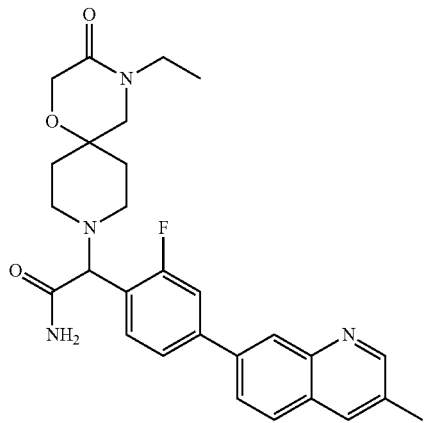 [SMILES: CCN1CC2(CCN(C(C(N)=O)c3ccc(-c4ccc5cc(C)cnc5c4)cc3F)CC2)OCC1=O]

a) To a solution of 2-(4-bromo-2-fluorophenyl)-2-(4-ethyl-3-oxo-1-oxa-4,9-diazaspiro[5.5]undecan-9-yl)acetamide (212 mg, 0.5 mmol), 4,4,4',4',5,5,5',5'-octamethyl-2,2'-bi(1,3,2-dioxaborolane) (126 mg, 0.5 mmol), and potassium acetate (97 mg, 0.99 mmol) in 1,4-dioxane (2.5 mL) was added PdCl₂(dppf)-CH₂Cl₂ adduct (40 mg, 0.05 mmol). The reaction mixture was purged with nitrogen and heated at 120° C. for 4 h. The reaction mixture was cooled and 7-bromo-3-methylquinoline (110 mg, 0.5 mmol) and 2M aq K₂CO₃ (0.55 mL, 1.09 mmol) were added. The reaction mixture was purged with nitrogen and was heated with stirring at 100° C. for 1 h. The reaction mixture was diluted with dichloromethane (60 mL) and any salts were filtered away. The organic mixture was filtered through a plug of celite and sodium sulfate. The filtrate was treated with a small amount of Silicycle Si-thiol resin for 30 min. The mixture was filtered and concentrated in vacuo. Purification of the residue by reverse phase HPLC (10-70% acetonitrile:water with 0.1% NH₄OH) provided the title product (131 mg, 51% yield). MS(ES)⁺ m/e 491 [M+H]⁺; ¹H NMR (400 MHz, CD₂Cl₂) δ ppm 1.12 (t, J=7.20 Hz, 3 H) 1.63-1.86 (m, 3 H) 1.86-2.05 (m, 2 H) 2.29-2.41 (m, 1 H) 2.53-2.59 (m, 3 H) 2.59-2.74 (m, 2 H) 2.79 (d, J=11.62 Hz, 1 H) 3.41 (q, J=7.33 Hz, 2 H) 3.95-4.10 (m, 2 H) 4.52 (s, 1 H) 5.87 (d, J=4.04 Hz, 1 H) 7.28 (d, J=3.54 Hz, 1 H) 7.41-7.50 (m, 1 H) 7.55 (dd, J=11.37, 1.77 Hz, 1 H) 7.62 (dd, J=7.96, 1.89 Hz, 1 H) 7.82 (dd, J=8.46, 1.89 Hz, 1 H) 7.90 (d, J=8.59 Hz, 1 H) 7.97-8.05 (m, 1 H) 8.27-8.36 (m, 1 H) 8.83 (d, J=2.27 Hz, 1 H).

Example 86

(−)-2-(4-ethyl-3-oxo-1-oxa-4,9-diazaspiro[5.5]undecan-9-yl)-2-(2-fluoro-4-(3-methylquinolin-7-yl)phenyl)acetamide a) From Example 85a, the title product was isolated in 99.9% ee using chiral HPLC (Lux Cell 4, methanol) (52 mg, 40% yield). α_D=−34 deg (c=0.06, methanol); MS(ES)⁺ m/e 491 [M+H]⁺; ¹H NMR (400 MHz, CD₂Cl₂) δ ppm 1.13 (t, J=7.20 Hz, 3 H) 1.68-1.74 (m, 2 H) 1.89-1.98 (m, 2 H) 2.29-2.40 (m, 1 H) 2.57 (s, 3 H) 2.59-2.70 (m, 2 H) 2.79 (dd, J=6.19, 3.92 Hz, 1 H) 3.19 (s, 2 H) 3.41 (q, J=7.33 Hz, 2 H) 4.02 (d, J=1.77 Hz, 2 H) 4.53 (s, 1 H) 5.61 (br. s., 1 H) 7.22-7.31 (m, 1 H) 7.42-7.50 (m, 1 H) 7.54 (d, J=1.77 Hz, 1 H) 7.62 (dd, J=7.83, 1.77 Hz, 1 H) 7.80-7.87 (m, 1 H) 7.90 (d, J=8.59 Hz, 1 H) 8.01 (d, J=0.76 Hz, 1 H) 8.31 (s, 1 H) 8.83 (d, J=2.27 Hz, 1 H).

Example 87

(+)-2-(4-ethyl-3-oxo-1-oxa-4,9-diazaspiro[5.5]undecan-9-yl)-2-(2-fluoro-4-(3-methylquinolin-7-yl)phenyl)acetamide a) From Example 86a, the title product was also isolated in 99.9% ee using chiral HPLC (Lux Cell 4, methanol) (51 mg, 39% yield). $\alpha_D$=+44 deg (c=0.07, methanol); MS(ES)$^+$ m/e 491 [M+H]$^+$; $^1$H NMR (400 MHz, CD$_2$Cl$_2$) δ ppm 1.13 (t, J=7.20 Hz, 3 H) 1.68-1.74 (m, 2 H) 1.89-1.98 (m, 2 H) 2.29-2.40 (m, 1 H) 2.57 (s, 3 H) 2.59-2.70 (m, 2 H) 2.79 (dd, J=6.19, 3.92 Hz, 1 H) 3.19 (s, 2 H) 3.41 (q, J=7.33 Hz, 2 H) 4.02 (d, J=1.77 Hz, 2 H) 4.53 (s, 1 H) 5.61 (br. s., 1 H) 7.22-7.31 (m, 1 H) 7.42-7.50 (m, 1 H) 7.54 (d, J=1.77 Hz, 1 H) 7.62 (dd, J=7.83, 1.77 Hz, 1 H) 7.80-7.87 (m, 1 H) 7.90 (d, J=8.59 Hz, 1 H) 8.01 (d, J=0.76 Hz, 1 H) 8.31 (s, 1 H) 8.83 (d, J=2.27 Hz, 1 H).

Example 88

(+)-2-(4-(3-chloroquinolin-7-yl)-2-fluorophenyl)-2-(4-ethyl-3-oxo-1-oxa-4,9-diazaspiro[5.5]undecan-9-yl)acetamide

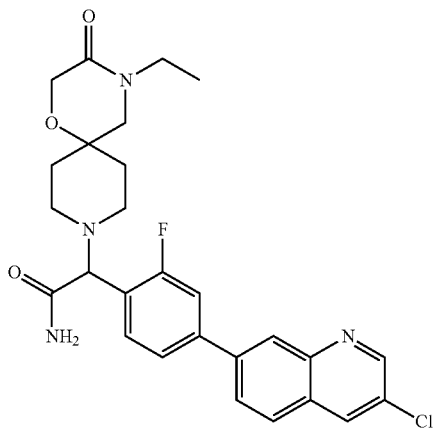 [SMILES: CCN1CC2(CCN(C(C(N)=O)c3ccc(-c4ccc5cc(Cl)cnc5c4)cc3F)CC2)OCC1=O]

a) A solution of 2-(4-bromo-2-fluorophenyl)-2-(4-ethyl-3-oxo-1-oxa-4,9-diazaspiro[5.5]undecan-9-yl)acetamide (200 mg, 0.35 mmol) in dry 1,4-dioxane (3 mL) in a 20 mL microwaveable vial was treated with bis(pinacolato)diboron (107 mg, 0.42 mmol), potassium acetate (49 mg, 0.5 mmol), and PdCl$_2$(dppf)-CH$_2$Cl$_2$ adduct (14.3 mg, 0.02 mmol). The solution was degassed with nitrogen for 3 min and the vessel was purged with nitrogen, sealed, and heated to 110° C. for 19 h. Analysis of a reaction mixture aliquot indicated the reaction had not proceeded to completion, so additional bis(pinacolato)diboron (267 mg, 1.05 mmol), potassium acetate (49 mg, 0.5 mmol) and PdCl$_2$(dppf)-CH$_2$Cl$_2$ adduct (35.8 mg, 0.044 mmol) were added and the reaction mixture was heated for 4 h. The reaction mixture was cooled and 7-bromo-3-chloroquinoline (85 mg, 0.35 mmol), PdCl$_2$(dppf)-CH$_2$Cl$_2$ adduct (14.3 mg, 0.02 mmol), and 2M aq potassium carbonate (0.525 mL, 1.05 mmol) were added. The reaction mixture was purged with nitrogen, sealed, and heated at 110° C. for 1 h. Analysis of a reaction mixture aliquot indicated the reaction had proceeded to completion. The reaction mixture was diluted with water (50 mL) and extracted with dichloromethane (3×100 mL). The combined organic layers was dried over anhydrous sodium sulfate, filtered, and concentrated under reduced pressure. The residue was dissolved in dichloromethane (5 mL) and treated with Silicycle Si-thiol with heating (40° C. sonicator for 30 sec). The mixture was filtered and the solution was concentrated under reduced pressure. Purification of the residue by reverse phase HPLC (10-90% actonitrile/water with 0.1% NH$_4$OH) afforded the racemix title product, which was resolved by chiral HPLC (ChiralPak IC, 40:60 isopropyl alcohol:acetonitrile) to provide the title product in 98.5% ee (20 mg, 11% yield). $\alpha_D$=+42 deg (c=0.12, methanol); MS(ES)$^+$ m/e 511 [M+H]$^+$; $^1$H NMR (400 MHz, CD$_2$Cl$_2$) δ ppm 1.12 (t, J=7.20 Hz, 3 H) 1.19 (d, J=6.06 Hz, 1 H) 1.59-1.84 (m, 1 H) 1.88-1.95 (m, 2 H) 2.29-2.40 (m, 1 H) 2.54-2.73 (m, 2 H) 2.73-2.84 (m, 1 H) 3.18 (s, 2 H) 3.41 (q, J=7.07 Hz, 2 H) 4.02 (d, J=2.02 Hz, 2 H) 4.53 (s, 1 H) 6.32 (br. s., 1 H) 7.30 (br. s., 1 H) 7.42-7.51 (m, 1 H) 7.55 (dd, J=11.37, 1.77 Hz) 7.61 (dd, J=8.08, 1.77 Hz, 1 H) 7.84-7.96 (m, 2 H) 8.24 (d, J=2.53 Hz, 1 H) 8.35 (s, 1 H) 8.88 (d, J=2.53 Hz, 1 H).

Example 89

(−)-2-(4-(3-chloroquinolin-7-yl)-2-fluorophenyl)-2-(4-ethyl-3-oxo-1-oxa-4,9-diazaspiro[5.5]undecan-9-yl)acetamide a) From Example 88a, the title product was also isolated in 99.3% ee using chiral HPLC (Chiralpak IC, 40:60 isopropyl alcohol:acetonitrile) (18 mg, 10% yield). $\alpha_D$=−40 deg (c=0.13, methanol); MS(ES)$^+$ m/e 511 [M+H]$^+$; $^1$H NMR (400 MHz, CD$_2$Cl$_2$) δ ppm 1.12 (t, J=7.20 Hz, 3 H) 1.62-1.82 (m, 2 H) 1.88-1.95 (m, 1 H) 2.27-2.40 (m, 1 H) 2.54-2.73 (m, 2 H) 2.73-2.85 (m, 1 H) 3.18 (s, 2 H) 3.41 (q, J=7.33 Hz, 2 H) 3.94-4.09 (m, 3 H) 4.53 (s, 1 H) 6.05 (br. s., 1 H) 7.29 (br. s., 1 H) 7.42-7.51 (m, 1 H) 7.55 (dd, J=11.37, 1.77 Hz, 1 H) 7.62 (dd, J=7.96, 1.89 Hz, 1 H) 7.86-7.99 (m, 2 H) 8.24 (d, J=2.27 Hz, 1 H) 8.30-8.39 (m, 1 H) 8.88 (d, J=2.27 Hz, 1 H).

Example 90

(+)-2-(4-ethyl-3-oxo-1-oxa-4,9-diazaspiro[5.5]undecan-9-yl)-2-(2-fluoro-4-(3-fluoroquinolin-7-yl)phenyl)acetamide

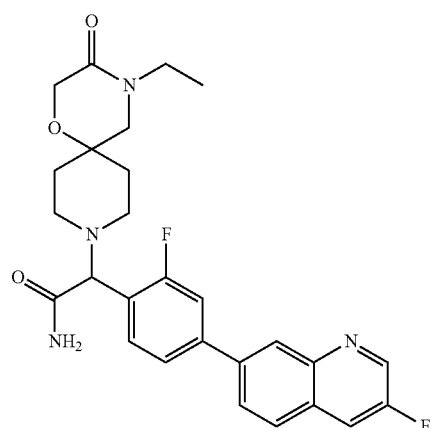

a) A solution of 2-(4-bromo-2-fluorophenyl)-2-(4-ethyl-3-oxo-1-oxa-4,9-diazaspiro[5.5]undecan-9-yl)acetamide (266 mg, 0.47 mmol) in dry 1,4-dioxane (3 mL) was treated with bis(pinacolato)diboron (142 mg, 0.56 mmol), potassium acetate (49 mg, 0.5 mmol) and PdCl$_2$(dppf)-CH$_2$Cl$_2$ adduct (19 mg, 0.023 mmol). The reaction mixture was degassed with nitrogen for ~3 min and the vessel was purged with nitrogen, sealed, and heated to 110° C. for 3 h. Analysis of a reaction mixture aliquot indicated complete conversion of the starting material to the boronate intermediate. To the cooled reaction mixture was added 7-bromo-3-fluoroquinoline (105 mg, 0.47 mmol), PdCl$_2$(dppf)-CH$_2$Cl$_2$ adduct (19 mg, 0.023 mmol) and 2M aq K$_2$CO$_3$ (0.7 mL, 1.4 mmol). The reaction mixture was purged with nitrogen, sealed, and heated at 120° C. for 1 h. The reaction mixture was diluted with water (50 mL) and extracted with dichloromethane (3×100 mL). The combined organic layers were dried over anhydrous sodium sulfate, filtered and concentrated under reduced pressure. Purification of the residue by reverse phase HPLC (5-75% acetonitrile:water with 0.1% NH$_4$OH) afforded the racemic title product, which was resolved by chiral HPLC (Lux Cell 4, methanol) to afford the title product in 95% ee (29 mg, 12% yield). α$_D$=+26 deg (c=0.14, methanol); MS(ES)$^+$ m/e 495 [M+H]$^+$; $^1$H NMR (400 MHz, CD$_2$Cl$_2$) δ ppm 1.06-1.18 (m, 3 H) 1.63-1.84 (m, 2 H) 1.90-1.97 (m, 2 H) 2.27-2.39 (m, 1 H) 2.53-2.73 (m, 2 H) 2.80 (d, J=11.37 Hz, 1 H) 3.18 (s, 2 H) 3.41 (q, J=7.07 Hz, 2 H) 3.95-4.08 (m, 2 H) 4.53 (s, 1 H) 6.28 (br. s., 1 H) 7.29 (br. s., 1 H) 7.47 (t, J=7.71 Hz, 1 H) 7.55 (dd, J=11.24, 1.89 Hz, 1 H) 7.62 (dd, J=7.96, 1.89 Hz, 1 H) 7.83-7.93 (m, 2 H) 7.93-8.00 (m, 1 H) 8.37 (d, J=1.77 Hz, 1 H) 8.88 (d, J=2.53 Hz, 1 H).

Example 91

(−)-2-(4-ethyl-3-oxo-1-oxa-4,9-diazaspiro[5.5]undecan-9-yl)-2-(2-fluoro-4-(3-fluoroquinolin-7-yl)phenyl)acetamide a) From Example 90a, the title product was also isolated in 99.2% ee using chiral HPLC (Lux Cell 4, methanol) (17 mg, 7% yield). α$_D$=−26 deg (c=0.12, methanol); MS(ES)$^+$ m/e 495 [M+H]$^+$; $^1$H NMR (400 MHz, CD$_2$Cl$_2$) δ ppm 1.06-1.18 (m, 3 H) 1.61-1.83 (m, 2 H) 1.87-1.96 (m, 2 H) 2.34 (td, J=11.12, 2.27 Hz, 1 H) 2.53-2.74 (m, 2 H) 2.74-2.85 (m, 1 H) 3.18 (s, 2 H) 3.41 (q, J=7.16 Hz, 2 H) 3.92-4.10 (m, 2 H) 4.53 (s, 1 H) 6.19 (d, J=3.28 Hz, 1 H) 7.29 (d, J=3.79 Hz, 1 H) 7.42-7.51 (m, 1 H) 7.55 (dd, J=11.24, 1.89 Hz, 1 H) 7.62 (dd, J=8.08, 1.77 Hz, 1 H) 7.83-7.92 (m, 2 H) 7.92-8.03 (m, 1 H) 8.37 (d, J=1.77 Hz, 1 H) 8.88 (d, J=2.53 Hz, 1 H).

Example 92

(+)-2-(4-ethyl-3-oxo-1-oxa-4,9-diazaspiro[5.5]undecan-9-yl)-2-(2-fluoro-4-(3-methoxyquinolin-7-yl)phenyl)acetamide

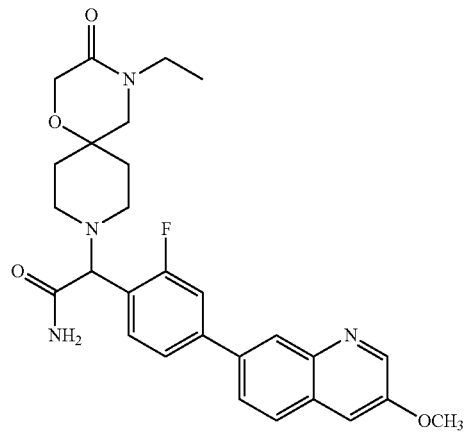 [SMILES: CCN1CC2(CCN(C(C(N)=O)c3ccc(-c4ccc5cc(OC)cnc5c4)cc3F)CC2)OCC1=O]

a) To a solution of 2-(4-bromo-2-fluorophenyl)-2-(4-ethyl-3-oxo-1-oxa-4,9-diazaspiro[5.5]undecan-9-yl)acetamide (198 mg, 0.46 mmol), 4,4,4',4',5,5,5',5'-octamethyl-2,2'-bi(1,3,2-dioxaborolane) (117 mg, 0.46 mmol), and potassium acetate (91 mg, 0.92 mmol) in 1,4-dioxane (2.5 mL) was added PdCl$_2$(dppf)-CH$_2$Cl$_2$ adduct (38 mg, 0.046 mmol). The reaction mixture was purged with nitrogen and heated at 120° C. for 4 h. The reaction mixture was cooled and 7-bromo-3-methoxyquinoline (110 mg, 0.46 mmol) and 2M aq K$_2$CO$_3$ (0.51 mL, 1.02 mmol) were added. The reaction mixture was purged with nitrogen and was heated with stirring at 100° C. for 1 h. The reaction mixture was diluted with dichloromethane (60 mL) and any salts were filtered away. The organic mixture was filtered through a plug of celite and sodium sulfate and the filtrate was treated with a small amount of Silicycle Si-thiol resin for 30 min. The mixture was filtered and concentrated in vacuo. Purification of the residue by reverse phase HPLC (10-70% acetonitrile:water with 0.1% NH$_4$OH) afforded the racemic title product, which was resolved by chiral HPLC (Chromegachiral CC4, methanol) to afford the title product in >98% ee (45 mg, 19% yield). α$_D$=+56° (c=0.02, methanol); MS(ES)$^+$ m/e 507 [M+H]$^+$; $^1$H NMR (400 MHz, CD$_2$Cl$_2$) δ ppm 1.12 (t, J=7.07 Hz, 3 H) 1.68-1.80 (m, 2 H) 1.90-2.02 (m, 2 H) 2.31-2.41 (m, 1 H) 2.58-2.71 (m, 2 H) 2.72-2.80 (m, 1 H) 3.18 (s, 2 H) 3.41 (d, J=7.33 Hz, 2 H) 4.01 (s, 3 H) 4.02 (d, J=1.77 Hz, 2 H) 4.52 (s, 1 H) 5.65 (d, J=4.55 Hz, 1 H) 7.21-7.33 (m, 1 H) 7.44-7.56 (m, 3 H) 7.61 (dd, J=7.96, 1.89 Hz, 1 H) 7.81-7.94 (m, 2 H) 8.30 (s, 1 H) 8.71 (d, J=3.03 Hz, 1 H).

Example 93

(−)-2-(4-ethyl-3-oxo-1-oxa-4,9-diazaspiro[5.5]undecan-9-yl)-2-(2-fluoro-4-(3-methoxyquinolin-7-yl)phenyl)acetamide a) From Example 92a, the title product was also isolated in >98% ee using chiral HPLC (Chromegachiral CC4, methanol) (49 mg, 21%). α$_D$=−53° (c=0.02, methanol); MS(ES)$^+$ m/e 507 [M+H]$^+$; $^1$H NMR (400 MHz, CD$_2$Cl$_2$) δ ppm 1.13 (t, J=7.20 Hz, 3 H) 1.68-1.80 (m, 2 H) 1.90-2.03 (m, 2 H)

2.31-2.43 (m, 1 H) 2.58-2.70 (m, 2 H) 2.75-2.80 (m, 1 H) 3.18 (s, 2 H) 3.41 (q, J=7.16 Hz, 2 H) 4.01 (s, 3 H) 4.02 (d, J=1.77 Hz, 2 H) 4.52 (s, 1 H) 5.65-5.72 (m, 1 H) 7.26-7.31 (m, 1 H) 7.44-7.57 (m, 3 H) 7.61 (dd, J=7.83, 1.77 Hz, 1 H) 7.81-7.93 (m, 2 H) 8.30 (s, 1 H) 8.71 (d, J=3.03 Hz, 1 H).

Biological Assays

FAS activity was measured through one of the two following assays.

Assay #1:

Inhibition of FAS activity can be measured based on the detection of residual NADPH substrate after the FAS assay is quenched. This assay is run as a 10 μL endpoint assay in 384-well format, where the reaction contains 20 μM malonyl-CoA, 2 μM acetyl-CoA, 30 μM NADPH and 40 nM FAS in 50 mM sodium phosphate, pH 7.0. The assay is run by sequentially dispensing 5 μl of a malonyl-CoA solution, then enzyme solution Containing the acetyl-CoA, and NADPH) into a black, low volume assay plate (Greiner 784076) pre-dispensed with 100 nL compound solutions in DMSO. The reaction is incubated at ambient temperature for 60 minutes, then quenched with 5 μL, of a developing solution composed of 90 μM resazurin, 0.3 IU/ml diaphorase in 50 mM sodium phosphate, pH 7.0. The developed reaction is read on a Molecular Devices Analyst or Acquest (or equivalent) plate reader using a 530 nm excitation wavelength filter, a 580 nm emission filter, and 561 nm dichroic filter. The test compounds are prepared in neat DMSO at a concentration of 10 mM. For inhibition curves, compounds are diluted using a three fold serial dilution and tested at 11 concentrations (e.g. 25 μM-0.42 nM). Curves are analysed using ActivityBase and XLfit, and results are expressed as pIC50 values.

Assay #2:

Inhibition of FAS can also be quantified based on the detection of the CoA products with a thio-reactive coumarin dye. This assay is run as a 100 μL endpoint assay in 384-well format, where the reaction contains 20 μM malonyl-CoA, 20 μM acetyl-CoA, 40 μM NADPH and 2 nM FAS in 50 mM sodium phosphate, pH 7.0, and 0.04% Tween-20. The assay is run by adding 50 μL enzyme solution to a black, low volume assay plate (Greiner 784076) pre-dispensed with 100 nl compound solutions in DMSO. After 30 minutes, 5 μL substrate is added, and the reaction incubated at ambient temperature for an additional 60 minutes. The reaction is then quenched with 100 μL of 6M guanidine-HCl containing 50 μM CPM (7-diethylamino-3-(4'-maleimidylphenyl)-4-methylcoumarin CPM; thio-reactive dye), and incubated for 30 minutes. The plate is read on an Envision (PerkinElmer) or equivalent plate reader using a 380 nm excitation wavelength filter, and a 486 nm emission filter. Data fitting and compound preparations are done as described above.

Biological Data

Exemplified compounds of the present invention (Examples 1-12) were tested according to the above assays and were found to be inhibitors of FAS. The $IC_{50}$ values ranged from about 1 to about 2,000 nM; the $IC_{50}$ values of the certain compounds ranged from about 1 to about 100 nM. The compounds described below were tested generally according to the assays described herein. The $IC_{50}$ for each compound was either reported in at least one experiment or the average of multiple experiments.

Example 6 is 501 nM
Example 9 is 3 nM
Example 13 is 50 nM
Example 22 is 20 nM
Example 30 is 3 nM
Example 33 is 200 nM
Example 73 is 1 nM
Example 78 is 4 nM Lipogenesis Assay Cultured primary human pre-adipocytes (Zen-Bio, Cat# ASC062801) are plated at confluence (3×104 cells/well) in 96-well plates (Costar, Cat#3598) coated with 0.2% gelatin (Sigma, Cat# G-6650) in DMEM/F12 medium (InvitroGen Cat#11330-032) supplemented with 10% heat inactivated fetal bovine serum (InvitroGen, Cat#16000-044). The following day (day 1) the cell differentiation is induced by replacing the seeding medium with the differentiation medium composed of DMEM/F12 medium supplemented with 10% heat inactivated fetal bovine serum, 200 μM 3-isobutyl-1-methylxanthine (Sigma, Cat# I-5879), 20 nM dexamethasone (Sigma, Cat# D-8893), 20 nM GW1929 (Sigma, Cat# G5668) and 20 nM insulin (InvitroGen, Cat#03-0110SA). On day 7, differentiation medium is replaced by the re-feed medium made of DMEM/F12 supplemented with 10% heat inactivated serum and 20 nM insulin. The appropriate concentration of tested compounds and controls are added into this medium at that time. On day 12, the relative amount of cellular triglyceride is estimated by using a Trinder kit (Sigma, Cat# TR0100). Re-feed medium is aspirated and cells are washed with PBS (InvitroGen, Cat#14190-144) and the assay is performed according the kit manufacturer protocol. Briefly, reconstituted solutions A and B are mixed with 0.01% digitonin (Sigma, Cat# D-5628) prior to performing the assay and added onto the cells; plates are incubated at 37° C. for one hour. The absorbance is read at 540 nm. The data is first normalized using the following equation: 100*((UNK−Control 1)/(Control 2−Control 1)) where Control 1 is the Robust Mean of the 0% response control and Control 2 is the Robust Mean of the 100% response control. When multiple dilutions of compounds are tested, pXC50 are calculated from curves using the 4-parameter curve fitting with the following equation: $y=(a-d)/(1+(s/c)\hat{}1))+d$ and with IRLS (Iterative Re-weighted Least Squares) algorithms to weight outliers (Mosteller, F. & Tukey J. W. (1977) Data Analysis and Regression, pp 353-365, Addison-Wesley).

The invention claimed is:
1. A compound according to Formula (I),

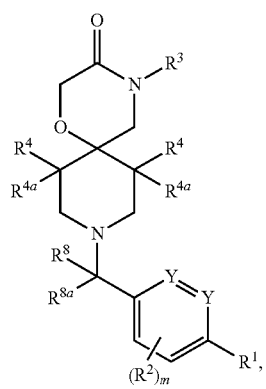

wherein
$R^1$ is phenyl, 5- or 6-membered heteroaryl, naphthyl, 9- or 10-membered heterocyclyl; wherein said phenyl, 5- or 6-membered heteroaryl, naphthyl, 9- or 10-membered heterocyclyl, is optionally substituted with from 1 to 3 substituents independently selected from the group consisting of: optionally substituted $C_1$-$C_6$alkyl; —$CF_3$, $C_3$-$C_7$cycloalkyl, —C(═O)$C_{14}$alkyl, —$C_1$-$C_6$alkyl$C_3$-$C_7$cycloalkyl, —C(═O)$C_3$-$C_7$cycloalkyl, —C(═O)

(phenyl), —C(=O)OC₁₄alkyl, —C(=O)OH, —C(=O)NR⁵R⁶, —O(C₂-C₄alkyl)NR⁵R⁶, phenyl, —SO₂C₁-C₄alkyl, —SO₂NR⁵R⁶, cyano, oxo, hydroxyl, halogen, C₁-C₄alkoxy, C₃-C₇cycloalkoxy, hydroxyC₁-C₄alkyl-, C₁-C₄alkoxyC₁-C₄alkyl-, —OCF₃, —NR⁵R⁶, R⁵R⁶NC₁-C₄alkyl-, —NR⁷C(=O)C₁-C₄alkyl, —NR⁷C(=O)NR⁵R⁶, —NR⁷SO₂C₁-C₄alkyl, —NR⁷SO₂NR⁵R⁶ and R⁹;

R⁵ is selected from the group consisting of hydrogen, C₁-C₄alkyl, C₃-C₇cycloalkyl, —C₁-C₃alkylC₃-C₇cycloalkyl, phenyl, and —C₁-C₃alkylphenyl;

R⁶ is hydrogen, C₁-C₄alkyl, C₃-C₇cycloalkyl, or —C₁-C₃alkylC₃-C₇cycloalkyl;

or R⁵ and R⁶ taken together with the nitrogen to which they are attached represent a 3-to 7-membered saturated ring optionally containing one other heteroatom which is oxygen, nitrogen, or sulfur, which is optionally substituted 1 or 2 times independently by oxo or C₁-C₄alkyl;

R⁷ is hydrogen or methyl;

R⁹ is a 5- or 6-membered heteroaryl ring containing 1 to 4 heteroatoms selected from oxygen, nitrogen, and sulfur, which is optionally substituted with 1 or 2 substituents selected from halogen, C₁-C₄alkyl, CF₃, C₁-C₄alkoxy, and —NR⁵R⁶;

each R² is selected from the group consisting of halogen, C₁-C₆alkyl, hydroxyl, and C₁-C₄alkoxy;

R³ is selected from the group consisting of: C₁-C₆alkyl, C₃-C₇cycloalkyl, hydroxyC₁-C₆alky-, and C₄-C₆heterocycloalkyl, wherein said C₁-C₆alkyl, C₃-C₇cycloalkyl, hydroxyC₁-C₆alky-, and C₄-C₆heterocycloalkyl is optionally substituted with from 1 to 4 substituents independently selected from the group consisting of: halogen, C₁-C₆alkyl, —CF₃, C₃-C₇cycloalkyl, —C(=O)C₁₄alkyl, —C(=O)C₃-C₇cycloalkyl, —C(=O)(phenyl), —C(=O)OH, —C(=O)OC₁-C₄alkyl, —C(=O)NR⁵R⁶, phenyl, —SO₂C₁-C₄alkyl, —SO₂NR⁵R⁶, cyano, oxo, hydroxyl, hydroxyC₁-C₄alky-, C₁-C₄alkoxy, C₃-C₇cycloalkoxy, C₁-C₄alkoxyC₁-C₄alkyl-, —OCF₃, —NR⁵R⁶, R⁵R⁶NC₁-C₄alkyl-, —NHC(O)C₁-C₄alkyl, —NHCONR⁵R⁶, —NHSO₂C₁-C₄alkyl, and —NHSO₂NR⁵R⁶;

each R⁴ and R⁴ᵃ is independently selected from hydrogen, halogen, C₁-C₆alkyl, hydroxyl, or C₁-C₆alkoxy;

wherein R⁸ and R⁸ᵃ are independently selected from hydrogen, deuterium, cyano, optionally substituted C₁-C₄alkyl,—C₁-C₄alkylhydroxy, C₁-C₆alkoxy, —C₁-C₄alkyl(=O)OH, —C₁-C₄alkyl(=O)OC₁-C₄alkyl, —C₁-C₄alkyl(=O)NR⁵R⁶, —C₁-C₄alkyl(=O)C₁-C₄alkyl, —C₁₄alkylSO₂C₁-C₄alkyl, —SO₂C₁-C₄alkyl, —C₁-C₄alkylSO₂NR⁵R⁶, —SO₂NR⁵R⁶, —C₁-C₄alkylNR⁵R⁶, —C₁-C₄alkylNR⁵SO₂C₁-C₄alkyl, —C₁-C₄alkylNR⁵SO₂NR⁵R⁶, —C₁-C₄alkylNR⁵C(=O)C₁-C₄alkyl, —C₁-C₄alkylNR⁵C(=O)NR⁵R⁶, C₁-C₄alkyl(=O)NR⁵OR⁶, triazolyl, and R⁹ wherein any C₁-C₄alkyl and C₁-C₆alkoxy moiety is optionally substituted with from 1 to 6 substituents independently selected from the group of: halogen, C₁-C₄alkyl, —CF₃, C₃-C₇cycloalkyl, —C(=O)C₁-C₄alkyl, —C(=O)C₃-C₇cycloalkyl, —C(=O)phenyl, —C₁-C₄alkylC(=O)OH, C(=O)OH, —C(=O)OC₁-C₄alkyl, —CONR⁵R⁶, phenyl, —SO₂C₁-C₄alkyl, —SO₂NR⁵R⁶, cyano, oxo, hydroxyl, C₁-C₄alkoxy, C₃-C₇cycloalkoxy, hydroxyC₁-C₄alkyl-, C₁-C₄alkoxyC₁-C₄alkyl-, —OCF₃, —NR⁵R⁶, R⁵R⁶NC₁-C₄alkyl-, —NR⁷C(O)C₁₄alkyl, —NR⁷CONR⁵R⁶, —NR⁷SO₂C₁-C₄alkyl, —NR⁷SO₂NR⁵R⁶, and R⁹, wherein when R⁸ is hydrogen R⁸ᵃ is not hydrogen or deuterium and wherein when R⁸ is deuterium R⁸ᵃ is not hydrogen or deuterium;

or R⁸ and R⁸ᵃ taken together with the carbon to which they are attached represent a 3- to 6-membered saturated ring optionally containing one or two heteroatoms selected from oxygen, nitrogen, and sulfur, which is optionally substituted 1 to 3 times by oxo, C₁-C₄alkyl, halogen, C₁-C₄alkylhydroxy, C₁-C₄alkoxy, or —NR⁵R⁶;

m is 0, 1, 2 or 3;

Y is C or N;

or a pharmaceutically acceptable salt thereof.

2. A compound of claim 1 according to Formula (I)(A),

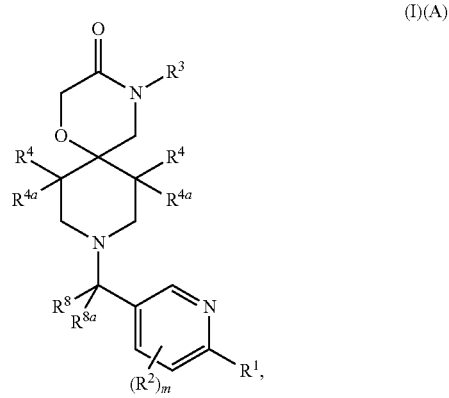

(I)(A)

wherein

R¹ is phenyl, 5- or 6-membered heteroaryl, naphthyl, 9- or 10-membered heterocyclyl; wherein said phenyl, 5- or 6-membered heteroaryl, naphthyl, 9- or 10-membered heterocyclyl, is optionally substituted with from 1 to 3 substituents independently selected from the group consisting of: optionally substituted C₁-C₆alkyl; —CF₃, C₃-C₇cycloalkyl, —C(=O)C₁₄alkyl, —C₁-C₆alkylC₃-C₇cycloalkyl, —C(=O)C₃-C₇cycloalkyl, —C(=O)(phenyl), —C(=O)OC₁₄alkyl, —C(=O)OH, —C(=O)NR⁵R⁶, —O(C₂-C₄alkyl)NR⁵R⁶, phenyl, —SO₂C₁-C₄alkyl, —SO₂NR⁵R⁶, cyano, oxo, hydroxyl, halogen, C₁-C₄alkoxy, hydroxyC₁-C₄alkyl-, C₁-C₄alkoxyC₁-C₄alkyl-, —OCF₃, —NR⁵R⁶, R⁵R⁶NC₁-C₄alkyl-, —NR⁷C(=O)C₁-C₄alkyl, —NR⁷C(=O)NR⁵R⁶, —NR⁷SO₂C₁-C₄alkyl, —NR⁷SO₂NR⁵R⁶ and R⁹;

R⁵ is selected from the group consisting of hydrogen, C₁-C₄alkyl, C₃-C₇cycloalkyl, —C₁-C₃alkylC₃-C₇cycloalkyl, phenyl, and —C₁-C₃alkylphenyl;

R⁶ is hydrogen, C₁-C₄alkyl, C₃-C₇cycloalkyl, or —C₁-C₃alkylC₃-C₇cycloalkyl;

or R⁵ and R⁶ taken together with the nitrogen to which they are attached represent a 3-to 7-membered saturated ring optionally containing one other heteroatom which is oxygen, nitrogen, or sulfur, which is optionally substituted 1 or 2 times independently by oxo or C₁-C₄alkyl;

R⁷ is hydrogen or methyl;

R⁹ is a 5- or 6-membered heteroaryl ring containing 1 to 4 heteroatoms selected from oxygen, nitrogen, and sulfur, which is optionally substituted with 1 or 2 substituents selected from halogen, C₁-C₄alkyl, CF₃, C₁-C₄alkoxy, and —NR⁵R⁶;

each R² is selected from the group consisting of halogen, C₁-C₆alkyl, hydroxyl, and C₁-C₄alkoxy;

R³ is selected from the group consisting of: C₁-C₆alkyl, C₃-C₇cycloalkyl, hydroxyC₁-C₆alky-, and a₄-C₆heterocycloalkyl, wherein said C₁-C₆alkyl, C₃-C₇cycloalkyl, hydroxyC₁-C₆alky-, and C₄-C₆heterocycloalkyl is optionally substituted with from 1 to 4 substituents independently selected from the group consisting of: halogen, $C_1$-$C_6$alkyl, —CF₃, $C_3$-$C_7$cycloalkyl, —C(═O)C₁-C₄alkyl, —C(═O)C₃-C₇cycloalkyl, —C(═O)(phenyl), —C(═O)OH, —C(═O)OC₁-C₄alkyl, —C(═O)NR⁵R⁶, phenyl, —SO₂C₁₄alkyl, —SO₂NR⁵R⁶, cyano, oxo, hydroxyl, $C_1$-$C_4$alkoxy, $C_3$-$C_7$cycloalkoxy, $C_1$-$C_4$alkoxyC₁-C₄alkyl-, —OCF₃, —NR⁵R⁶, R⁵R⁶NC₁₄alkyl-, —NHC(O)C₁₄alkyl, —NHCONR⁵R⁶, —NHSO₂C₁-C₄alkyl, and —NHSO₂NR⁵R⁶;

each R⁴ and R⁴ᵃ is independently selected from hydrogen, halogen, $C_1$-$C_6$alkyl, hydroxyl, or $C_1$-$C_6$alkoxy;

wherein R⁸ and R⁸ᵃ are independently selected from hydrogen, deuterium, cyano, optionally substituted C₁-C₄alkyl,—C₁-C₄alkylhydroxy, C₁-C₆alkoxy, —C₁-C₄alkyl(═O)OH, —C₁-C₄alkyl(═O)OC₁₀-C₄alkyl, —C₁-C₄alkyl(═O)NR⁵R⁶, —C₁-C₄alkyl(═O)C₁-C₄alkyl, —C₁-C₄alkylSO₂C₁-C₄alkyl, —SO₂C₁-C₄alkyl, —C₁-C₄alkylSO₂NR⁵R⁶, —SO₂NR⁵R⁶, —C₁-C₄alkylNR⁵R⁶, —C₁-C₄alkylNR⁵SO₂C₁-C₄alkyl, —C₁-C₄alkylNR⁵SO₂NR⁵R⁶, —C₁-C₄alkylNR⁵C(═O)C₁-C₄alkyl, —C₁-C₄alkylNR⁵C(═O)NR⁵R⁶, C₁-C₄alkyl(═O)NR⁵OR⁶, triazolyl, and R⁹ wherein any C₁C₄alkyl and C₁-C₆alkoxy moiety is optionally substituted with from 1 to 6 substituents independently selected from the group of: halogen, C₁-C₄alkyl, —CF₃, C₃-C₇cycloalkyl, —C(═O)C₁-C₄alkyl, —C(═O)C₃-C₇cycloalkyl, —C(═O)phenyl, —C₁-C₄alkyl(═O)OH, —C(═O)OC₁-C₄alkyl, —CONR⁵R⁶, phenyl, —SO₂C₁-C₄alkyl, —SO₂NR⁵R⁶, cyano, oxo, hydroxyl, C₁-C₄alkoxy, C₃-C₇cycloalkoxy, hydroxyC₁-C₄alkyl-, C₁-C₄alkoxyC₁-C₄alkyl-, —OCF₃, —NR⁵R⁶, R⁵R⁶NC₁-C₄alkyl-, —NR⁷C(O)C₁₄alkyl-, —NR⁷CONR⁵R⁶, —NR⁷SO₂C₁-C₄alkyl, —NR⁷SO₂NR⁵R⁶, triazolyl, and R⁹, wherein when R⁸ is hydrogen R⁸ᵃ is not hydrogen or deuterium and wherein when R⁸ is deuterium R⁸ᵃ is not hydrogen or deuterium;

or R⁸ and R⁸ᵃ taken together with the carbon to which they are attached represent a 3- to 6-membered saturated ring optionally containing one or two heteroatoms selected from oxygen, nitrogen, and sulfur, which is optionally substituted 1 to 3 times by oxo, C₁-C₄alkyl, halogen, C₁-C₄alkylhydroxy, C₁-C₄alkoxy, or —NR⁵R⁶;

m is 0, 1, 2 or 3;

or a pharmaceutically acceptable salt thereof.

3. A compound of claim 1 according to Formula (I)(B), (I)(B)

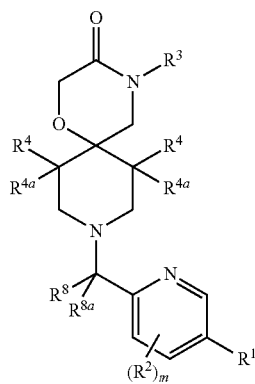

wherein

R¹ is phenyl, 5- or 6-membered heteroaryl, naphthyl, 9- or 10-membered heterocyclyl; wherein said phenyl, 5- or 6-membered heteroaryl, naphthyl, 9- or 10-membered heterocyclyl, is optionally substituted with from 1 to 3 substituents independently selected from the group consisting of: optionally substituted C₁-C₆alkyl; —CF₃, C₃-C₇cycloalkyl, —C(═O)C₁₄alkyl, —C₁-C₆alkylC₃-C₇cycloalkyl, —C(═O)C₃-C₇cycloalkyl, —C(═O)(phenyl), —C(═O)OC₁₄alkyl, —C(═O)OH, —C(═O)NR⁵R⁶, —O(C₂-C₄alkyl)NR⁵R⁶, phenyl, —SO₂C₁-C₄alkyl, —SO₂NR⁵R⁶, cyano, oxo, hydroxyl, halogen, C₁-C₄alkoxy, hydroxyC₁-C₄alkyl-, —OCF₃, —NR⁵R⁶, R⁵R⁶NC₁₄alkyl-, —NR⁷C(═O)C₁-C₄alkyl, —NR⁷C(═O)NR⁵R⁶, —NR⁷SO₂C₁-C₄alkyl, —NR⁷SO₂NR⁵R⁶ and R⁹;

R⁵ is selected from the group consisting of hydrogen, C₁-C₄alkyl, C₃-C₇cycloalkyl, —C₁-C₃alkylC₃-C₇cycloalkyl, phenyl, and —C₁-C₃alkylphenyl;

R⁶ is hydrogen, C₁-C₄alkyl, C₃-C₇cycloalkyl, or —C₁-C₃alkylC₃-C₇cycloalkyl;

or R⁵ and R⁶ taken together with the nitrogen to which they are attached represent a 3-to 7-membered saturated ring optionally containing one other heteroatom which is oxygen, nitrogen, or sulfur, which is optionally substituted 1 or 2 times independently by oxo or C₁-C₄alkyl;

R⁷ is hydrogen or methyl;

R⁹ is a 5- or 6-membered heteroaryl ring containing 1 to 4 heteroatoms selected from oxygen, nitrogen, and sulfur, which is optionally substituted with 1 or 2 substituents selected from halogen, C₁-C₄alkyl, CF₃, C₁-C₄alkoxy, and —NR⁵R⁶;

each R² is selected from the group consisting of halogen, C₁-C₆alkyl, hydroxyl, and C₁-C₄alkoxy;

R³ is selected from the group consisting of: C₁-C₆alkyl, C₃-C₇cycloalkyl, hydroxyC₁-C₆alky-, and C₄-C₆heterocycloalkyl, wherein said C₁-C₆alkyl, C₃-C₇cycloalkyl, hydroxyC₁-C₆alky-, and C₄-C₆heterocycloalkyl is optionally substituted with from 1 to 4 substituents independently selected from the group consisting of: halogen, C₁-C₆alkyl, —CF₃, C₃-C₇cycloalkyl, —C(═O)C₁₄alkyl, —C(═O)C₃-C₇cycloalkyl, —C(═O)(phenyl), —C(═O)OH, —C(═O)OC₁₄alkyl, —C(═O)NR⁵R⁶, phenyl, —SO₂C₁-C₄alkyl, —SO₂NR⁵R⁶, cyano, oxo, hydroxyl, C₁-C₄alkoxy, C₃-C₇cycloalkoxy, C₁-C₄alkoxyC₁-C₄alkyl-, —OCF₃, —NR⁵R⁶, R⁶R⁶NC₁₄alkyl-, —NHC(O)C₁₄alkyl, —NHCONR⁵R⁶, —NHSO₂C₁₄alkyl, and —NHSO₂NR⁵R⁶;

each R⁴ and R⁴ᵃ is independently selected from hydrogen, halogen, C₁-C₆alkyl, hydroxyl, or C₁-C₆alkoxy;

wherein R⁸ and R⁸ᵃ are independently selected from hydrogen, deuterium, cyano, optionally substituted C₁-C₄alkyl,—C₁-C₄alkylhydroxy, C₁-C₆alkoxy, —C₁-C₄alkyl(═O)OH, —C₁-C₄alkyl(═O)OC₁-C₄alkyl, —C₁-C₄alkyl(═O)NR⁵R⁶, —C₁-C₄alkyl(═O)C₁-C₄alkyl, —C₁-C₄alkylSO₂C₁-C₄alkyl, —SO₂C₁-C₄alkyl, —C₁-C₄alkylSO₂NR⁵R⁶, —SO₂NR⁵R⁶, —C₁-C₄alkylNR⁵R⁶, —C₁-C₄alkylNR⁵SO₂C₁-C₄alkyl, —C₁-C₄alkylNR⁵SO₂NR⁵R⁶, —C₁-C₄alkylNR⁵C(═O)C₁-C₄alkyl, —C₁-C₄alkylNR⁵C(═O)NR⁵R⁶, C₁-C₄alkyl(═O)NR⁵OR⁶, triazolyl, and R⁹ wherein any C₁C₄alkyl and C₁-C₆alkoxy moiety is optionally substituted with from 1 to 6 substituents independently selected from the group of: halogen, $C_1$-$C_4$alkyl, —$CF_3$, $C_3$-$C_7$cycloalkyl, —C(═O)$C_{14}$alkyl, —C(═O)$C_3$-$C_7$cycloalkyl, —C(═O)phenyl, —$C_1$-$C_4$alkyl(═O)OH, —C(═O)O$C_1$-$C_4$alkyl, —CONR$^5$R$^6$, phenyl, —SO$_2$$C_1$-$C_4$alkyl, —SO$_2$NR$^5$R$^6$, cyano, oxo, hydroxyl, $C_1$-$C_4$alkoxy, $C_3$-$C_7$cycloalkoxy, hydroxy$C_1$-$C_4$alkyl-, $C_1$-$C_4$alkoxy$C_1$-$C_4$alkyl-, —OCF$_3$, —NR$^5$R$^6$, R$^5$R$^6$N$C_1$-$C_4$alkyl-, —NR$^7$C(O)$C_1$-$C_4$alkyl, —NR$^7$CONR$^5$R$^6$, —NR$^7$SO$_2$$C_1$-$C_4$alkyl, —NR$^7$SO$_2$NR$^5$R$^6$, triazolyl, and R$^9$, wherein when when R$^8$ is hydrogen R$^{8a}$ is not hydrogen or deuterium and wherein when R$^8$ is deuterium R$^{8a}$ is not hydrogen or deuterium;

or R$^8$ and R$^{8a}$ taken together with the carbon to which they are attached represent a 3- to 6-membered saturated ring optionally containing one or two heteroatoms selected from oxygen, nitrogen, and sulfur, which is optionally substituted 1 to 3 times by oxo, $C_1$-$C_4$alkyl, halogen, $C_1$-$C_4$alkylhydroxy, $C_1$-$C_4$alkoxy, or —NR$^5$R$^6$;

m is 0, 1, 2 or 3;

or a pharmaceutically acceptable salt thereof.

4. A compound of claim 1 according to Formula (I)(C),

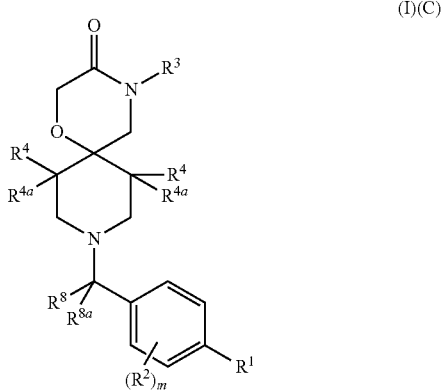

(I)(C)

wherein

R$^1$ is phenyl, 5- or 6-membered heteroaryl, naphthyl, 9- or 10-membered heterocyclyl; wherein said phenyl, 5- or 6-membered heteroaryl, naphthyl, 9- or 10-membered heterocyclyl, is optionally substituted with from 1 to 3 substituents independently selected from the group consisting of: optionally substituted $C_1$-$C_6$alkyl; —CF$_3$, $C_3$-$C_7$cycloalkyl, —C(═O)$C_1$-$C_4$alkyl, —$C_1$-$C_6$alkyl$C_3$-$C_7$cycloalkyl, —C(═O)$C_3$-$C_7$cycloalkyl, —C(═O)(phenyl), —C(═O)O$C_1$-$C_4$alkyl, —C(═O)OH, —C(═O)NR$^5$R$^6$, —O($C_2$-$C_4$alkyl)NR$^5$R$^6$, phenyl, —SO$_2$$C_1$-$C_4$alkyl, —SO$_2$NR$^5$R$^6$, cyano, oxo, hydroxyl, halogen, $C_1$-$C_4$alkoxy, hydroxy$C_1$-$C_4$alkyl-, —OCF$_3$, —NR$^5$R$^6$, R$^5$R$^6$N$C_1$-$C_4$alkyl-, —NR$^7$C(═O)$C_1$-$C_4$alkyl, —NR$^7$C(═O)NR$^5$R$^6$, —NR$^7$SO$_2$$C_1$-$C_4$alkyl, —NR$^7$SO$_2$NR$^5$R$^6$ and R$^9$;

R$^5$ is selected from the group consisting of hydrogen, $C_1$-$C_4$alkyl, $C_3$-$C_7$cycloalkyl, —$C_1$-$C_3$alkyl$C_3$-$C_7$cycloalkyl, phenyl, and —$C_1$-$C_3$alkylphenyl;

R$^6$ is hydrogen, $C_1$-$C_4$alkyl, $C_3$-$C_7$cycloalkyl, or —$C_1$-$C_3$alkyl$C_3$-$C_7$cycloalkyl;

or R$^5$ and R$^6$ taken together with the nitrogen to which they are attached represent a 3-to 7-membered saturated ring optionally containing one other heteroatom which is oxygen, nitrogen, or sulfur, which is optionally substituted 1 or 2 times independently by oxo or $C_1$-$C_4$alkyl;

R$^7$ is hydrogen or methyl;

R$^9$ is a 5- or 6-membered heteroaryl ring containing 1 to 4 heteroatoms selected from oxygen, nitrogen, and sulfur, which is optionally substituted with 1 or 2 substituents selected from halogen, $C_1$-$C_4$alkyl, CF$_3$, $C_1$-$C_4$alkoxy, and —NR$^5$R$^6$;

each R$^2$ is selected from the group consisting of halogen, $C_1$-$C_6$alkyl, hydroxyl, and $C_1$-$C_4$alkoxy;

R$^3$ is selected from the group consisting of: $C_1$-$C_6$alkyl, $C_3$-$C_7$cycloalkyl, hydroxy$C_1$-$C_6$alky-, and $C_4$-$C_6$heterocycloalkyl, wherein said $C_1$-$C_6$alkyl, $C_3$-$C_7$cycloalkyl, hydroxy$C_1$-$C_6$alky-, and $C_4$-$C_6$heterocycloalkyl is optionally substituted with from 1 to 4 substituents independently selected from the group consisting of: halogen, $C_1$-$C_6$alkyl, —CF$_3$, $C_3$-$C_7$cycloalkyl, —C(═O)$C_1$-$C_4$alkyl, —C(═O)$C_3$-$C_7$cycloalkyl, —C(═O)(phenyl), —C(═O)OH, —C(═O)O$C_1$-$C_4$alkyl, —C(═O)NR$^5$R$^6$, phenyl, —SO$_2$$C_1$-$C_4$alkyl, —SO$_2$NR$^5$R$^6$, cyano, oxo, hydroxyl, $C_1$-$C_4$alkoxy, $C_3$-$C_7$cycloalkoxy, $C_1$-$C_4$alkoxy$C_1$-$C_4$alkyl-, —OCF$_3$, —NR$^5$R$^6$, R$^5$R$^6$N$C_1$-$C_4$alkyl-, —NHC(O)$C_1$-$C_4$alkyl, —NHCONR$^5$R$^6$, —NHSO$_2$$C_1$-$C_4$alkyl, and —NHSO$_2$NR$^5$R$^6$;

each R$^4$ and R$^{4a}$ is independently selected from hydrogen, halogen, $C_1$-$C_6$alkyl, hydroxyl, or $C_1$-$C_6$alkoxy;

wherein R$^8$ and R$^{8a}$ are independently selected from hydrogen, deuterium, cyano, optionally substituted $C_1$-$C_4$alkyl,—$C_1$-$C_4$alkylhydroxy, $C_1$-$C_6$alkoxy, —$C_1$-$C_4$alkyl(═O)OH, —$C_1$-$C_4$alkyl(═O)O$C_1$-$C_4$alkyl, —$C_1$-$C_4$alkyl(═O)NR$^5$R$^6$, —$C_1$-$C_4$alkyl(═O)$C_1$-$C_4$alkyl, —$C_1$-$C_4$alkylSO$_2$$C_1$-$C_4$alkyl, —SO$_2$$C_1$-$C_4$alkyl, —$C_1$-$C_4$alkylSO$_2$NR$^5$R$^6$, —SO$_2$NR$^5$R$^6$, —$C_1$-$C_4$alkylNR$^5$R$^6$, —$C_1$-$C_4$alkylNR$^5$SO$_2$$C_1$-$C_4$alkyl, —$C_1$-$C_4$alkylNR$^5$SO$_2$NR$^5$R$^6$, —$C_1$-$C_4$alkylNR$^5$C(═O)$C_1$-$C_4$alkyl, —$C_1$-$C_4$alkylNR$^5$C(═O)NR$^5$R$^6$, $C_1$-$C_4$alkyl(═O)NR$^5$OR$^6$, triazolyl, and R$^9$ wherein any $C_1$-$C_4$alkyl and $C_1$-$C_6$alkoxy moiety is optionally substituted with from 1 to 6 substituents independently selected from the group of: halogen, $C_1$-$C_4$alkyl, —CF$_3$, $C_3$-$C_7$cycloalkyl, —C(═O)$C_1$-$C_4$alkyl, —C(═O)$C_3$-$C_7$cycloalkyl, —C(═O)phenyl, —$C_1$-$C_4$alkyl(═O)OH, —C(═O)O$C_1$-$C_4$alkyl, —CONR$^5$R$^6$, phenyl, —SO$_2$$C_1$-$C_4$alkyl, —SO$_2$NR$^5$R$^6$, cyano, oxo, hydroxyl, $C_1$-$C_4$alkoxy, $C_3$-$C_7$cycloalkoxy, hydroxy$C_1$-$C_4$alkyl-, $C_1$-$C_4$alkoxy$C_1$-$C_4$alkyl-, —OCF$_3$, —NR$^5$R$^6$, R$^5$R$^6$N$C_1$-$C_4$alkyl-, —NR$^7$C(O)$C_1$-$C_4$alkyl, —NR$^7$CONR$^5$R$^6$, —NR$^7$SO$_2$$C_1$-$C_4$alkyl, —NR$^7$SO$_2$NR$^5$R$^6$, triazolyl, and R$^9$, wherein when R$^8$ is hydrogen R$^{8a}$ is not hydrogen or deuterium and wherein when R$^8$ is deuterium R$^{8a}$ is not hydrogen or deuterium;

or R$^8$ and R$^{8a}$ taken together with the carbon to which they are attached represent a 3- to 6-membered saturated ring optionally containing one or two heteroatoms selected from oxygen, nitrogen, and sulfur, which is optionally substituted 1 to 3 times by oxo, $C_1$-$C_4$alkyl, halogen, $C_1$C-$_4$alkylhydroxy, $C_1$-$C_4$alkoxy, or —NR$^5$R$^6$;

m is 0, 1, 2 or 3;

or a pharmaceutically acceptable salt thereof.

5. A compound of claim 1 according to Formula (I)(D),

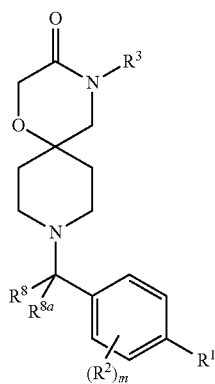

(I)(D)

wherein
R¹ is phenyl, naphthyl, quinolyl, isoquinolyl, wherein said phenyl, naphthyl, quinolyl isoquinolyl, is optionally substituted with from 1 to 3 substituents independently selected from: optionally substituted $C_1$-$C_6$alkyl; —$CF_3$, $C_3$-$C_7$cycloalkyl, -cyano, oxo, hydroxyl, halogen, $C_1$-$C_4$alkoxy, hydroxy$C_1$-$C_4$alkyl-, $C_1$-$C_4$alkoxy$C_1$-$C_4$alkyl-, and —$OCF_3$;

each $R^2$ is selected from the group consisting of halogen, $C_1$-$C_6$alkyl, hydroxyl, cyano, and $C_1$-$C_4$alkoxy;

$R^3$ is selected from the group consisting of: $C_1$-$C_6$alkyl and $C_3$-$C_7$cycloalkyl, wherein $R^8$ and $R^{8a}$ are independently selected from hydrogen, deuterium, cyano, $C_1$-$C_4$alkyl, —$C_1$-$C_4$alkylhydroxy, $C_1$-$C_6$alkoxy, —$C_1$-$C_4$alkyl(═O)OH, —$C_{14}$alkyl(═O)O$C_1$-$C_4$alkyl, —$C_1$-$C_4$alkyl(═O)NR$^5$R$^6$, —$C_1$-$C_4$alkylNR$^5$R$^6$, —$C_1$-$C_4$alkylNR$^5$C(═O)$C_1$-$C_4$alkyl, —$C_1$-$C_4$alkylNR$^5$C(═O)NR$^5$R$^6$, $C_1$-$C_4$alkyl(═O)NR$^5$OR$^6$, and triazolyl wherein when when $R^8$ is hydrogen $R^{8a}$ is not hydrogen or deuterium and wherein when $R^8$ is deuterium $R^{8a}$ is not hydrogen or deuterium;

$R^5$ is selected from the group consisting of hydrogen and $C_1$-$C_4$alkyl;

$R^6$ is hydrogen and $C_1$-$C_4$alkyl, m is 0, 1, 2 or 3;

or a pharmaceutically acceptable salt thereof.

6. A compound or pharmaceutically acceptable salt according to claim 1, wherein R¹ is phenyl optionally substituted with from 1 to 3 substituents independently selected from: optionally substituted $C_1$-$C_6$alkyl; —$CF_3$, $C_3$-$C_7$cycloalkyl, —C(═O)$C_1$-$C_4$alkyl, —$C_1$-$C_6$alkyl$C_3$-$C_7$cycloalkyl, —C(═O)$C_3$-$C_7$cycloalkyl, —C(═O)(phenyl), —C(═O)O$C_1$-$C_4$alkyl, —C(═O)OH, —C(═O)NR$^5$R$^6$, —O($C_1$-$C_4$alkyl)NR$^5$R$^6$, phenyl, —$SO_2C_1$-$C_4$alkyl, —$SO_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —$OCF_3$, —NR$^5$R$^6$, R$^5$R$^6$NC$_1$-$C_4$alkyl-, —NR$^7$C(═O)$C_1$-$C_4$alkyl, —NR$^7$C(═O)NR$^5$R$^6$, —NR$^7$SO$_2$$C_1$-$C_4$alkyl, —N R$^7$SO$_2$NR$^5$R$^6$ and R$^9$.

7. A compound or pharmaceutically acceptable salt according to claim 1, wherein R¹ is selected from furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, or triazinyl, wherein said furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, and triazinyl all of which are optionally substituted with from 1 to 3 substituents independently selected from: optionally substituted $C_1$-$C_6$alkyl; —$CF_3$, $C_3$-$C_7$cycloalkyl, —C(═O)$C_1$-$C_4$alkyl, —$C_1$-$C_6$alkyl$C_3$-$C_7$cycloalkyl, —C(═O)$C_3$-$C_7$cycloalkyl, —C(═O)(phenyl), —C(═O)O$C_{14}$alkyl, —C(═O)OH, —C(═O)NR$^5$R$^6$, —O($C_1$-$C_4$alkyl)NR$^5$R$^6$, phenyl, —$SO_2C_1$-$C_4$alkyl, —$SO_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —$OCF_3$, —NR$^5$R$^6$, R$^5$R$^6$NC$_1$-$C_4$alkyl-, —NR$^7$C(═O)$C_1$-$C_4$alkyl, —NR$^7$C(═O)NR$^5$R$^6$, —NR$^7$SO$_2$$C_1$-$C_4$alkyl, —NR$^7$SO$_2$NR$^5$R$^6$ and R9.

8. A compound or pharmaceutically acceptable salt according to claim 1, wherein R¹ is naphthyl optionally substituted with from 1 to 3 substituents independently selected from: optionally substituted $C_1$-$C_6$alkyl; —$CF_3$, $C_3$-$C_7$cycloalkyl, —C(═O)$C_1$-$C_4$alkyl, —$C_1$-$C_6$alkyl$C_3$-$C_7$cycloalkyl, —C(═O)$C_3$-$C_7$cycloalkyl, —C(═O)(phenyl), —C(═O)O$C_1$-$C_4$alkyl, —C(═O)OH, —C(═O)NR$^5$R$^6$, —O($C_1$-$C_4$alkyl)NR$^5$R$^6$, phenyl, —$SO_2C_1$-$C_4$alkyl, —$SO_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —$OCF_3$, —NR$^5$R$^6$, R$^5$R$^6$NC$_1$-$C_4$alkyl-, —NR$^7$C(═O)$C_1$-$C_4$alkyl, —NR$^7$C(═O)NR$^5$R$^6$, —NR$^7$SO$_2$$C_1$-$C_4$alkyl, —NR$^7$SO$_2$NR$^5$R$^6$ and $R^9$.

9. A compound or pharmaceutically acceptable salt according to claim 1, wherein R¹ is selected from benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, 1-H-indazolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, or pteridinyl, wherein said benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, 1-H-indazolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl all of which are optionally substituted with from 1 to 3 substituents independently selected from optionally substituted $C_1$-$C_6$alkyl; —$CF_3$, $C_3$-$C_7$cycloalkyl, —C(═O)$C_1$-$C_4$alkyl, —$C_1$-$C_6$alkyl$C_3$-$C_7$cycloalkyl, —C(═O)$C_3$-$C_7$cycloalkyl, —C(═O)(phenyl), —C(═O)O$C_1$-$C_4$alkyl, —C(═O)OH, —C(═O)NR$^5$R$^6$, —O($C_1$-$C_4$alkyl)NR$^5$R$^6$, phenyl, —$SO_2C_1$-$C_4$alkyl, —$SO_2$NR$^5$R$^6$, cyano, oxo, hydroxyl, halogen, $C_1$-$C_4$alkoxy, $C_3$-$C_7$cycloalkyl$C_1$-$C_4$alkoxy, hydroxy$C_1$-$C_4$alkyl-, $C_1$-$C_4$alkoxy$C_1$-$C_4$alkyl-, —$OCF_3$, —NR$^5$R$^6$, R$^5$R$^6$NC$_1$-$C_4$alkyl-, —NR$^7$C(═O)$C_1$-$C_4$alkyl, —NR$^7$C(═O)NR$^5$R$^6$, —NR$^7$SO$_2$$C_1$-$C_4$alkyl, —NR$^7$SO$_2$NR$^5$R$^6$ and $R^9$.

10. A compound or pharmaceutically acceptable salt according to claim 1, wherein $R^1$ is selected from phenyl and optionally substituted quinolinyl.

11. A compound or pharmaceutically acceptable salt according to claim 1, wherein $R^2$ is absent or is fluoro, hydroxyl, methyl, or methoxy.

12. A compound or pharmaceutically acceptable salt according to claim 1, wherein $R^3$ is selected from ethyl, isopropyl, 1-methylcyclopropyl, 1hydroxymethylcyclopropyl, and cyclopropyl.

13. A compound or pharmaceutically acceptable salt according claim 1, wherein:
   $R^1$ is selected from the group of: phenyl, indolyl, benzofuranyl, indazolyl, benzoimidazolinyl, naphthalyl, quinolyl, and wherein said phenyl, indolyl, benzofuranyl, indazolyl, benzoimidazolinyl, naphthalyl, quinolyl is optionally substituted with from 1 to 3 substituents independently selected from: $C_1$-$C_4$, methyloxy, cyano, $NR^5R^6$ and halogen,
   each $R^2$ is selected from the group consisting of halogen, $C_1$-$C_6$alkyl, hydroxyl, and $C_1$-$C_4$alkoxy;
   $R^3$ is selected from the group consisting of $C_1$-$C_6$alkyl and cyclopropyl; and
   each $R^4$ and $R^{4a}$ is independently selected from hydrogen, oxo, halogen or $C_1$-$C_6$alkyl;
   each $R^8$ and $R^{8a}$ is independently selected from hydrogen, deuterium, cyano, optionally substituted $C_1$-$C_4$alkyl, —$C_1$-$C_4$hydroxy, $C_1$-$C_6$alkoxy —$C_1$-$C_4$(=O)OH, —$C_1$-$C_4$(=O)OC_1$-$C_4$, —$C_1$-$C_4$(=O)NR^5R^6$, —$C_1$-$C_4NR^5R^6$, triazolyl, and $R^9$ wherein any optionally substituted $C_1$-$C_4$alkyl and $C_1$-$C_6$alkoxy moiety is optionally substituted with from 1 to 4 substituents independently selected from the group of: halogen, $C_1$-$C_4$alkyl, —$CF_3$, $C_3$-$C_7$cycloalkyl, —C(=O)C_1$-$C_4$alkyl, —C(=O)C_3$-$C_7$cycloalkyl, —C(=O)phenyl, carboxyl, —C(=O)OC_1$-$C_4$alkyl, —$CONR^5R^6$, phenyl, 5- or 6-membered heteroaryl, —$SO_2C_1$-$C_4$alkyl, —$SO_2NR^5R^6$, cyano, oxo, hydroxyl, $C_1$-$C_4$alkoxy, $C_3$-$C_7$cycloalkoxy, hydroxyC_1$-$C_4$alkyl-, $C_1$-$C_4$alkoxyC_1$-$C_4$alkyl-, —$OCF_3$, —$NR^5R^6$, $R^5R^6NC_1$-$C_4$alkyl-, —$NHC(O)C_1$-$C_4$alkyl, —$NR^6CONR^5R^6$, —$NR^6SO_2C_1$-$C_4$alkyl, —$NR^6SO_2NR^5R^6$, and $R^9$, wherein when one $R^8$ is hydrogen or deuterium, the other $R^8$ is not hydrogen or deuterium;
   m is 0, 1, 2 or 3;
   Y is C or N;
   or a pharmaceutically acceptable salt thereof.

14. A compound or pharmaceutically acceptable salt according to claim 1 selected from:
   2-(4-cyclopropyl-3-oxo-1-oxa-4,9-diazaspiro[5.5]undecan-9-yl)-2-(4-(quinolin-7-yl)phenyl)acetic acid;
   2-(4-cyclopropyl-3-oxo-1-oxa-4,9-diazaspiro[5.5]undecan-9-yl)-2-(4-(quinolin-7-yl)phenyl)acetamide;
   2-(4-cyclopropyl-3-oxo-1-oxa-4,9-diazaspiro[5.5]undecan-9-yl)-N,N-dimethyl-2-(4-(quinolin-7-yl)phenyl)acetamide;
   2-(4-cyclopropyl-3-oxo-1-oxa-4,9-diazaspiro[5.5]undecan-9-yl)-N-methyl-2-(4-(quinolin-7-yl)phenyl)acetamide;
   methyl 3-(4-cyclopropyl-3-oxo-1-oxa-4,9-diazaspiro[5.5]undecan-9-yl)-3-(4-(quinolin-7-yl)phenyl)propanoate;
   3-(4-cyclopropyl-3-oxo-1-oxa-4,9-diazaspiro[5.5]undecan-9-yl)-3-(4-(quinolin-7-yl)phenyl)propanoic acid;
   (−)-3-(4-cyclopropyl-3-oxo-1-oxa-4,9-diazaspiro[5.5]undecan-9-yl)-3-(4-(quinolin-7-yl)phenyl)propanamide;
   (+)-3-(4-cyclopropyl-3-oxo-1-oxa-4,9-diazaspiro[5.5]undecan-9-yl)-3-(4-(quinolin-7-yl)phenyl)propanamide;
   (+)-2-(4-cyclopropyl-3-oxo-1-oxa-4,9-diazaspiro[5.5]undec-9-yl)-2-[2-fluoro-4-(7-quinolinyl)phenyl]acetamide;
   (−)-2-(4-cyclopropyl-3-oxo-1-oxa-4,9-diazaspiro[5.5]undec-9-yl)-2-[2-fluoro-4-(7-quinolinyl)phenyl]acetamide;
   (+)-2-(4-cyclopropyl-3-oxo-1-oxa-4,9-diazaspiro[5.5]undecan-9-yl)-2-(2-fluoro-4-(3-methylquinolin-7-yl)phenyl)acetamide;
   (−)-2-(4-cyclopropyl-3-oxo-1-oxa-4,9-diazaspiro[5.5]undecan-9-yl)-2-(2-fluoro-4-(3-methylquinolin-7-yl)phenyl)acetamide;
   4-cyclopropyl-9-(1-(4-(quinolin-7-yl)phenypethyl)-1-oxa-4,9-diazaspiro[5.5]undecan-3-one;
   4-cyclopropyl-9-(1-(3-fluoro-4'-methoxy-[1,1'-biphenyl]-4-yl)ethyl)-1-oxa-4,9-diazaspiro[5.5]undecan-3-one;
   (+)-4-cyclopropyl-9-(1-(2-fluoro-4-(quinolin-7-yl)phenyl)ethyl)-1-oxa-4,9-diazaspiro[5.5]undecan-3-one;
   (−)-4-cyclopropyl-9-(1-(2-fluoro-4-(quinolin-7-yl)phenyl)ethyl)-1-oxa-4,9-diazaspiro[5.5]undecan-3-one;
   2-(4-cyclopropyl-3-oxo-1-oxa-4,9-diazaspiro[5.5]undecan-9-yl)-2-(4-(quinolin-7-yl)phenyl)acetonitrile;
   2-(4-cyclopropyl-3-oxo-1-oxa-4,9-diazaspiro[5.5]undecan-9-yl)-2-(2-fluoro-4-(quinolin-7-yl)phenyl)acetic acid;
   (−)-2-(4-cyclopropyl-3-oxo-1-oxa-4,9-diazaspiro[5.5]undecan-9-yl)-2-(4-(quinolin-7-yl)phenyl)acetamide;
   (+)-2-(4-cyclopropyl-3-oxo-1-oxa-4,9-diazaspiro[5.5]undecan-9-yl)-2-(4-(quinolin-7-yl)phenyl)acetamide;
   2-(4-cyclopropyl-3-oxo-1-oxa-4,9-diazaspiro[5.5]undecan-9-yl)-2-(2-fluoro-4-(quinolin-7-yl)phenyl)acetamide;
   4-cyclopropyl-9-(2-hydroxy-1-(4-(quinolin-7-yl)phenyl)ethyl)-1-oxa-4,9-diazaspiro[5.5]undecan-3-one;
   methyl 3-(4-cyclopropyl-3-oxo-1-oxa-4,9-diazaspiro[5.5]undecan-9-yl)-3-(2-fluoro-4-(quinolin-7-yl)phenyl)propanoate;
   4-cyclopropyl-9-(2-oxo-1-(4-(quinolin-7-yl)phenyl)propyl)-1-oxa-4,9-diazaspiro[5.5]undecan-3-one;
   (+)-4-cyclopropyl-9-(1-(2-fluoro-4-(quinolin-7-yl)phenyl)-2-hydroxyethyl)-1-oxa-4,9-diazaspiro[5.5]undecan-3-one;
   (−)-4-cyclopropyl-9-(1-(2-fluoro-4-(quinolin-7-yl)phenyl)-2-hydroxyethyl)-1-oxa-4,9-diazaspiro[5.5]undecan-3-one;
   (+)-2-(4-cyclopropyl-3-oxo-1-oxa-4,9-diazaspiro[5.5]undecan-9-yl)-2-(2-fluoro-4-(quinolin-7-yl)phenyl)-N-methylacetamide;
   (−)-2-(4-cyclopropyl-3-oxo-1-oxa-4,9-diazaspiro[5.5]undecan-9-yl)-2-(2-fluoro-4-(quinolin-7-yl)phenyl)-N-methylacetamide;
   (+)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide;
   (−)-2-(2-fluoro-4-(quinolin-7-yl)phenyl)-2-(4-(1-(hydroxymethyl)cyclopropyl)-3-oxo-1-oxa-4,9-diazaspiro[5.5]undecan-9-yl)acetamide;
   (+)-2-(4-cyclopropyl-3-oxo-1-oxa-4,9-diazaspiro[5.5]undecan-9-yl)-2-(2-fluoro-4-(2-methylquinolin-7-yl)phenyl)acetamide;
   (−)-2-(4-cyclopropyl-3-oxo-1-oxa-4,9-diazaspiro[5.5]undecan-9-yl)-2-(2-fluoro-4-(2-methylquinolin-7-yl)phenyl)acetamide;

2-(4-cyclopropyl-3-oxo-1-oxa-4,9-diazaspiro[5.5]undecan-9-yl)-2-(3-fluoro-4'-methoxy-[1,1'-biphenyl]-4-yl)acetamide;

2-(4-cyclopropyl-3-oxo-1-oxa-4,9-diazaspiro[5.5]undecan-9-yl)-2-(2-fluoro-4-(2-hydroxyquinolin-7-yl)phenyl)acetamide;

2-(4-cyclopropyl-3-oxo-1-oxa-4,9-diazaspiro[5.5]undecan-9-yl)-2-(3,4'-difluoro-[1,1'-biphenyl]-4-yl)acetamide;

(+)-2-(4-cyclopropyl-3-oxo-1-oxa-4,9-diazaspiro[5.5]undecan-9-yl)-2-(2-fluoro-4-(quinolin-7-yl)phenyl)-N-hydroxyacetamide;

(−)-2-(4-cyclopropyl-3-oxo-1-oxa-4,9-diazaspiro[5.5]undecan-9-yl)-2-(2-fluoro-4-(quinolin-7-yl)phenyl)-N-hydroxyacetamide;

(+)-4-cyclopropyl-9-(1-(2,6-difluoro-4-(quinolin-7-yl)phenyl)-2-hydroxyethyl)-1-oxa-4,9-diazaspiro[5.5]undecan-3-one;

(−)-4-cyclopropyl-9-(1-(2,6-difluoro-4-(quinolin-7-yl)phenyl)-2-hydroxyethyl)-1-oxa-4,9-diazaspiro[5.5]undecan-3-one;

(+)-2-(4-cyclopropyl-3-oxo-1-oxa-4,9-diazaspiro[5.5]undecan-9-yl)-2-(2-fluoro-4-(quinolin-5-yl)phenyl)acetamide;

(−)-2-(4-cyclopropyl-3-oxo-1-oxa-4,9-diazaspiro[5.5]undecan-9-yl)-2-(2-fluoro-4-(quinolin-5-yl)phenyl)acetamide;

(−)-2-(4-cyclopropyl-3-oxo-1-oxa-4,9-diazaspiro[5.5]undecan-9-yl)-2-(2-fluoro-4-(quinolin-7-yl)phenyl)-N,N-dimethylacetamide;

(+)-2-(4-cyclopropyl-3-oxo-1-oxa-4,9-diazaspiro[5.5]undecan-9-yl)-2-(2-fluoro-4-(quinolin-7-yl)phenyl)-N,N-dimethylacetamide;

(+)-2-(4-cyclopropyl-3-oxo-1-oxa-4,9-diazaspiro[5.5]undecan-9-yl)-2-(2-fluoro-4-(2-methylquinolin-5-yl)phenyl)acetamide;

(−)-2-(4-cyclopropyl-3-oxo-1-oxa-4,9-diazaspiro[5.5]undecan-9-yl)-2-(2-fluoro-4-(2-methylquinolin-5-yl)phenyl)acetamide;

(+)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate;

(−)-methyl 2-(4-cyclopropyl-3-oxo-1-oxa-4,9-diazaspiro[5.5]undecan-9-yl)-2-(2-fluoro-4-(3-methoxyquinolin-7-yl)phenyl)acetate;

(+)-2-(4-cyclopropyl-3-oxo-1-oxa-4,9-diazaspiro[5.5]undecan-9-yl)-2-(2-fluoro-4-(2-hydroxyquinolin-7-yl)phenyl)acetamide;

(−)-2-(4-cyclopropyl-3-oxo-1-oxa-4,9-diazaspiro[5.5]undecan-9-yl)-2-(2-fluoro-4-(2-hydroxyquinolin-7-yl)phenyl)acetamide;

(+)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide;

(−)-2-(4-cyclopropyl-3-oxo-1-oxa-4,9-diazaspiro[5.5]undecan-9-yl)-2-(2-fluoro-4-(quinolin-7-yl)phenyl)-N-methoxyacetamide;

(+)-2-(4-ethyl-3-oxo-1-oxa-4,9-diazaspiro[5.5]undecan-9-yl)-2-(2-fluoro-4-(8-fluoroquinolin-7-yl)phenyl)acetamide;

(−)-2-(4-ethyl-3-oxo-1-oxa-4,9-diazaspiro[5.5]undecan-9-yl)-2-(2-fluoro-4-(8-fluoroquinolin-7-yl)phenyl)acetamide;

(+)-2-(4-ethyl-3-oxo-1-oxa-4,9-diazaspiro[5.5]undecan-9-yl)-2-(2-fluoro-4-(8-methoxyquinolin-7-yl)phenyl)acetamide;

(−)-2-(4-ethyl-3-oxo-1-oxa-4,9-diazaspiro[5.5]undecan-9-yl)-2-(2-fluoro-4-(8-methoxyquinolin-7-yl)phenyl)acetamide;

2-(4-cyclopropyl-3-oxo-1-oxa-4,9-diazaspiro[5.5]undecan-9-yl)-2-(2,6-difluoro-4-(quinolin-7-yl)phenyl)acetamide;

ethyl 2-(4-ethyl-3-oxo-1-oxa-4,9-diazaspiro[5.5]undecan-9-yl)-2-(2-fluoro-4-(quinolin-7-yl)phenyl)acetate;

(+)-2-(4-ethyl-3-oxo-1-oxa-4,9-diazaspiro[5.5]undecan-9-yl)-2-(2-fluoro-4-(quinolin-7-yl)phenyl)acetamide;

(−)-2-(4-ethyl-3-oxo-1-oxa-4,9-diazaspiro[5.5]undecan-9-yl)-2-(2-fluoro-4-(quinolin-7-yl)phenyl)acetamide;

(+)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide;

(−)-2-(4-cyclopropyl-3-oxo-1-oxa-4,9-diazaspiro[5.5]undecan-9-yl)-2-(2-fluoro-4-(3-fluoroquinolin-7-yl)phenyl)acetamide;

2-(4-(3-cyanoquinolin-7-yl)-2-fluorophenyl)-2-(4-cyclopropyl-3-oxo-1-oxa-4,9-diazaspiro[5.5]undecan-9-yl)acetamide;

(+)-2-(4-(3-cyanoquinolin-7-yl)-2-fluorophenyl)-2-(4-cyclopropyl-3-oxo-1-oxa-4,9-diazaspiro[5.5]undecan-9-yl)acetamide;

(−)-2-(4-(3-cyanoquinolin-7-yl)-2-fluorophenyl)-2-(4-cyclopropyl-3-oxo-1-oxa-4,9-diazaspiro[5.5]undecan-9-yl)acetamide;

(+)-2-(4-(3-chloroquinolin-7-yl)-2-fluorophenyl)-2-(4-cyclopropyl-3-oxo-1-oxa-4,9-diazaspiro[5.5]undecan-9-yl)acetamide;

(−)-2-(4-(3-chloroquinolin-7-yl)-2-fluorophenyl)-2-(4-cyclopropyl-3-oxo-1-oxa-4,9-diazaspiro[5.5]undecan-9-yl)acetamide;

2-(4-cyclopropyl-3-oxo-1-oxa-4,9-diazaspiro[5.5]undecan-9-yl)-2-(2-fluoro-4-(8-fluoroquinolin-7-yl)phenyl)acetamide;

(+)-2-(4-cyclopropyl-3-oxo-1-oxa-4,9-diazaspiro[5.5]undecan-9-yl)-2-(2-fluoro-4-(8-fluoroquinolin-7-yl)phenyl)acetamide;

(−)-2-(4-cyclopropyl-3-oxo-1-oxa-4,9-diazaspiro[5.5]undecan-9-yl)-2-(2-fluoro-4-(8-fluoroquinolin-7-yl)phenyl)acetamide;

2-(2,6-difluoro-4-(quinolin-7-yl)phenyl)-2-(4-ethyl-3-oxo-1-oxa-4,9-diazaspiro[5.5]undecan-9-yl)acetamide;

(+)-2-(2,6-difluoro-4-(quinolin-7-yl)phenyl)-2-(4-ethyl-3-oxo-1-oxa-4,9-diazaspiro[5.5]undecan-9-yl)acetamide;

(−)-2-(2,6-difluoro-4-(quinolin-7-yl)phenyl)-2-(4-ethyl-3-oxo-1-oxa-4,9-diazaspiro[5.5]undecan-9-yl)acetarnide;

(+)-2-(4-cyclopropyl-3-oxo-1-oxa-4,9-diazaspiro[5.5]undecan-9-yl)-2-(2,6-difluoro-4-(quinolin-7-yl)phenyl)acetamide;

(−)-2-(4-cyclopropyl-3-oxo-1-oxa-4,9-diazaspiro[5.5]undecan-9-yl)-2-(2,6-difluoro-4-(quinolin-7-yl)phenyl)acetamide;

(+)-2-(4-cyclopropyl-3-oxo-1-oxa-4,9-diazaspiro[5.5]undecan-9-yl)-2-(2-fluoro-4-(3-methoxyquinolin-7-yl)phenyl)acetamide;

(−)-2-(4-cyclopropyl-3-oxo-1-oxa-4,9-diazaspiro[5.5]undecan-9-yl)-2-(2-fluoro-4-(3-methoxyquinolin-7-yl)phenyl)acetamide;

(+)-2-(4-cyclopropyl-3-oxo-1-oxa-4,9-diazaspiro[5.5]undecan-9-yl)-2-(2-fluoro-4-(8-methoxyquinolin-7-yl)phenyl)acetamide;

(−)-2-(4-cyclopropyl-3-oxo-1-oxa-4,9-diazaspiro[5.5]undecan-9-yl)-2-(2-fluoro-4-(8-methoxyquinolin-7-yl)phenypacetarnide;

4-cyclopropyl-9-((2-fluoro-4-(quinolin-7-yl)phenyl)(4 H-1,2,4-triazol-3-yl)methyl)-1-oxa-4,9-diazaspiro[5.5]undecan-3-one;

(+)-4-cyclopropyl-9-((2-fluoro-4-(quinolin-7-yl)phenyl)(4H-1,2,4-triazol-3-yl)methyl)-1-oxa-4,9-diazaspiro[5.5]undecan-3-one;

(−)-4-cyclopropyl-9-((2-fluoro-4-(quinolin-7-yl)phenyl)(4 H-1,2,4-triazol-3-yl)methyl)-1 -oxa-4,9-diazaspiro[5.5]undecan-3-one;

2-(4-(3-cyanoquinolin-7-yl)-2-fluorophenyl)-2-(4-ethyl-3-oxo-1-oxa-4,9-diazaspiro[5.5]undecan-9-yl)acetamide;

(+)-2-(4-(3-cyanoquinolin-7-yl)-2-fluorophenyl)-2-(4-ethyl-3-oxo-1-oxa-4,9-diazaspiro[5.5]undecan-9-yl)acetamide;

(−)-2-(4-(3-cyanoquinolin-7-yl)-2-fluorophenyl)-2-(4-ethyl-3-oxo-1-oxa-4,9-diazaspiro[5.5]undecan-9-yl)acetamide;

2-(4-ethyl-3-oxo-1-oxa-4,9-diazaspiro[5.5]undecan-9-yl)-2-(2-fluoro-4-(3-methylquinolin-7-yl)phenyl)acetamide;

(+)-2-(4-ethyl-3-oxo-1 -oxa-4,9-diazaspiro[5.5]undecan-9-yl)-2-(2-fluoro-4-(3-methylquinolin-7-yl)phenyl)acetamide;

(−)-2-(4-ethyl-3-oxo-1-oxa-4,9-diazaspiro[5.5]undecan-9-yl)-2-(2-fluoro-4-(3-methylquinolin-7-yl)phenyl)acetamide;

(+)-2-(4-(3-chloroquinolin-7-yl)-2-fluorophenyl)-2-(4-ethyl-3-oxo-1-oxa-4,9-diazaspiro[5.5]undecan-9-yl)acetamide;

(−)-2-(4-(3-chloroquinolin-7-yl)-2-fluorophenyl)-2-(4-ethyl-3-oxo-1-oxa-4,9-diazaspiro[5.5]undecan-9-yl)acetamide;

(+)-2-(4-ethyl-3-oxo-1 -oxa-4,9-diazaspiro[5.5]undecan-9-yl)-2-(2-fluoro-4-(3-fluoroquinolin-7-yl)phenyl)acetamide;

(−)-2-(4-ethyl-3-oxo-1-oxa-4,9-diazaspiro[5.5]undecan-9-yl)-2-(2-fluoro-4-(3-fluoroquinolin-7-yl)phenyl)acetamide;

(+)-2-(4-ethyl-3-oxo-1 -oxa-4,9-diazaspiro[5.5]undecan-9-yl)-2-(2-fluoro-4-(3-methoxyquinolin-7-yl)phenyl)acetamide; and (−)-2-(4-ethyl-3-oxo-1-oxa-4,9-diazaspiro[5.5]undecan-9-yl)-2-(2-fluoro-4-(3-methoxyquinolin-7-yl)phenyl)acetamide.

15. A compound or pharmaceutically acceptable salt thereof according to claim 1 wherein the compound has an enantiomeric excess of one enantiomer over the other.

16. A compound or pharmaceutically acceptable salt thereof according to claim 1 wherein the compound is an enantiomerically pure R isomer.

17. A compound or pharmaceutically acceptable salt thereof according to claim 1 wherein the compound is an enantiomerically pure S isomer.

18. A pharmaceutical composition comprising the compound or pharmaceutically acceptable salt thereof according to claim 1 and a pharmaceutically acceptable carrier.

19. A method of treating a cancer selected from the group consisting of: gastric, brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid, that comprises administering to a human in need thereof an effective amount of a compound or pharmaceutically acceptable salt thereof according to claim 1.

20. A method of treating a cancer selected from the group consisting of: gastric, brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid, in a mammal in need thereof, which comprises: administering to such mammal a therapeutically effective amount of
a) a compound of Formula (I), as described in claim 1 or a pharmaceutically acceptable salt thereof; and
b) at least one anti-neoplastic agent.

21. A compound of claim 1 which is:
(+)-2-(4-cyclopropyl-3-oxo-1-oxa-4,9-diazaspiro[5.5]undec-9-yl)-2-[2-fluoro-4-(7-quinolinyl)phenyl]acetamide;
or a pharmaceutically acceptable salt thereof.

22. A compound of claim 21 which is:
(+)-2-(4-cyclopropyl-3-oxo-1-oxa-4,9-diazaspiro[5.5]undec-9-yl)-2-[2-fluoro-4-(7-quinolinyl)phenyl]acetamide.

23. A compound of claim 21 which is a pharmaceutically acceptable salt of:
(+)-2-(4-cyclopropyl-3-oxo-1-oxa-4,9-diazaspiro[5.5]undec-9-yl)-2-[2-fluoro-4-(7-quinolinyl)phenyl]acetamide.

24. A method of treating a cancer selected from the group consisting of:
gastric, brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid, that comprises administering to a human in need thereof an effective amount of a compound or pharmaceutically acceptable salt thereof according to claim 21.

25. A method of treating a cancer selected from the group consisting of: gastric, brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid, in a mammal in need thereof, which comprises: administering to such mammal a therapeutically effective amount of
a) a compound according to claim 21; and
b) at least one anti-neoplastic agent.

26. A pharmaceutical composition comprising a compound according to claim 21 and a pharmaceutically acceptable carrier.

* * * * *